US011505828B2

(12) United States Patent
Chell et al.

(10) Patent No.: US 11,505,828 B2
(45) Date of Patent: Nov. 22, 2022

(54) METHODS FOR SPATIAL ANALYSIS USING RNA-TEMPLATED LIGATION

(71) Applicant: 10x Genomics, Inc., Pleasanton, CA (US)

(72) Inventors: James Michael Chell, Stockholm (SE); Marlon Stoeckius, Stockholm (SE); Jonathan Alles, Berlin (DE); Caroline Julie Gallant, Stockholm (SE); Christina Galonska, Stockholm (SE); Layla Katiraee, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/220,534

(22) Filed: Apr. 1, 2021

(65) Prior Publication Data

US 2021/0285046 A1 Sep. 16, 2021

Related U.S. Application Data

(63) Continuation of application No. PCT/US2020/066720, filed on Dec. 22, 2020.

(60) Provisional application No. 63/108,088, filed on Oct. 30, 2020, provisional application No. 63/087,061, filed on Oct. 2, 2020, provisional application No. 62/969,458, filed on Feb. 3, 2020, provisional application No. 62/952,736, filed on Dec. 23, 2019.

(51) Int. Cl.
| | | |
|---|---|---|
| C12Q 1/68 | (2018.01) | |
| C12Q 1/6876 | (2018.01) | |
| C12Q 1/6811 | (2018.01) | |
| C12Q 1/25 | (2006.01) | |
| C12Q 1/6816 | (2018.01) | |
| C12Q 1/6841 | (2018.01) | |
| C12Q 1/6851 | (2018.01) | |

(52) U.S. Cl.
CPC ............ *C12Q 1/6876* (2013.01); *C12Q 1/25* (2013.01); *C12Q 1/6811* (2013.01); *C12Q 1/6816* (2013.01); *C12Q 1/6841* (2013.01); *C12Q 1/6851* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |

(Continued)

FOREIGN PATENT DOCUMENTS

| | | |
|---|---|---|
| CN | 1680604 | 10/2005 |
| CN | 101221182 | 7/2008 |

(Continued)

OTHER PUBLICATIONS

Punwaney et al. (Head & Neck, 1999, 21:1, p. 21-29) (Year: 1999).*

(Continued)

*Primary Examiner* — Stephanie K Mummert
(74) *Attorney, Agent, or Firm* — Fish & Richardson P.C.

(57) ABSTRACT

Provided herein are methods of detecting an analyte of interest to interrogate spatial gene expression in a sample using RNA-templated ligation.

30 Claims, 35 Drawing Sheets

(56) References Cited

U.S. PATENT DOCUMENTS

| | | |
|---|---|---|
| 4,965,188 A | 10/1990 | Mullis |
| 5,002,882 A | 3/1991 | Lurmen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,958,775 A | 9/1999 | Wickstrrom |
| 5,965,443 A | 10/1999 | Reznikoff et al. |
| 6,013,440 A | 1/2000 | Lipshutz |
| 6,027,889 A | 2/2000 | Barany et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,172,218 B1 | 1/2001 | Brenner |
| 6,210,891 B1 | 4/2001 | Nyren |
| 6,210,894 B1 | 4/2001 | Bretman |
| 6,214,587 B1 | 4/2001 | Dattagupta |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,300,063 B1 | 10/2001 | Lipshutz et al. |
| 6,309,824 B1 | 10/2001 | Dnnanac |
| 6,344,316 B1 | 2/2002 | Lockhart |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church |
| 6,503,713 B1 | 1/2003 | Rana |
| 6,506,561 B1 | 1/2003 | Cheval et al. |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Pradent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 * | 8/2007 | Lao ................... C12Q 1/682 |
| | | 435/6.12 |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 * | 4/2008 | Fan ................... C12Q 1/6816 |
| | | 435/6.12 |
| 7,378,242 B2 | 5/2008 | Hurt |
| 7,393,665 B2 | 7/2008 | Bienner |
| 7,405,281 B2 | 7/2008 | Xu |
| 7,407,757 B2 | 8/2008 | Brenner |
| 7,537,897 B2 | 5/2009 | Brenner |
| 7,544,473 B2 | 6/2009 | Brennan |
| 7,563,576 B2 | 7/2009 | Chee |
| 7,579,153 B2 | 8/2009 | Brenner |
| 7,582,420 B2 | 9/2009 | Oliphant et al. |
| 7,601,492 B2 | 10/2009 | Fu et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,700,286 B2 | 4/2010 | Stroun et al. |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,914,981 B2 | 3/2011 | Barany et al. |
| 7,955,794 B2 | 6/2011 | Shen et al. |
| 7,960,119 B2 | 6/2011 | Chee |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,288,103 B2 | 10/2012 | Oliphant |
| 8,383,338 B2 | 2/2013 | Kitzman |
| 8,460,865 B2 | 6/2013 | Chee |
| 8,481,257 B2 | 7/2013 | Van Eijk |
| 8,481,292 B2 | 7/2013 | Casbon |
| 8,481,698 B2 | 7/2013 | Lieberman et al. |
| 8,507,204 B2 | 8/2013 | Pierce et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |

(56) References Cited

U.S. PATENT DOCUMENTS

| | | |
|---|---|---|
| 8,951,726 B2 | 2/2015 | Luo et al. |
| 8,951,728 B2 | 2/2015 | Rasmussen |
| 9,005,891 B2 | 4/2015 | Sinicropi et al. |
| 9,023,768 B2 | 5/2015 | Van Eijk |
| 9,062,348 B1 | 6/2015 | Van Eijk |
| 9,080,210 B2 | 7/2015 | Van Eijk |
| 9,085,798 B2 | 7/2015 | Chee |
| 9,194,001 B2 | 11/2015 | Brenner |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,598 B2 | 6/2016 | Chee |
| 9,376,716 B2 | 6/2016 | Van Eijk |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 * | 3/2017 | Barany ............... G01N 33/5308 |
| 9,657,335 B2 | 5/2017 | Van Eijk |
| 9,670,542 B2 | 6/2017 | Van Eijk |
| 9,702,004 B2 | 7/2017 | Van Eijk |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,011,872 B1 | 7/2018 | Belgrade et al. |
| 10,023,907 B2 | 7/2018 | Van Eijk |
| 10,030,261 B2 | 7/2018 | Frisen et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,273,541 B2 | 4/2019 | Hindson et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,550,429 B2 | 2/2020 | Harada et al. |
| 10,633,648 B2 | 4/2020 | Seelig et al. |
| 10,724,078 B2 | 7/2020 | Van Driel et al. |
| 10,774,372 B2 | 9/2020 | Chee et al. |
| 10,774,374 B2 | 9/2020 | Frisen et al. |
| 10,787,701 B2 | 9/2020 | Chee |
| 10,829,803 B2 | 11/2020 | Terbrueggen et al. |
| 10,913,975 B2 | 2/2021 | So et al. |
| 10,914,730 B2 | 2/2021 | Chee et al. |
| 10,927,403 B2 | 2/2021 | Chee et al. |
| 11,008,607 B2 | 5/2021 | Chee |
| 11,046,996 B1 | 6/2021 | Chee et al. |
| 11,067,567 B2 | 7/2021 | Chee |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 2001/0055764 A1 | 12/2001 | Empendocles et al. |
| 2002/0040275 A1 | 4/2002 | Cravatt |
| 2002/0048766 A1 | 4/2002 | Doyle et al. |
| 2002/0055100 A1 | 5/2002 | Kawashima |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0138879 A1 | 7/2003 | Lambalot |
| 2003/0001622 A1 | 8/2003 | Gold |
| 2003/0148335 A1 | 8/2003 | Shen et al. |
| 2003/0165948 A1 | 9/2003 | Alsmadi et al. |
| 2003/0215936 A1 | 11/2003 | Kallioniemi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0019005 A1 | 1/2004 | Van Ness |
| 2004/0033499 A1 | 2/2004 | Ilsley et al. |
| 2004/0067492 A1 | 4/2004 | Peng et al. |
| 2004/0067493 A1 | 4/2004 | Matsuzaki |
| 2004/0082059 A1 | 4/2004 | Webb et al. |
| 2004/0096853 A1 | 5/2004 | Maver |
| 2004/0106110 A1 | 6/2004 | Balasubramanian |
| 2004/0224326 A1 | 11/2004 | Kim et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0100900 A1 | 5/2005 | Kawashima et al. |
| 2005/0130173 A1 | 6/2005 | Leamon et al. |
| 2005/0130188 A1 | 6/2005 | Walt |
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0260653 A1 | 11/2005 | LaBaer |
| 2005/0266417 A1 * | 12/2005 | Barany ................ C12Q 1/6827 435/6.12 |
| 2006/0046313 A1 | 3/2006 | Roth |
| 2006/0105352 A1 | 5/2006 | Qiao et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 * | 12/2006 | Gunderson .......... C12Q 1/6874 435/6.12 |
| 2006/0281109 A1 | 12/2006 | Barr Ost et al. |
| 2007/0020640 A1 | 1/2007 | McCloskev et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0153086 A1 | 6/2008 | Wong |

(56) References Cited

U.S. PATENT DOCUMENTS

| | | |
|---|---|---|
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120043 A1 | 5/2010 | Sood et al. |
| 2010/0120097 A1 | 5/2010 | Matz et al. |
| 2010/0120098 A1 | 5/2010 | Grunenwald et al. |
| 2010/0129874 A1 | 5/2010 | Mito et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Illumina |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0258871 A1 | 10/2012 | Kozlov et al. |
| 2012/0289414 A1 | 11/2012 | Mitra et al. |
| 2013/0005594 A1 | 1/2013 | Terbmeggen et al. |
| 2013/0005600 A1 | 1/2013 | Olek |
| 2013/0035239 A1 | 2/2013 | Kong et al. |
| 2013/0079232 A1 | 3/2013 | Kam et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0274731 A1 | 9/2014 | Raymond et al. |
| 2014/0323330 A1 | 10/2014 | Glezer et al. |
| 2014/0342921 A1 | 11/2014 | Weiner |
| 2015/0000854 A1 | 1/2015 | Gann-Fetter et al. |
| 2015/0376609 A1 | 12/2015 | Hindson et al. |
| 2016/0019337 A1 | 1/2016 | Roberts et al. |
| 2016/0024576 A1 | 1/2016 | Chee |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0333403 A1 | 11/2016 | Chee |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0335410 A1 | 11/2017 | Driscoll et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0094316 A1 | 4/2018 | Oliphant et al. |
| 2018/0105808 A1 | 4/2018 | Mikkelsen et al. |
| 2018/0112209 A1 | 4/2018 | Eshoo |
| 2018/0112261 A1* | 4/2018 | Van Driel ............ C12Q 1/6841 |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291439 A1 | 10/2018 | van Eijk et al. |
| 2018/0312822 A1 | 11/2018 | Lee et al. |
| 2019/0055594 A1 | 2/2019 | Samusik et al. |
| 2019/0085383 A1 | 3/2019 | Church et al. |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0330617 A1 | 10/2019 | Church et al. |
| 2019/0367969 A1 | 12/2019 | Belhoclne et al. |
| 2020/0010891 A1 | 1/2020 | Beechem et al. |
| 2020/0024641 A1 | 1/2020 | Nolan et al. |
| 2020/0048690 A1 | 2/2020 | Chee |
| 2020/0063195 A1 | 2/2020 | Chee |
| 2020/0063196 A1 | 2/2020 | Chee |
| 2020/0080136 A1 | 3/2020 | Zhang et al. |
| 2020/0109443 A1 | 4/2020 | Chee |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iver |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin et al. |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |

(56) References Cited

U.S. PATENT DOCUMENTS

| | | | |
|---|---|---|---|
| 2021/0140982 A1 | 5/2021 | Uytingco et al. | |
| 2021/0150707 A1 | 5/2021 | Weisenfeld et al. | |
| 2021/0155982 A1 | 5/2021 | Yin et al. | |
| 2021/0158522 A1 | 5/2021 | Weisenfeld et al. | |
| 2021/0172007 A1 | 6/2021 | Chee et al. | |
| 2021/0189475 A1 | 6/2021 | Tentori et al. | |
| 2021/0198741 A1 | 7/2021 | Williams | |
| 2021/0199660 A1 | 7/2021 | Williams et al. | |
| 2021/0207202 A1 | 7/2021 | Chee | |
| 2021/0214785 A1 | 7/2021 | Stoeckius | |
| 2021/0222235 A1 | 7/2021 | Chee | |
| 2021/0222241 A1 | 7/2021 | Bharadwaj | |
| 2021/0222242 A1 | 7/2021 | Ramachandran Iyer | |
| 2021/0222253 A1 | 7/2021 | Uytingco | |
| 2021/0223227 A1 | 7/2021 | Stoeckius | |
| 2021/0230584 A1 | 7/2021 | Mikkelsen et al. | |
| 2021/0230681 A1 | 7/2021 | Patterson et al. | |
| 2021/0230692 A1 | 7/2021 | Daugharthy et al. | |
| 2021/0238664 A1 | 8/2021 | Bava et al. | |
| 2021/0238675 A1 | 8/2021 | Bava et al. | |
| 2021/0238680 A1 | 8/2021 | Bava | |
| 2021/0247316 A1 | 8/2021 | Bava | |
| 2021/0255175 A1 | 8/2021 | Chee et al. | |
| 2021/0262018 A1 | 8/2021 | Bava et al. | |
| 2021/0262019 A1 | 8/2021 | Alvarado Martinez et al. | |
| 2021/0269864 A1 | 9/2021 | Chee | |
| 2021/0270822 A1 | 9/2021 | Chee | |
| 2021/0285036 A1 | 9/2021 | Yin et al. | |
| 2021/0292748 A1 | 9/2021 | Frisen et al. | |
| 2021/0292822 A1 | 9/2021 | Frisen et al. | |
| 2021/0317510 A1* | 10/2021 | Chee | C12Q 1/6841 |
| 2021/0317524 A1 | 10/2021 | Lucero et al. | |
| 2021/0324457 A1 | 10/2021 | Ramachandran Iyer et al. | |
| 2021/0332424 A1 | 10/2021 | Schnall-Levin | |
| 2021/0332425 A1 | 10/2021 | Pfeiffer et al. | |
| 2021/0003482 A1 | 11/2021 | Chell et al. | |
| 2022/0002791 A1 | 1/2022 | Frisen et al. | |
| 2022/0003755 A1 | 1/2022 | Chee | |
| 2022/0010367 A1 | 1/2022 | Ramachandran Iyer et al. | |
| 2022/0017951 A1 | 1/2022 | Ramachandran Iyer et al. | |
| 2022/0025446 A1 | 1/2022 | Shah | |
| 2022/0025447 A1 | 1/2022 | Tentori et al. | |
| 2022/0033888 A1 | 2/2022 | Schnall-Levin et al. | |
| 2022/0049293 A1 | 2/2022 | Frenz et al. | |
| 2022/0064630 A1 | 3/2022 | Bent et al. | |
| 2022/0081728 A1 | 3/2022 | Williams | |
| 2022/0090058 A1 | 3/2022 | Frisen et al. | |
| 2022/0090175 A1 | 3/2022 | Uylingco et al. | |
| 2022/0090181 A1 | 3/2022 | Gallant et al. | |
| 2022/0098576 A1 | 3/2022 | Dadhwal | |
| 2022/0098661 A1 | 3/2022 | Chew et al. | |
| 2022/0106632 A1 | 4/2022 | Galonska et al. | |
| 2022/0106633 A1 | 4/2022 | Engblom et al. | |
| 2022/0112486 A1 | 4/2022 | Ramachandran Iyer et al. | |
| 2022/0112545 A1 | 4/2022 | Chee | |
| 2022/0119869 A1 | 4/2022 | Ramachandran Iyer et al. | |
| 2022/0127659 A1 | 4/2022 | Frisen et al. | |
| 2022/0127666 A1 | 4/2022 | Katiraee et al. | |
| 2022/0127672 A1 | 4/2022 | Stoeckius | |
| 2022/0145361 A1 | 5/2022 | Frenz et al. | |

FOREIGN PATENT DOCUMENTS

| | | | |
|---|---|---|---|
| CN | 108949924 | 12/2018 | |
| DE | 102008025656 | 12/2009 | |
| EP | 1782737 | 5/2007 | |
| EP | 1910562 | 4/2008 | |
| EP | 1923471 | 5/2008 | |
| EP | 2002017 | 12/2008 | |
| EP | 2292788 | 3/2011 | |
| EP | 2302070 | 3/2011 | |
| EP | 2881465 | 6/2015 | |
| EP | 3013984 | 5/2016 | |
| EP | 3511423 | 7/2019 | |
| EP | 3541956 | 9/2019 | |
| JP | 2007-014297 | 1/2007 | |
| JP | 2007-074967 | 3/2007 | |
| JP | 2009-036694 | 2/2009 | |
| WO | WO 1989/010977 | 11/1989 | |
| WO | WO 1991/006678 | 5/1991 | |
| WO | WO 1995/023875 | 9/1995 | |
| WO | WO 1995/025116 | 9/1995 | |
| WO | WO 1995/035505 | 12/1995 | |
| WO | WO 1997/31256 | 8/1997 | |
| WO | WO 2000/17390 | 3/2000 | |
| WO | WO-0106012 A1 * | 1/2001 | C07H 21/04 |
| WO | WO 2001/009363 | 2/2001 | |
| WO | WO 2001/042796 | 6/2001 | |
| WO | WO 2001/090415 | 11/2001 | |
| WO | WO 2001/096608 | 12/2001 | |
| WO | WO 2.002/059364 | 8/2002 | |
| WO | WO 2002/059355 | 8/2002 | |
| WO | WO 2002/077283 | 10/2002 | |
| WO | WO 2003/002979 | 1/2003 | |
| WO | WO 2003/008538 | 1/2003 | |
| WO | WO 2003/010176 | 2/2003 | |
| WO | WO 2003/102233 | 12/2003 | |
| WO | WO 2004/015080 | 2/2004 | |
| WO | WO 2.004/067759 | 8/2004 | |
| WO | WO 2005/007814 | 1/2005 | |
| WO | WO 2005/010145 | 2/2005 | |
| WO | WO 2005/026387 | 3/2005 | |
| WO | WO 2005/042759 | 5/2005 | |
| WO | WO 2005/113804 | 12/2005 | |
| WO | WO 2006/020515 | 2/2006 | |
| WO | WO 2006/124771 | 11/2006 | |
| WO | WO 2007/041689 | 4/2007 | |
| WO | WO 2007/060599 | 5/2007 | |
| WO | WO 2007/073171 | 6/2007 | |
| WO | WO 2007/076726 | 7/2007 | |
| WO | WO 2007/139766 | 12/2007 | |
| WO | WO 2007/145612 | 12/2007 | |
| WO | WO 2008/022332 | 2/2008 | |
| WO | WO 2008/069906 | 6/2008 | |
| WO | WO 2009/032167 | 3/2009 | |
| WO | WO 2009/152928 | 12/2009 | |
| WO | WO 2010/019826 | 2/2010 | |
| WO | WO 2010/027870 | 3/2010 | |
| WO | WO 2010/126614 | 11/2010 | |
| WO | WO 2011/008502 | 1/2011 | |
| WO | WO 2011/062933 | 5/2011 | |
| WO | WO 2011/068088 | 6/2011 | |
| WO | WO 2012/049316 | 4/2012 | |
| WO | WO 2012/071428 | 5/2012 | |
| WO | WO 2012/129242 | 9/2012 | |
| WO | WO-2012140224 A1 * | 10/2012 | C12N 15/11 |
| WO | WO 2012/159089 | 11/2012 | |
| WO | WO 2013/123442 | 8/2013 | |
| WO | WO 2013/138510 | 9/2013 | |
| WO | WO 2013/142389 | 9/2013 | |
| WO | WO 2013/150083 | 10/2013 | |
| WO | WO 2014/044724 | 3/2014 | |
| WO | WO 2014/144713 | 9/2014 | |
| WO | WO 2014/152397 | 9/2014 | |
| WO | WO 2014/210223 | 12/2014 | |
| WO | WO 2014/210225 | 12/2014 | |
| WO | WO 2015/161173 | 10/2015 | |
| WO | WO 2016/138496 | 9/2016 | |
| WO | WO2016/138500 | 9/2016 | |
| WO | WO 2016/166128 | 10/2016 | |
| WO | WO 2016/168825 | 10/2016 | |
| WO | WO 2016/172362 | 10/2016 | |
| WO | WO 2017/019456 | 2/2017 | |
| WO | WO 2017/019481 | 2/2017 | |
| WO | WO-2017019456 A2 * | 2/2017 | C12Q 1/6816 |
| WO | WO 2017/075265 | 5/2017 | |
| WO | WO 2017/075293 | 5/2017 | |
| WO | WO 2017/096158 | 7/2017 | |
| WO | WO 2017/156336 | 9/2017 | |
| WO | WO 2017/184984 | 10/2017 | |
| WO | WO 2017/192633 | 11/2017 | |
| WO | WO 2018/023068 | 2/2018 | |
| WO | WO 2018/045181 | 3/2018 | |
| WO | WO 2018/064640 | 4/2018 | |

(56) References Cited

FOREIGN PATENT DOCUMENTS

| | | |
|---|---|---|
| WO | WO 2018/085599 | 5/2018 |
| WO | WO 2018/091676 | 5/2018 |
| WO | WO-2018091676 A1 * | 5/2018 ............ C12Q 1/6834 |
| WO | WO 2018/136856 | 7/2018 |
| WO | WO 2018/144582 | 8/2018 |
| WO | WO 2019/165318 | 8/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/112604 | 6/2020 |
| WO | WO 2020/123301 | 6/2020 |
| WO | WO 2020/123305 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/176788 | 9/2020 |
| WO | WO 2020/190509 | 9/2020 |
| WO | WO 2020/206285 | 10/2020 |
| WO | WO 2020/219901 | 10/2020 |
| WO | WO 2020/243579 | 12/2020 |
| WO | WO 2021/041974 | 3/2021 |
| WO | WO 2021/067246 | 4/2021 |
| WO | WO 2021/091611 | 5/2021 |
| WO | WO 2021/092433 | 5/2021 |
| WO | WO 2021/097255 | 5/2021 |
| WO | WO 2021/119320 | 6/2021 |
| WO | WO 2021/133849 | 7/2021 |
| WO | WO 2021/168261 | 8/2021 |
| WO | WO 2021/168278 | 8/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |

OTHER PUBLICATIONS

Zieba et al. (Clin Chem, 2010, 56:1, p. 99-110) (Year: 2010).*
Salmen et al. (Nature Protocols, 2018, vol. 13, 2501-2534) (Year: 2018).*
U.S. Appl. No. 60/416,118, filed Oct. 3, 2002, Fan et al.
Affymetric, "GeneChip Human Genome U133 Set," retrieved from the Internet on the World Wide Web at affymetrix.com/support/technical/datasheets/hgu133_datasheet.pdf, retrieved on Feb. 26, 2003, 2 pages.
Affymetric, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles vims mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Armani et ai, "2D-PCR: a method of mapping DNA in tissue sections," Lab Chip, 2009, 9(24):3526-34.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Baugh et al., "Quantitative analysis of mRNA amplification by in vitro transcription," Nucleic Acids Res., 2001, 29(5):e29, 9 pages.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Birney et al., "Identification and analysis of functional elements in 1% of the human genome by the ENCODE pilot project," Nature, 2007, 447(7146):799-816.
Blokzijl et al. "Profiling protein expression and interactions: proximity ligation as a tool for personalized medicine," J Intern. Med., 2010, 268(3):232-245.
Blow, "Tissue Issues," Nature, 2007, 448(7156):959-962.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-4670.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burton et al. "Coverslip Mounted-Immersion Cycled in Situ RT-PCR for the Localization of mRNA in Tissue Sections," Biotechniques, 1998, 24(1):92-100.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.
Chen et al., "Expansion microscopy." Science, 2015, 347(6221):543-548.
Chen et al., "Spatially resolved, highly multiplexed RNA profiling in single cells," Science, 2015, 348(6233):aaa6090, 21 pages.
Constantine et al., "Use of genechip high-density oligonucleotide arrays for gene expression monitoring," Life Sceience News, Amersham Life Science, 1998, pp. 11-14.

(56) References Cited

OTHER PUBLICATIONS

Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cujec et al., "Selection of v-abl tyrosine kinase substrate sequences from randomized peptide and cellular proteomic libraries using mRNA display," Chemistry and Biology, 2002, 9(2):233-264.
Dahl et al., "Circle-to-circle amplification for precise and sensitive DNA analysis," Proc. Natl. Acad. Sci., 2004, 101(13):4548-4553.
Darmanis et al.,"ProteinSeq: High-Performance Proteomic Analyses by Proximity, Ligation and Next Generation Sequencing," PLos One, 2011, 6(9):e25583, 10 pages.
Daubendiek et al.. "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Dean et al., "Comprehensive human genome amplification using multiple displacement amplification," Proc Natl. Acad. Sci. USA, 2002, 99(8):5261-66.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides." Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges." Clin Chem, 2010, 56(2):186-193.
Eng et al., "Profiling the transcriptome with RNA SPOTs," Nat Methods., 2017, 14(12):1153-1155.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Counting individual DNA molecules by the stochastic attachment, of diverse labels," PNAS, 2011, 108(22):9026-9031.
Fullwood et al., "Next-generation DNA sequencing of paired-end tags (PET) fortranscriptome and genome analyses," Genome Res., 2009, 19(4):521-532.
Gene.@amys[online], BeadArray Technology, available on or before Feb. 14, 2015, via Internet Archive: Wayback Alachine URL <https://web.archive.org/web/20150214084616/http://genearrays.com/services/microarrays/illumina/beadarray-technology/>, [retrieved on Jan. 30, 2020], 3 pages.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes." Nucleic Acids Res., 1986, 14(22):9171-9191.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research. 2004, 14(5):870-877.
He et al., "In situ synthesis of protein arrays." Current Opinion in Biotechnology, 2008, 19(1);4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads." Nature Methods, 2010, 7(2):119-25.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kap et al., "Histological assessment of PAXgene tissue fixation and stabilization reagents," PLoS One, 2011, 6:e27704, I0 pages.
Kapteyn el al., "Incorporation of non-natural nucleotides into template-switching oligonucleotides reduces background and improves cDNA synthesis from very small RNA samples," BMC Genomics, Jul. 2010, 11:413, 9 pages.
Korbel et al., "Paired-end mapping reveals extensive structural variation in the human genome," Science, 2007, 318(5849):420-426.
Kozlov et al., "A highly scalable peptide-based assay system for proteomics," PLoS ONE, 2012, 7(6):e37441, 10 pages.
Kozlov et al., "A method for rapid protease substrate evaluation and optimization," Comb Chem High Throughput Screen, 2006, 9(6):481-87.
Kurz et al., "cDNA—protein fusions: covalent protein—gene conjugates for the in vitro selection of peptides and proteins," ChemBioChem., 2001, 2(9):666-72.
Lage et al., "Whole genome analysis of genetic alterations in small DNA samples using hyperbranched strand displacement amplification and array-CGH," Genome Research, 2003, 13(2):294-307.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Leriche et al., "Cleavable linkers in chemical biology," Bioorganic & Medicinal Chemistry, 2012, 20:571-582.
Li et al., "A photocleavable fluorescent nucleotide for DNA sequencing and analysis," Proc. Natl. Acad. Sci., 2003, 100(2):414-419.
Li et al., "RASL-seq for Massively Parallel and Quantitative Analysis of Gene Expression," Curr Protoc Mol Biol., Apr. 2012, 4(13):1-10.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet., 1998, 19(3):225-232.

(56) References Cited

OTHER PUBLICATIONS

Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated form *Pyrococcus furiosus*," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lyck et al., "Immunohistochemical markers for quantitative studies of neurons and glia in human neocortex," J Histochem Cytochem, 2008, 56(3):201-21.
MacIntyre, "Unmasking antigens for immunohistochemistry.," Br J Biomed Sci., 2001, 58(3):190-6.
Marx, "Method of the Year: spatially resolved transcriptomics," Nature Methods, 2021, 18(1):9-14.
McCloskey et al., "Encoding PCR products with batch-stamps and barcodes," Biochem. Genet., 2007, 45(11-12):761-767.
Metzker, "Sequencing technologies—tire next generation," Nature Reviews Genetics, 2010, 11(1):31-46.
Miller et al., "Basic concepts of microarrays and potential applications in clinical microbiology," Clinical Microbiology Reviews, 2009, 22(4):611-633.
Mishra et al., "Three-dimensional genome architecture and emerging technologies: looping in disease," Genome Medicine, 2017, 9(1):87, 14 pages.
Mizusawa et al., "A bacteriophage lambda vector for cloning with BamHI and Sau3A," Gene, 1982, 20(3):317-322.
Nandakumar et al., "How an RNA Ligase Discriminates RNA versus DNA Damage," Molecular Cell, 2004, 16:211-221.
Ng et al., "Gene identification signature (GIS) analysis for tanscriptome characterization and genome annotation," Nature Methods, 2005, 2(2):105-111.
Nowak et al., "Entering the Postgenome Era," Science, 1995, 270(5235):368-71.
PCT International Preliminary Report on Patentability in International Appln. No. PCT/US2019/048434, dated Mar. 2, 2021, 15 pages.
PCT International Search Report and Written Opinion in International Appln. No. PCT/US2020/066720, dated Mar. 22, 2021, 13 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Polsky-Cynkin et al., "Use of DNA immobilized on plastic and agarose supports to detect DNA by sandwich hybridization," Clin. Chem., 1985, 31(9):1438-1443.
U.S. Appl. No. 61/267,363, filed Dec. 7, 2009, 33 pages.
Ranki et al., "Sandwich hvbridization as a convenient method for the detection of nucleic acids in crude samples," Gene, 1983, 21(1-2):77-85.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy el al., "Assessing long-distance RNA sequence connectivity via RNA-templated DNA-DNA ligation," eLife, 2015, 4:e03700, 21 pages.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Shelbourne et al., "Fast copper-free click DNA ligation by the ring-strain promoted alkyne-azide cycloaddition reaction," Chem. Commun., 2011, 47(22):6257-6259.
Shendure el al., "Accurate multiplex polony sequencing of an evolved bacterial genome," Science, 2005, 309(5741):1728-1732.
Spitale et al., "Structural imprints in vivo decode RNA regulatory mechanisms," Nature, 2015, 519(7544):486-90.
Stahl et al., "Visualization and analysis of gene expression in tissue sections bv spatial transcriptomics," Science, Jun. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Strell et al., "Placing RNA in context and space—methods for spatiallv resolved transcriptomics," The FEBS Journal, 2019, 286(81):1468-1481.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-tenninal cysteines for labeling and conjugation," Angewandte Chemie International Edition, Jun. 2002, 41(12):2171-4.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Velculescu et al., "Serial analysis of gene expression," Science, Oct. 1995, 270(5235):484-7.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "High-fidelity mRNA amplification for gene profiling," Nature Biotechnology, Apr. 2000, 18(4):457-459.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Yin et al., "Genetically encoded short peptide tag for versatile protein labeling by Sfp phosphopantetheinyl transferase," PNAS, 2005, 102(44):15815-20.

(56) References Cited

OTHER PUBLICATIONS

Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling bv Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Hayes et al., "Electrophoresis of proteins and nucleic acids: I-Theory," BMJ, Sep. 1989, 299(6703):843-6.
Grokhovsky, "Specificity of DNA cleavage by ultrasound," Molecular Biology, 2006, 40(2):276-283.
Macosko et al., "Highly Parallel Genome-wide Expression Profiling of Individual Cells Using Nanoliter Droplets," Cell, 2015, 161:1202-1214.
Schweitzer et al., "Multiplexed protein profiling on microanays by rolling-circle amplification," Nature Biotechnology, Apr. 2002, 20(4):359-365.
Fu et al., "Repeat subtraction-mediated sequence capture from a complex genome," Plant J., Jun. 2010, 62(5):898-909.
Ganguli et al., "Pixelated spatial gene expression analysis from tissue," Nat Commun., Jan. 2018, 9(1):202, 9 pages.
Hahnke el al., "Striptease on glass: validation of an improved stripping procedure for in situ microarrays," J Biotechnol., Jan. 2007, 128(1):1-13
Hu et al., "High reproducibility using sodium hydroxide-stripped long oligonucleotide DNA microarrays," Biotechniques, Jan. 2005, 38(1):121-4.
Lee et al., "Improving the efficiency of genomic loci capture using oligonucleotide arrays for high throughput resequencing," BMC Genomics, Dec. 2009, 10:646, 12 pages.
[No Author Listed], "Microarray technologies have excellent possibilities in genomics-related researches," Science Tools From Amersham Pharmacia Biotech, 1998, 3(4): 8 pages (with English Translation).
Adessi et al., "Solid phase DNA amplification: characterisation of primer attachment and amplification mechanisms," Nucl. Acids Res., 2000, 28(20):E87, 8 pages.
Blanchard et al., "High-density oligonucleotide arrays," Biosensors & Bioelectronics, 1996, 11(6-7):687-690.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Gloor, "Gene targeting in *Drosophila*," Methods Mol Biol., 2004, 260:97-114.
Gotyshin et al., "Tn5 in vitro transposition," J Biol Chem., Mar. 1998, 273(13):7367-74.
Ichikawa et al., "In vitro transposition of transposon Tn3," J Biol. Chem., Nov. 1990, 265(31):18829-32, Abstract.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Kwok, "High-throughput genotyping assay approaches," Phannocogenomics, Feb. 2000, 1(1):95-100.
Lampe et al. "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Lundin et al., "Increased throughput by parallelizatino of library preparation for massive sequening," PLoS One, Apr. 2010, 5(4):e10029, 7 pages.
Merritt, et al., "Multiplex digital spatial profilin gof proteins and RNA in fixed tissue," Nat Biotechnol, May 2020, 38(5):586-599.
Mitra et al., "Digital genotyping and haplotyping with polymerase colonies," Proc. Natl. Acad, Sci. USA, May 2003, 100(10):5926-5931.
Motea et al., "Terminal deoxynucleotidyl transferase: the story of a misguided DNA polymerase," Biochim Brophys Acta., May 2010, 1804(5):1151-66.
Ohtsubo et al., "Bacterial insertion sequences," Curr Top Microbiol Immunol., 1996, 204:1-26.
Pandey et al., "Inhibition of terminal deoxynucleotidyl transferase by adenine dinucleotides. Unique inhibitory action of ApA," FEBS Lett., Mar. 1987, 213(1):204-8.
Pemov et al., "DNA analysis with multiplex microarray-enhanced PCR," Nucl. Acids Res., Jan. 2005, 33(2):e11, 9 pages.
Picelli et al., "Tn5 transposase and tagmentation procedures for massively scaled sequencing projects," Genome Res., Dec. 2014, 24(12):2033-40.
Plasterk, "The Tc1/mariner transposon family," Curr Top Microbiol Immunol., 1996, 204:125-43.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Stroh et al., "Quantum dots spectrally distinguish multiple species within the tumor milieu in vivo," Nat Med., Jun. 2005, 11(6):678-82.
Wang et al., "Concentration gradient generation methods based on microfluidic systems," RSC Adv., 2017, 7:29966-29984.
Weimeich et al., "Evidence that the cis Preference of the Tn5 Transposase is Caused by Nonproductive Multimerization," Genes and Development, Oct. 1994, 8(19):2363-2374.
Wilson et al., "New transposon delivery plasmids for insertional mutagenesis in Bacillus anthracis," J Microbiol Methods, Dec. 2007, 71(3):332-5.
[No Author Listed], "Chromium Next GEM Single Cell 3' Reagant Kits v3.1," User Guide, Document No. CG000204, 10x Genomics, Nov. 2019, 58 pages.
Bartosovic et al., "Single-cell CUT&Tag profiles histone modifications and transcription factors in complex tissues," Nat Biotechnol., Jul. 2021, 39(7):825-835, Abstract.
Chen et al., "Spatial Transcriptomics and In Situ Sequencing to Study Alzheimer's Disease," Cell, Aug. 2020, 182(4):976-991.
Deng et al., "Spatial Epigenome Sequencing at Tissue Scale and Cellular Level," BioRxiv, Mar. 2021, 40 pages.
Kaya-Okur et al., "CUT&Tag for efficient epigenomic profiling of small samples and single cells," Apr. 2019, 10(1):1930, 10 pages.
Meers et al., "Improved CUT&RUN chromatin profiling tools," Elife, Jun. 2019, 8:e46314, 16 pages.
Skene et al., "An efficient targeted nuclease strategy for high-resolution mapping of DNA binding sites," Elfie, Jan. 2017, 6:e21856, 35 pages.
Wang, "RNA amplifications for successful gene profiling analysis," J Transl Med., Jul. 2005, 3:28, 11 pages.
Alam, "Proximity Ligation Assay (PLA)," Curr Protoc Immunol., Nov. 2018, 123(1):e58, 8 pages.
Li el al., "An activity-dependent proximity ligation platform for spatially resolved quantification of active enzymes in single cells," Nat Commun. Nov. 2017, 8(1):1775, 12 pages.

(56) References Cited

OTHER PUBLICATIONS

Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Wang et al., "Imaging-based pooled CRISPR screening reveals regulators of lncRNA localization," Proc Natl Acad Sci USA, May 2019, 116(22):10842-10851.
Wiedmann et al., "Ligase chain reaction (LCR)—overview and applications," PCR Methods Appl., Feb. 1994, 3(4):S51-64.
U.S. Appl. No. 61/267,363, filed Dec. 7, 2009, Fan et al.
[No Author Listed], "HuSNP Mapping Assay User's Manual," Affymetrix Part No. 90094 (Affymetric, Santa Clara, Calif.), GeneChip, 2000, 104 pages.
[No Author Listed], "PROSEEK® Multiplex 96±96 User Manual," Olink Proteomics, Olink Bioscience, Uppsala, Sweden, 2017, 20 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007I57592b65b2cdc7130990/CG000239_VisiumSpatialGeneExpression_UserGuide_RevD.pdf>, 70 pages.
10xGenomics.com, [online],"Visium Spatial Gene Expression Reagent Kits—Tissue Optimization—User Guide," Jul. 2020, retrieved on May 25, 2021, retrieved from URL<https://assets.ctfassets.net/an68ira79xiti/5UJrN0cH17rEk0UXwd19It/e54d99fb08a8f1500aba503005a04a56/CG000238_VisiumSpatialTissueOptimizationUserGuide_RevD.pdf>, 43 pages.
Adiconis et al., "Comparative analysis of RNA sequencing methods for degraded or low-input samples," Nat Methods, Jul. 2013, 10(7):623-9.
Andresen et al., "Helicase-dependent amplification: use in OnCbip amplification and potential for point-of-care diagnostics," Expert Rev Mol Diagn., Oct. 2009. 9(7):645-650.
Archer et al., "Selective and flexible depletion of problematic sequences from RNA-seq libraries at the cDNA stage," BMC Genomics, May 2014, 15(1):401, 9 pages.
Beattie et al., "Advances ingenosensor research." Clin Chem., May 1995, 41(5):700-6.
Bolognesi el al., "Multiplex Staining by Sequential Immunostaining and Antibody Removal on Routine Tissue Sections," J. Histochem. Cytochem., Aug. 2017, 65(8):431-444.
Brow, "35—The Cleavase I enzyme for mutation and polymorphism scanning," PCR Applications Protocols for Functional Genomics, 1999, pp. 537-550.
Chen et al., "Nanoscale imaging of RNA with expansion microscopy," Nat Methods, Aug. 2016, 13(8):679-84.
Chen et al., "RNA imaging. Spatially resolved, highly multiplexed RNA profiling in single cells," Science, Apr. 2015, 348(6233):aaa6090, 21 pages.
Chen et al., "µCB-seq: microfluidic cell barcoding and sequencing for high-resolution imaging and sequencing of single cells," Lab Chip, Nov. 2020, 20(21):3899-3913.
Chrisey et al., "Covalent attachment of synthetic DNA to self-assembled monolayer films," Nucleic Acids Res., Aug. 1996, 24(15):3031-9.
Deamer et al.. "Characterization of nucleic acids bv nanopore analysis," Acc Chem Res., Oct. 2002, 35(10):817-25.
Fluidigm, "Equivalence of Imaging Mass Cytometry and Immunofluorescence on FFPE Tissue Sections," White Paper, 2017, 12 pages.
Fu et al., "Continuous Polony Gels for Tissue Mapping with High Resolution and RNA Capture Efficiency," bioRxiv, 2021, 20 pages.
Gao et al., "Q&A: Expansion microscopy", BMC Biology, 15: 50, 9 pages, 2017.
Gill et al., "Nucleic acid isothermal amplification technologies: a review," Nucleosides Nucleotides Nucleic Acids, Mar. 2008, 27(3):224-43.

Glass et al., "SIMPLE: a sequential immunoperoxidase labeling and erasing method," J. Histochem. Cytochem., Oct. 2009, 57(10):899-905.
Gracia Villacampa et al., "Genome-wide Spatial Expression Profiling in FFPE Tissues," bioRxiv, 2020, pp. 38 pages.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Healy, "Nanopore-based single-molecule DNA analysis," Nanomedicine (Lond), Aug. 2007, 2(4):459-81.
Ho et al., "Bacteriophage T4 RNA ligase 2 (gp24.1) exemplifies a family of RNA ligases found in all phylogenetic domains," PNAS, Oct. 2002, 99(20):12709-14.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry__Paraffin_2.pdf>, 3 pages.
Kalinka et al., "Comparison of ethylene carbonate and fonnamide as components of the hybridization mixture in FISH," Scientia Agricola, 2021, 78(4):e20190315, 5 pages.
Karmakar et al., "Organocatalytic removal of formaldehyde adducts from RNA and DNA bases," Nature Chemistry, Aug. 3, 2015, 7(9):752-758.
Kennedy-Darling et al., "Measuring the Formaldehyde Protein-DNA Cross-Link Reversal Rate," Analytical Chemistry, 2014, 86(12):5678-5681.
Kristensen et al., "High-Throughput Methods for Detection of Genetic Variation," BioTehniques, Feb. 2001, 30(2):318-332.
Lee et al., "Fluorescent: in situ sequencing (FISSEQ) of RNA for gene expression profiling in intact cells and tissues," Nature Protocols, 2015, 10(3):442-458.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Miele et al., "Mapping cis- and trans-chromatin interaction networks using chromosome conformation capture (3C)," Methods Mol Biol., 2009, 464:105-21.
Ncbi.nlm.nih.gov, [online], "Molecular Inversion Probe Assay." available on or before Oct. 14, 2014, via Internet Archive: Wayback Marchine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/technip/>, 2 pages.
Nichols et al., "RNA Ligases," Curr Protoc Mol Biol., Oct. 2008, 84(1):3.15.1-3.15.4.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Park et al., "Single cell trapping in larger microwells capable of supporting cell spreading and proliferation," Microfluid Nanofluid, 2010, 8:263-268.
PCT International Preliminary Report on Patentability in International Appln. No. PCT/EP2016/057355, dated Oct. 10, 2017, 7 pages.
PCT International Preliminary Report on Patentability in International Appln. No. PCT/US2019/048425, dated Mar. 2, 2021, 9 pages.

(56) References Cited

OTHER PUBLICATIONS

PCT International Search Report and Written Opinion in International Appln, No. PCT/US2020/066681, dated Apr. 14, 2021, 17 pages.
PCT International Search Report and Written Opinion in International Appln. No. PCT/US2021/012659, dated Apr. 16, 2021, 15 pages.
Pipenburg et al., "DNA detection using recombination proteins," PLoS Biol., Jul. 2006, 4(7):e204, 7 pages.
Pirici et ai., "Antibody elution method for multiple immunohistochemistry' on primary antibodies raised in the same species and of the same subtypem," J. Histochem. Cytochem., Jun. 2009, 57(6):567-75.
Raab et al., "Human tRNA genes function as chromatin insulators," EMBO J., Jan. 2012, 31(2):330-50.
Rodriguez et al., "APPRIS 2017: principal isoforms for multiple gene sets," Nucleic Acids Research, Jan. 2018, 46(D1):D213-217.
Shalon et al., "A DNA microarrav system for analyzing complex DNA samples using two-color fluorescent, probe hybridization," Genome Res., Jul. 1996, 6(7):639-45.
Simonis et al., "Nuclear organization of active and inactive chromatin domains uncovered bv chromosome conformation capture-on-chip (4C)," Nat Genet., Nov. 2006, 38(11):1348-54.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Trejo et al., "Extraction-free whole tianscriptome gene expression analysis of FFPE sections and histology-directed subareas of tissue," PLoS ONE, Feb. 2019, 14(2):e0212031, 22 pages.
Twyman et al., "Techniques Patents for SNP Genotyping," Pharmacogenomics, Jan. 2003, 4(1):67-79.
Vandernoot et al., "cDNA normalization by hvdroxvapatite chromatography to enrich transcriptome diversity in RNA-seq applications," Biotechniques, Dec. 2012, 53(6):373-80.
Vasiliskov et al., "Fabrication of mic roarray of gel-immobilized compounds on a chip bv copolymerization," Biotechniques, Sep. 1999, 27(3):592-606.
Vickovic et al., "High-definition spatial transcriptomics for in situ tissue profiling," Nature Methods, 2019, 9 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vlassakis et al., "Effect of Polymer Hydration State on In-Gel Immunoassays," Anal Chem., Nov. 2015, 87(21):11030-8.
Wu et al., "Detection DNA Point Mutation with Rolling-Circle Amplification Chip," IEEE, 2010 4th International Conference on Bioinformatics and Biomedical Engineering, Jun. 2010, 4 pages.
Yeakley et al., "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Zhang et al., "Archaeal RNA ligase from thermoccocus kodakarensis for template dependent ligation," RNA Biol., Jan. 2017, 14(1):36-44.
U.S. Appl. No. 16/876,913, US-2020-0277663-A1, filed May 18, 2020, Eswar Prasad Ramachandran Iyer.
U.S. Appl. No. 16/876,947, US-2020-0277664-A1, filed May 18, 2020, Lucas Frenz.
U.S. Appl. No. 16/876,682, US-2020-0407781-A1, filed May 18, 2020, Michael Schnall-Levin.
U.S. Appl. No. 16/876,709, US-2021-0010070-A1, filed May 18, 2020, Michael Schnall-Levin.
U.S. Appl. No. 17/073,242, US-2021-0140982-A1, filed Oct. 16, 2020, Cedric Uytingco.
U.S. Appl. No. 17/100,106, US-2021-0199660-A1, filed Nov. 20, 2020, Stephen R. Williams.
U.S. Appl. No. 17/312,375, filed Jun. 9, 2021, Cedric Uytingco.
U.S. Appl. No. 17/172,926, US-2021-0189475-A1, filed Feb. 10, 2021, Augusto Manuel Tentori.
U.S. Appl. No. 17/312,247, filed Jun. 9, 2021, Michael Schnall-Levin.
U.S. Appl. No. 17/216,681, filed Mar. 25, 2021, Yifeng Yin.
U.S. Appl. No. 17/220,529, filed Apr. 1, 2021, James Michael Chell.
[No Author Listed], "Chromium Next GEM Single Cell 3' Reagent Kits v3.1 (Dual Index)—User Guide," lOx Genomics, Mar. 2021, Document No. CG000315, 61 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxirSw51ee9/6a2ac61cf6388a72564eeb96bc294967/CG000238_VisiumSpatialTissueOptimizationUserGuide_Rev_A.pdf>, 46 pages.
10xGenomics.com, [online]," Visivm Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfHSRWpdlbFVhalpexR/8baa08d9007157592b65b2cdc7130990/CG000239_VisiumSpatialGeneExpression_UserGuide_RevD.pdf>, 70 pages.
Aran et al., "xCell: digitally portraying the tissue cellular heterogeneity landscape," Genome Biol., Nov. 2017, 18(1):220, 14 pages.
Asp et al., "Spatially Resolved Transcriptomes-Next Generation Tools for Tissue Exploration," Bioessays, Oct. 2020, 42(10):e1900221, 16 pages.
Balakrishnan et al., "Flap endonuclease 1," Annu Rev Biochem., Jun. 2013, 82:119-138.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Blair et al., "Microarray temperature optimization using hybridization kinetics," Methods Mol Biol., 2009, 529:171-96.
Blanco et al., "A practical approach to FRET-based PNA fluorescence in situ hybridization," Methods, Dec. 2010, 52(4):343-51.
Bolotin et al., "MiXCR: software for comprehensive adaptive immunity profiling." Nat Methods., May 2015, 12(5):380-1.
Chen et al., "Parallel single nucleotide polymorphism genotyping by surface invasive cleavage with universal detection," Anal Chem., Apr. 2005, 77(8):2400-5.
Chester et al., "Dimethyl sulfoxide-mediated primer Tm reduction: a method for analyzing the role of renaturation temperature in the polymerase drain reaction," Anal Biochem, Mar. 1993, 209(2):284-90.
Ciaccio et al., "Systems analysis of EGF receptor signaling dynamics with microwestern arrays," Nat Methods, Feb. 2010, 7(2):148-55.
Cruz et al., "Methylation in cell-free DNA for early cancer detection," Ann Oncol., Jun. 2018, 29(6):1351-1353.
Czarnik, "Encodingmethods for combinatorial chemistry." Curr Opin Chem Biol., Jun. 1997, 1(1):60-6.
Gerard et al., "Excess dNTPs minimize RNA hydrolysis during reverse transcription," Biotechniques, Nov. 2002, 33(5):984, 986, 988, 990.

(56) References Cited

OTHER PUBLICATIONS

Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hessner et al., "Genotyping of factor V G1691A (Leiden) without the use of PCR by invasive cleavage of oligonucleotide probes," Clin Chem., Aug. 2000, 46(8 Pt 1):1051-6.
Hoffman et al., "Formaldehyde crosslinking: a tool for the study of chromatin complexes." J Biol Chem., Oct. 2015, 290(44):26404-11.
Hughes et al., "Microfluidic Western blotting," PNAS, Dec. 2012, 109(52):21450-21455.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jucá et al., "Effect of dimethyl sulfoxide on reverse transcriptase activity," Braz. J. Med. Biol. Res., Mar. 1995, 28(3)285-90.
Kalantari et al., "Deparaffinization of formalin-fixed paraffin-embedded tissue blocks using hot water instead of xylene," Anal Biochem., Aug. 2016, 507:71-3.
Ke et al., "In situ sequencing for RNA analysis in preserved tissue and cells," Nat Methods., Sep. 2013, Supplementary Materials, 29 pages.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by cblorella virus DNA ligase and a novel iLock assay with improved direct RNA detection accuracy," Nucleic Acids Research, Oct. 2017, 45(18):e161, 9 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
MacBeath et al., "Printing proteins as microarrays for high-throughput function determination," Science, Sep. 2000, 289(5485):1760-1763.
Miner et al., "Molecular barcodes delect redundancv and contamination in hairpin-bisulfite PCR," Nucleic Acids Res., Sep. 2004, 32(17):e135, 4 pages.
Morlan et al., "Selective depletion of rRNA enables whole transcriptome profiling of archival fixed tissue," PLoS One, Aug. 2012, 7(8):e42882, 8 pages.
Niedringhaus et al., "Landscape of next-generation sequencing technologies," Anal Chem., Jun. 2011, 83(12):4327-41.
Nilsson et al., "RNA-templated DNA ligation for transcript analysis," Nucleic Acids Res., Jan. 2001, 29(2):578-81.
Olivier, "The Invader assay for SNP genotyping," Mulat. Res., Jun. 2005, 573(1-2):103-110.
Pellestor et al., "The peptide nucleic acids (PNAs), powerful tools for molecular genetics and cytogenetics," Eur J Hum Genet., Sep. 2004, 12(9):694-700.

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perocchi et al., "Antisense artifacts in transcriptome microarray experiments are resolved by actinomycin D," Nucleic Acids Res., 2007, 35(19):e128, 7 pages.
Picelli et al., "Full-length RNA-seq from single cells using Smart-seq2," Nat Protoc., Jan. 2014, 9(1):171-81.
Plongthongkum et al., "Advances in the profiling of DNA modifications: cytosine methylation and beyond," Nature Reviews Genetics, Aug. 2014, 15(10):647-661.
Qiu et al., "Combination probes with intercalating anchors and proximal fluorophores for DNA and RNA detection," Nucleic Acids Research, Sep. 2016, 44(17):e138, 12 pages.
Salmén et al., "Barcoded solid-phase RNA capture for Spatial Transcriptomics profiling in mammalian tissue sections," Nature Protocols, Oct. 2018, 13(11):2501-2534.
Schouten et al., "Relative quantification of 40 nucleic acid sequences by multiplex ligation-dependent probe amplificaiton," Nucleic Acids Res., Jun. 2002, 30(12):e57, 13 pages.
Schwers et al., "A high-sensitivity, medium-density, and target amplification-free planar waveguide microanay system for gene expression analysis of formalin-fixed and paraffin-embedded tissue," Clin. Chem., Nov. 2009, 55(11):4995-2003.
Singh et al., "High-throughput targeted long-read single cell sequencing reveals the clonal and transcriptional landscape of lymphocytes," Nat. Commun., Jul. 2019, 10(1):3120, 13 pages.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Sutherland et al.. "Utility of formaldehyde cross-linking and mass spectrometry in the study of proteinprotein interactions," J. Mass Spectrom., Jun. 2008, 43(6):699-715.
Toubanaki et al., "Dry-reagent disposable biosensor for visual genotyping of single nucleotide polymorphisms by oligonucleotide ligation reaction: application to phannacogenetic analysis," Hum Mutat., Aug. 2008, 29(8):1071-8.
Tu et al., "TCR sequencing paired with massively parallel 3' RNA-seq reveals clonotypic T cell signatures," Nature Immunology, Dec. 2019, 20(12):1692-1699.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Wang et al., "Tagmentation-based whole-genome bisulfite sequencing," Nature Protocols, Oct. 2013, 8(10):2022-2032.
Wu et al.. "RollFISH achieves robust quantification of single-molecule RNA biomarkers in paraffin-embedded tumor tissue samples," Commun BioL, Nov. 2018, 1:209, 8 pages.
Yasukawa et al., "Effects of organic solvents on the reverse transcription reaction catalyzed by reverse transcriptases from avian myeloblastosis virus and Moloney murine leukemia virus." Biosci Bioteclmoi Biochem., 2010, 74(9):1925-30.
Zhao et al., "Isothermal Amplification of Nucleic Acids," Chemical Reviews, Nov. 2015, 115(22):12491-12545.

\* cited by examiner

Grp88

Low High
Expression Level

Penk

Low High
Expression Level

Plp1
Low High
Expression Level

Nptrx

Low ──────────── High
Expression Level

Mbp2

Low ──────────── High
Expression Level

All specific LHS+RHS probes
Low — High
Expression Level

Grp88
Low — High
Expression Level

Penk
Low — High
Expression Level

Plp1
Low — High
Expression Level

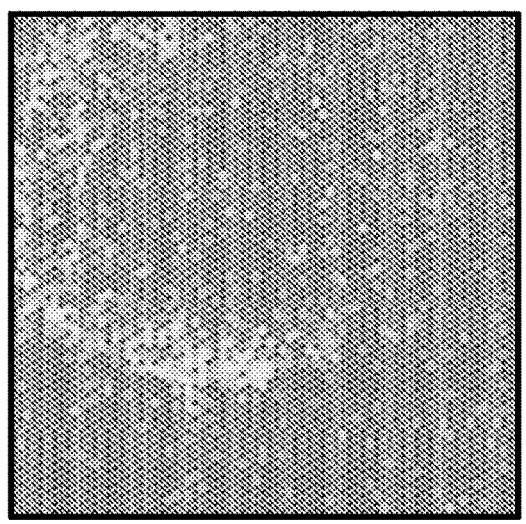
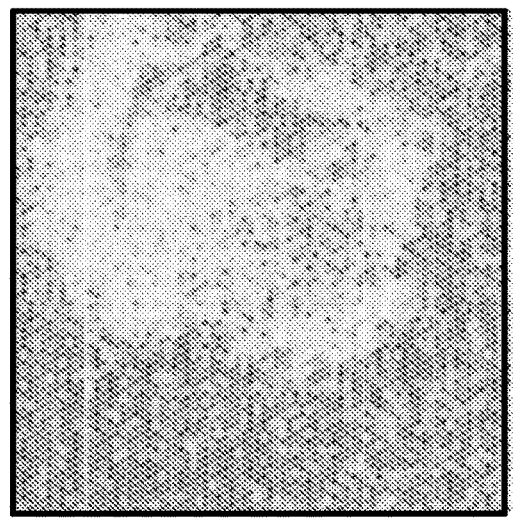
Nptrx
Low　　　　　High
Expression Level
FIG. 19E
Mbp2
Low　　　　　High
Expression Level
FIG. 19F

1 RTL 1
2 RTL 2
3 RTL 80C decross
4 RTL ProK pre-hyb
5 Fresh control

ERBB2 / HER2

METHODS FOR SPATIAL ANALYSIS USING RNA-TEMPLATED LIGATION

CROSS-REFERENCE TO RELATED APPLICATIONS

Pursuant to 35 U.S.C. § 119(e), this application is a continuation of International Application PCT/US2020/066720, with an international filing date of Dec. 22, 2020, which claims the benefit to U.S. Provisional Patent Application No. 62/952,736, filed Dec. 23, 2019; U.S. Provisional Patent Application No. 62/969,458, filed Feb. 3, 2020; U.S. Provisional Patent Application No. 63/087,061, filed Oct. 2, 2020; and U.S. Provisional Patent Application No. 63/108,088, filed Oct. 30, 2020. The contents of each of these applications are incorporated herein by reference in their entireties.

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

Generally, targeting a particular analyte in a biological sample utilizes a capture probe that targets a common transcript sequence such as a poly(A) mRNA-like tail. However, this approach is capable of detecting a high number of off target analytes. Methods such as RNA-templated ligation offer an alternative to indiscriminant capture of a common transcript sequence. See, e.g., Yeakley, *PLoS One*, 25; 12(5):e0178302 (2017), which is incorporated by reference in its entirety. However, there remains a need to develop an alternative to common transcript sequence (e.g., poly(A) mRNA-like tail) capture of target analytes that is capable of detecting an analyte(s) in an entire transcriptome while providing information regarding the spatial location and abundance of a target analyte.

SUMMARY

Targeted RNA capture is an attractive alternative to poly(A) mRNA capture in order to interrogate spatial gene expression in a sample (e.g., an FFPE tissue). Compared to poly(A) mRNA capture, targeted RNA capture as described herein is less affected by RNA degradation associated with FFPE fixation compared to methods dependent on oligo-dT capture and reverse transcription of mRNA. Further targeted RNA capture as described herein allows for sensitive measurement of specific genes of interest that otherwise might be missed with a whole transcriptomic approach. Targeted RNA capture can be used to capture a defined set of RNA molecules of interest, or it can be used at a whole transcriptome level, or anything in between. When combined with the spatial methods disclosed herein, the location and abundance of the RNA targets can be determined.

In one aspect, this disclosure features a method for determining a location of an analyte in a biological sample including: (a) providing the biological sample on an array including a plurality of capture probes, where a capture probe of the plurality includes: (i) a spatial barcode and (ii) a capture domain; (b) contacting a first probe and a second probe with the biological sample, where the first probe and the second probe each include one or more sequences that are substantially complementary to sequences of the analyte, and where the second probe includes a capture probe capture domain; (c) hybridizing the first probe and the second probe to the analyte; (d) generating a ligation product by ligating the first probe and the second probe; (e) releasing the ligated product from the analyte; (f) hybridizing the ligation product to the capture domain; and (g) determining (i) all or a part of the sequence of the ligation product bound to the capture domain, or a complement thereof, and (ii) all or a part of the sequence of the spatial barcode, or a complement thereof, and using the determined sequence of (i) and (ii) to identify the location of the analyte in the biological sample. In some instances, the methods include determining the abundance and location of the analyte in the biological sample. In some instances, the methods include determining the abundance of an analyte at a location in the biological sample.

In some embodiments, the first probe and the second probe are substantially complementary to adjacent sequences of the analyte. In some embodiments, the first probe and the second probe hybridize to sequences that are not adjacent to each other on the analyte.

In some embodiments, the method further includes hybridizing a third probe to the first probe and the second probe, where the third probe includes a first sequence that is substantially complementary to a portion of the first probe and a second sequence that is substantially complementary to a portion of the second probe. In some embodiments, hybridizing the first probe and the second probe to the analyte is performed at a first temperature. In some embodiments, hybridizing the third probe to the first probe and the second probe is performed at a second temperature. In some embodiments, the first temperature is a higher temperature than the second temperature. In some embodiments, the first temperature is from about 50° C. to about 75° C., from about 55° C. to about 70° C., or from about 60° C. to about 65° C. In some embodiments, the second temperature is from about 15° C. to about 35° C., from about 20° C. to about 30° C., or from about 25° C. to about 30° C. In some embodiments, the first probe is extended with a DNA polymerase, thereby filling in a gap between the first probe and the second probe and generating an extended first probe.

In some embodiments, the first probe includes a sequence that is substantially complementary to a first target sequence of the analyte. In some embodiments, the second probe further includes: (i) a first sequence that is substantially complementary to a second target sequence of the analyte; (ii) a linker sequence; (iii) a second sequence that is substantially complementary to a third target sequence of the analyte; and (iv) a capture probe capture domain that is capable of binding to a capture domain of a capture probe. In some embodiments, the first target sequence of the analyte is directly adjacent to the second target sequence of the analyte. In some embodiments, the second target sequence is not directly adjacent to the third target sequence on the analyte. In some embodiments, the second target sequence and the third target sequence are (i) on different exons of the analyte or (ii) located within the same exon of the analyte but are not adjacent on the analyte.

In some embodiments, the second probe includes a sequence that is substantially complementary to a third target sequence of the analyte. In some embodiments, the first probe includes: (i) a first sequence that is substantially complementary to a first target sequence of the analyte; (ii) a linker sequence; and (iii) second sequence that is substantially complementary to second target sequence of the analyte. In some embodiments, the second target sequence is directly adjacent to the third target sequence. In some embodiments, the first target sequence is not directly adjacent to the second target sequence on the analyte. In some embodiments, the first target sequence and second target sequence are (i) on different exons of the analyte or (ii) located within the same exon but are not directly adjacent on the analyte.

In some embodiments, the linker sequence includes a total of about 1 nucleotide to about 100 nucleotides. In some embodiments, the linker further includes a barcode sequence that serves as a proxy for identifying the analyte.

In some embodiments, the first probe includes at least two ribonucleic acid bases at the 3' end, and where the second probe includes a phosphorylated nucleotide at the 5' end.

In some embodiments, generating a ligation product includes ligating (i) the first probe to the second probe or (ii) the extended first probe to the second probe using enzymatic ligation or chemical ligation, where the enzymatic ligation utilizes a ligase. In some embodiments, the ligase is one or more of a T4 RNA ligase (Rnl2), a splintR ligase, a single stranded DNA ligase, or a T4 DNA ligase.

In some embodiments, the second probe includes a pre-adenylated phosphate group at its 5' end, and where the first probe includes at least two ribonucleic acid bases at the 3' end. In some embodiments, the step of generating a ligation product includes ligating a 3' end of the first probe to the 5' end of the second probe using a ligase that does not require adenosine triphosphate for ligase activity. In some embodiments, the ligase is selected from the group consisting of: thermostable 5' AppDNA/RNA Ligase, truncated T4 RNA Ligase 2, truncated T4 RNA Ligase 2 K227Q, truncated T4 RNA Ligase 2 KQ, *Chlorella* Virus PBCV-1 DNA Ligase, or any combination thereof.

In some embodiments, the first probe further includes a functional sequence, where the functional sequence is a primer sequence.

In some embodiments, the method further includes providing a capture probe capture domain blocking moiety that interacts with the capture probe capture domain. In some embodiments, the method further includes releasing the capture probe capture domain blocking moiety from the capture probe capture domain prior to step (f). In some embodiments, the capture probe capture domain includes a poly-adenylated (poly(A)) sequence or a complement thereof. In some embodiments, the capture probe capture domain blocking moiety includes a poly-uridine sequence, a poly-thymidine sequence, or both. In some embodiments, releasing the poly-uridine sequence from the poly(A) sequence includes denaturing the ligation product or contacting the ligation product with an endonuclease, exonuclease or ribonuclease. In some embodiments, the capture probe capture domain includes a sequence that is complementary to all or a portion of the capture domain of the capture probe. In some embodiments, the capture probe capture domain includes a degenerate sequence.

In some embodiments, the first probe and/or the second probe is a DNA probe.

In some embodiments, the third probe is a DNA probe.

In some embodiments, the capture probe capture domain blocking moiety is a DNA probe.

In some embodiments, the releasing step (f) includes removing the ligated probe from the analyte.

In some embodiments, the releasing of (i) the ligation product from the analyte or (ii) the capture probe capture domain blocking moiety from the capture domain binding domain, includes contacting the ligated probe with an endoribonuclease. In some embodiments, the endoribonuclease is one or more of RNase H, RNase A, RNase C, or RNase I. In some embodiments, the RNase H includes RNase H1, RNase H2, or RNase H1 and RNase H2.

In some embodiments, the biological sample is a tissue sample. In some embodiments, the tissue sample is a formalin-fixed, paraffin-embedded (FFPE) tissue sample, a fresh or a frozen tissue sample. In some embodiments, the tissue sample is the FFPE tissue sample, and the tissue sample is decrosslinked. In some embodiments, the biological sample was previously stained. In some embodiments, the biological sample was previously stained using immunofluorescence or immunohistochemistry. In some embodiments, the biological sample was previously stained using hematoxylin and eosin.

In some embodiments, the method further includes contacting the biological sample with a permeabilization agent, where the permeabilization agent is selected from an organic solvent, a detergent, and an enzyme, or a combination thereof. In some embodiments, the permeabilization agent is selected from the group consisting of: an endopeptidase, a protease sodium dodecyl sulfate (SDS), polyethylene glycol tert-octylphenyl ether, polysorbate 80, and polysorbate 20, N-lauroylsarcosine sodium salt solution, saponin, Triton X-100™, and Tween-20™. In some embodiments, the endopeptidase is pepsin or proteinase K.

In some embodiments, the method further includes, prior to step (a), fixing the biological sample. In some embodiments, the step of fixing the biological sample is performed using one or both of methanol and acetone.

In some embodiments, the analyte includes RNA. In some embodiments, the RNA is an mRNA.

In some embodiments, the determining step includes amplifying all or part of the ligation product specifically bound to the capture domain. In some embodiments, an amplifying product includes (i) all or part of sequence of the ligation product specifically bound to the capture domain, or a complement thereof, and (ii) all or a part of the sequence of the spatial barcode, or a complement thereof. In some embodiments, the determining step includes sequencing. In some embodiments, the sequencing step includes in situ sequencing, Sanger sequencing methods, next-generation sequencing methods, and nanopore sequencing.

In another aspect, this disclosure features a kit including: (a) a substrate including a plurality of capture probes including a spatial barcode and a capture domain; (b) a system including: a plurality of first probes and second probes, where a first probe and a second probe each includes sequences that are substantially complementary to an analyte, and where the second probe includes a capture binding domain; and (c) instructions for performing the method of any one of the preceding claims.

In another aspect, this disclosure features a kit including: (a) an array including a plurality of capture probes; (b) a plurality of probes including a first probe and a second, where the first probe and the second probe are substantially complementary to adjacent sequences of an analyte, where the second probe includes (i) a capture probe capture domain that is capable of binding to a capture domain of the capture probe and (ii) a linker sequence; (c) a plurality of enzymes including a ribonuclease and a ligase; and (d) instructions for performing the method of any one of the preceding claims.

In another aspect, this disclosure features a kit including: (a) an array including a plurality of capture probes; (b) a plurality of probes including a first probe and a second probe, where the first probe and the second probe are substantially complementary to adjacent sequences of an analyte, where the first probe includes a linker sequence, where the second probe includes a capture probe capture domain that is capable of binding to a capture domain of the capture probe; (c) a plurality of enzymes including a ribonuclease and a ligase; and (d) instructions for performing the method of any one of the preceding claims.

In some embodiments, the kit includes a second probe including a preadenylated phosphate group at its 5' end, and a ligase that does not require adenosine triphosphate for ligase activity.

In another aspect, this disclosure features a composition including a spatial array including capture probes, where the capture probes include a spatial barcode and a capture domain, a biological sample on the spatial array where the biological sample includes a plurality of analytes of interest, a first probe oligonucleotide and a second probe oligonucleotide hybridized to an analyte and ligated together, where the first probe oligonucleotide and the second probe oligonucleotide each include a sequence that is substantially complementary to adjacent sequences of the analyte and where one of the first probe or the second probe includes a capture probe capture domain.

In some embodiments, the composition further includes an RNase H enzyme. In some embodiments, the composition further includes a ligase. In some embodiments, the probe oligonucleotide that does not include a capture probe capture domain includes a functional domain.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B".

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

BRIEF DESCRIPTION OF THE DRAWINGS

The following drawings illustrate certain embodiments of the features and advantages of this disclosure. These embodiments are not intended to limit the scope of the appended claims in any manner. Like reference symbols in the drawings indicate like elements.

FIG. 12A illustrates formation of a triazole bond. FIG. 12B illustrates formation of a phosphorothioate bond. FIG. 12C illustrates formation of an amide bond. FIG. 12D illustrates a formation of phosphoramidate bond. FIG. 12E illustrates a conjugation reaction.

FIGS. 19A-19F show gene expression patterns in mouse brain tissue using total probe oligonucleotide counts (FIG. 19A) and gene-specific probe oligonucleotide (FIGS. 19B-19F).

DETAILED DESCRIPTION

Figure 1:
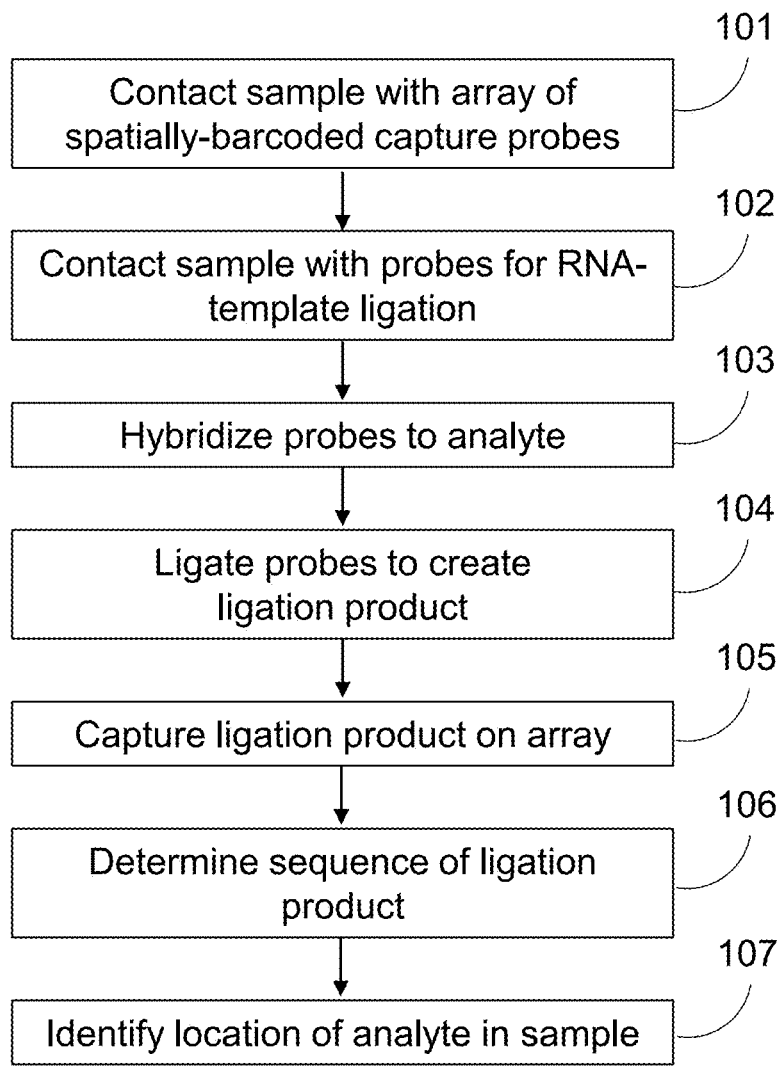
FIG. 1 shows an exemplary spatial analysis workflow.

Targeted RNA capture is an attractive alternative to poly (A) mRNA capture in order to interrogate spatial gene expression in FFPE tissue. Compared to poly(A) mRNA capture, targeted RNA capture is less affected by RNA degradation associated with FFPE fixation than methods dependent on oligo-dT capture and reverse transcription of mRNA; allows for sensitive measurement of specific genes of interest that otherwise might be missed with a whole transcriptomic approach; and is scalable, with demonstrated probes targeting a large fraction of the transcriptome.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., WO 2020/176788 and/or U.S. Patent Application Publication No. 2020/0277663. Generation of capture probes can be achieved by any appropriate method, including those described in WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in WO 2020/176788 and/or U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). In some instances, the spatially-barcoded array populated with capture probes (as described further herein) is contacted with a biological sample, and the biological sample is permeabilized, allowing the analyte to migrate away from the sample and toward the array. The analyte interacts with a capture probe on the spatially-barcoded array. Another method is to cleave spatially-barcoded capture probes from an array and promote the spatially-barcoded capture probes towards and/or into or onto the biological sample. In some instances, the spatially-barcoded array populated with capture probes (as described further herein) can be contacted with a sample. The spatially-barcoded capture probes are cleaved and then interact with cells within the provided biological sample. The interaction can be a covalent or non-covalent cell-surface interaction. The interaction can be an intracellular interaction facilitated by a delivery system or a cell penetration peptide. Once the spatially-barcoded capture probe is associated with a particular cell, the sample can be optionally removed for analysis. The sample can be optionally dissociated before analysis. Once the tagged cell is associated with the spatially-barcoded capture probe, the capture probes can be analyzed to obtain spatially-resolved information about the tagged cell.

In some instances, sample preparation may include placing the sample on a slide, fixing the sample, and/or staining the biological sample for imaging. The stained sample can be then imaged on the array using both brightfield (to image the sample hematoxylin and eosin stain) and/or fluorescence (to image features) modalities. Optionally, the sample can be destained prior to permeabilization. In some embodiments, analytes are then released from the sample and capture probes forming the spatially-barcoded array hybridize or bind the released analytes. The sample is then removed from the array and the capture probes cleaved from the array. The biological sample and array are then optionally imaged a second time in one or both modalities while the analytes are reverse transcribed into cDNA, and an amplicon library is prepared and sequenced. Images are then spatially-overlaid in order to correlate spatially-identified biological sample information. When the sample and array are not imaged a second time, a spot coordinate file is supplied instead. The spot coordinate file replaces the second imaging step. Further, amplicon library preparation can be performed with a unique PCR adapter and sequenced.

In some instances, disclosed is another exemplary workflow that utilizes a spatially-barcoded array on a substrate, where spatially-barcoded capture probes are clustered at areas called features. The spatially-barcoded capture probes can include a cleavage domain, one or more functional domains, a spatial barcode, a unique molecular identifier, and a capture domain. The spatially-barcoded capture probes can also include a 5' end modification for reversible attachment to the substrate. The spatially-barcoded array is contacted with a biological sample, and the sample is permeabilized through application of permeabilization reagents. Permeabilization reagents may be administered by placing the array/sample assembly within a bulk solution. Alternatively, permeabilization reagents may be administered to the sample via a diffusion-resistant medium and/or a physical barrier such as a lid, wherein the sample is sandwiched between the diffusion-resistant medium and/or barrier and the array-containing substrate. The analytes are migrated toward the spatially-barcoded capture array using any number of techniques disclosed herein. For example, analyte migration can occur using a diffusion-resistant medium lid and passive migration. As another example, analyte migration can be active migration, using an electrophoretic transfer system, for example. Once the analytes are in close proximity to the spatially-barcoded capture probes, the capture probes can hybridize or otherwise bind a target analyte. The biological sample can be optionally removed from the array.

The capture probes can be optionally cleaved from the array, and the captured analytes can be spatially-barcoded by performing a reverse transcriptase first strand cDNA reaction. A first strand cDNA reaction can be optionally performed using template switching oligonucleotides. For example, a template switching oligonucleotide can hybridize to a poly(C) tail added to a 3' end of the cDNA by a reverse transcriptase enzyme in a template independent manner. The original mRNA template and template switching oligonucleotide can then be denatured from the cDNA and the spatially-barcoded capture probe can then hybridize with the cDNA and a complement of the cDNA can be generated. The first strand cDNA can then be purified and collected for downstream amplification steps. The first strand cDNA can be amplified using PCR, where the forward and reverse primers flank the spatial barcode and analyte regions of interest, generating a library associated with a particular spatial barcode. In some embodiments, the library preparation can be quantitated and/or quality controlled to verify the success of the library preparation steps. In some embodiments, the cDNA comprises a sequencing by synthesis (SBS) primer sequence. The library amplicons are sequenced and analyzed to decode spatial information.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain. In some instances, the capture probe can include functional sequences that are useful for subsequent processing. In some instances, a capture probe can be reversibly attached to a substrate via a linker. The capture probe can include one or more functional sequences, which can include a sequencer specific flow cell attachment sequence, e.g., a P5 or P7 sequence, as well as functional sequence, which can include sequencing primer sequences, e.g., a R1 primer binding site, a R2 primer binding site. In some embodiments, sequence is a P7 sequence and sequence is a R2 primer binding site. A capture probe can additionally include a spatial barcode and/or unique molecular identifier and a capture domain. The different sequences of the capture probe need not be in the sequential manner as depicted in this example, however the capture domain should be placed in a location on the barcode wherein analyte capture and extension of the capture domain to create a copy of the analyte can occur.

Figure 2:
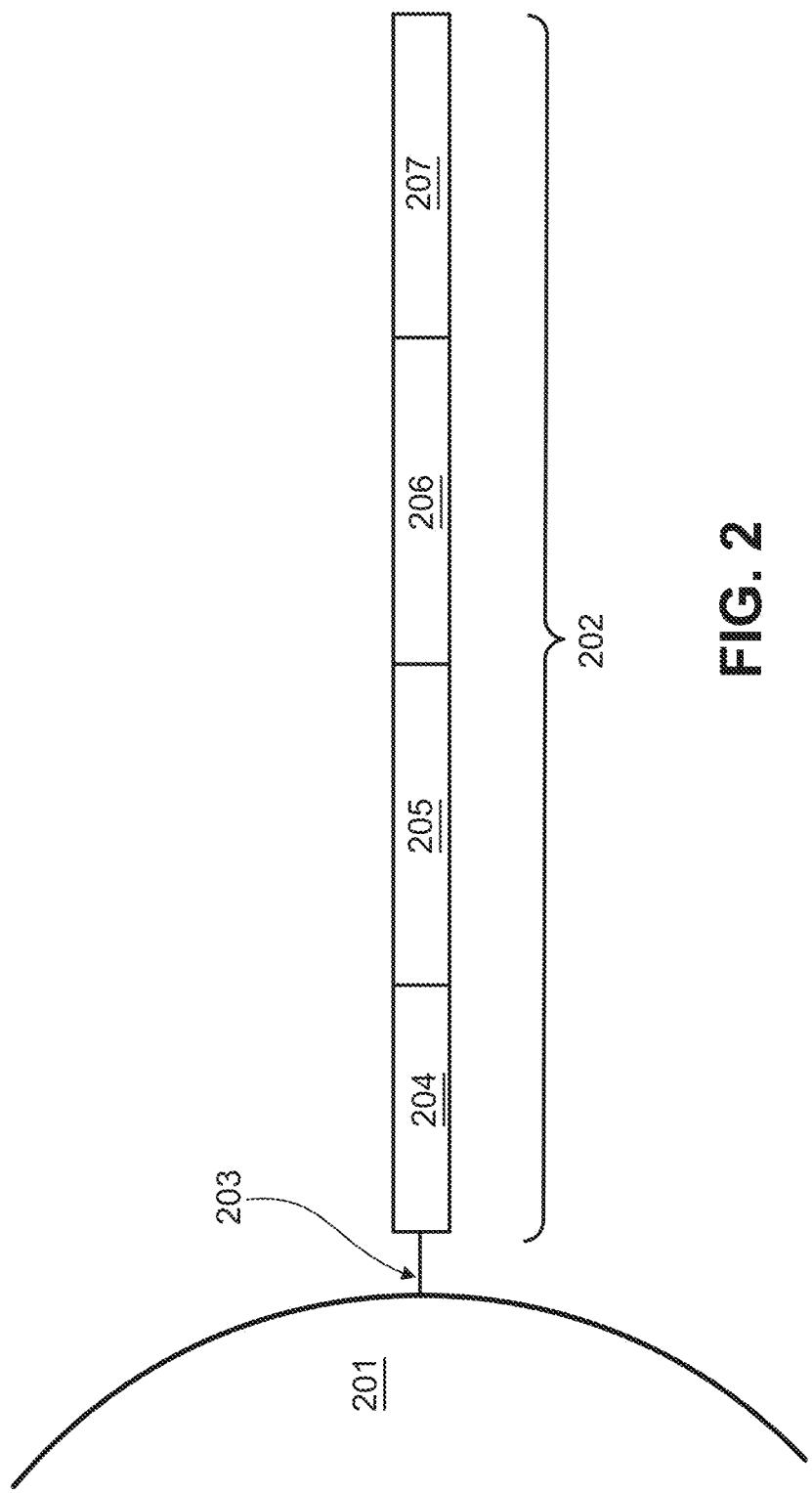
FIG. 2 is a schematic diagram showing an example of a barcoded capture probe, as described herein.

FIG. 2 is a schematic diagram showing an example of a capture probe, as described herein. As shown, the capture probe 202 is optionally coupled to a feature 201 by a cleavage domain 203, such as a disulfide linker. The capture probe can include functional sequences that are useful for subsequent processing, such as functional sequence 204, which can include a sequencer specific flow cell attachment sequence, e.g., a P5 or P7 sequence, as well as functional sequence 205, which can include sequencing primer sequences, e.g., a R1 primer binding site. In some embodiments, sequence 204 is a P7 sequence and sequence 205 is a R1 primer binding site. A spatial barcode 206 can be included within the capture probe for use in barcoding the target analyte. The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems.

In some embodiments, the spatial barcode 206, functional sequences 204 (e.g., flow cell attachment sequence) and 205 (e.g., sequencing primer sequences) can be common to all of the probes attached to a given feature. The spatial barcode can also include a capture domain 207 to facilitate capture of a target analyte.

Figure 3:
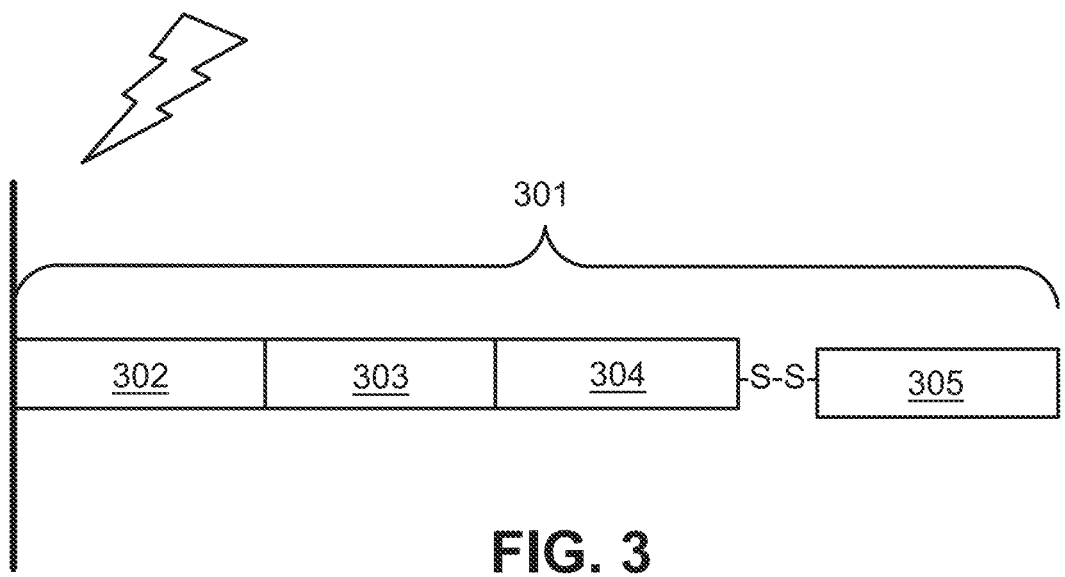
FIG. 3 is a schematic illustrating a cleavable capture probe, wherein the cleaved capture probe can enter into a non-permeabilized cell and bind to target analytes within the sample.

In some cases, capture probes are introduced into the cell using a cell-penetrating peptide. FIG. 3 is a schematic illustrating a cleavable capture probe that includes a cell-penetrating peptide, wherein the cleaved capture probe can enter into a non-permeabilized cell and bind to analytes within the sample. The capture probe 301 contains a cleavage domain 302, a cell penetrating peptide 303, a reporter molecule 304, and a disulfide bond (—S—S—). 305 represents all other parts of a capture probe, for example a spatial barcode and a capture domain.

Figure 4:
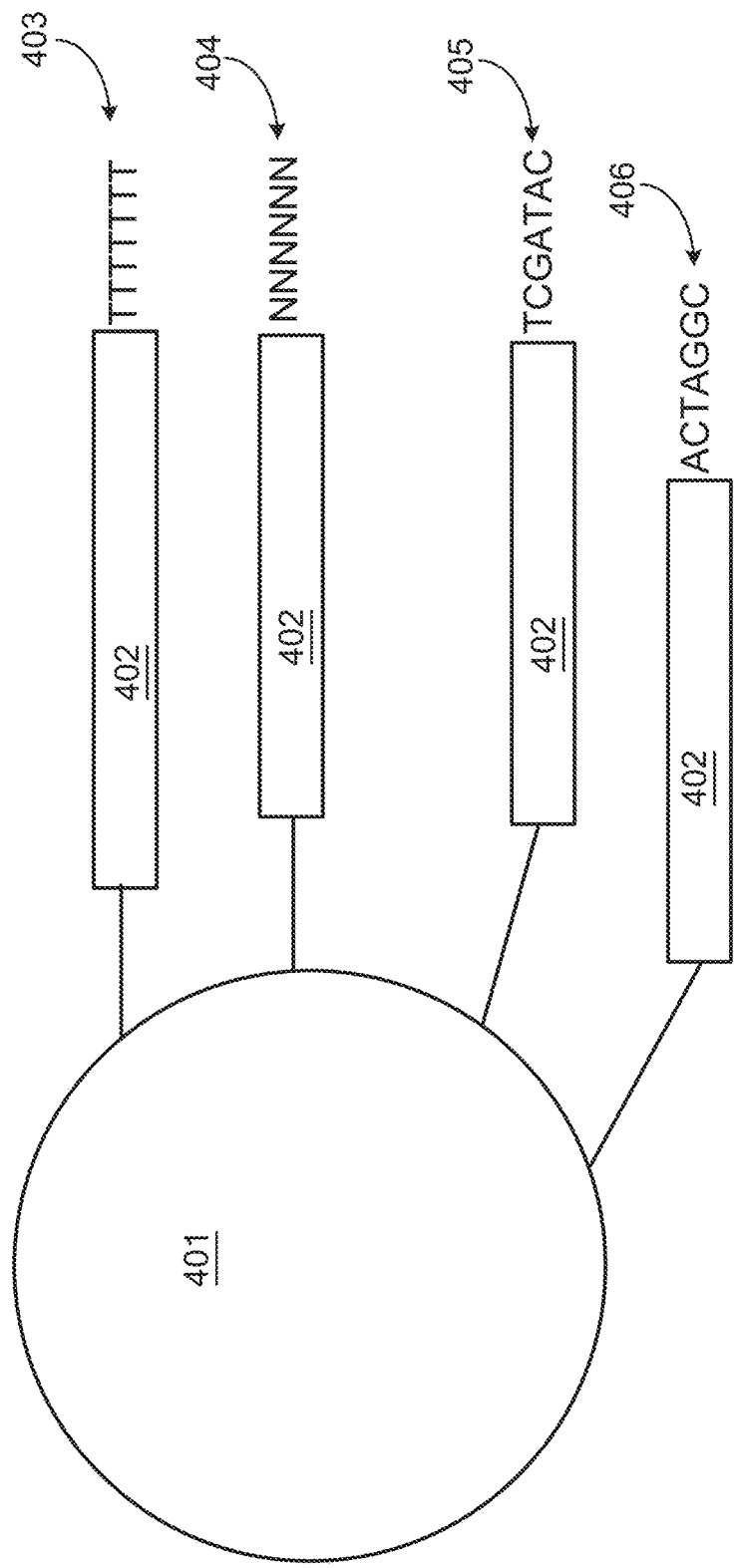
FIG. 4 is a schematic diagram of an exemplary multiplexed spatially-barcoded feature.

In some instances, the disclosure provides multiplexed spatially-barcoded features. FIG. 4 is a schematic diagram of an exemplary multiplexed spatially-barcoded feature. In FIG. 4, the feature 401 (e.g., a bead, a location on a slide or other substrate, a well on a slide or other substrate, a partition on a slide or other substrate, etc.) can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 402. One type of capture probe associated with the feature includes the spatial barcode 402 in combination with a poly(T) capture domain 403, designed to capture mRNA target analytes. A second type of capture probe associated with the feature includes the spatial barcode 402 in combination with a random N-mer capture domain 404 for gDNA analysis. A third type of capture probe associated with the feature includes the spatial barcode 402 in combination with a capture domain complementary to the analyte capture agent of interest 405. A fourth type of capture probe associated with the feature includes the spatial barcode 402 in combination with a capture probe that can specifically bind a nucleic acid molecule 406 that can function in a CRISPR assay (e.g., CRISPR/Cas9). While only four different capture probe-barcoded constructs are shown in FIG. 4, capture-probe barcoded constructs can be tailored for analyses of any given analyte associated with a nucleic acid and capable of binding with such a construct. For example, the schemes shown in FIG. 4 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents.

Additional features of capture probes are described in WO 2020/176788 and/or U.S. Patent Application Publication No. 2020/0277663, each of which is incorporated by reference in its entirety. Generation of capture probes can be achieved by any appropriate method, including those described in WO 2020/176788 and/or U.S. Patent Application Publication No. 2020/0277663, each of which is incorporated by reference in its entirety.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe. In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in WO 2020/176788 and/or U.S. Patent Application Publication No. 2020/0277663. Some quality control measures are described in WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in WO 2020/176788 and/or U.S. Patent Application Publication No. 2020/0277663. Exemplary features and geometric attributes of an array can be found in WO 2020/176788 and/or U.S. Patent Application Publication No. 2020/0277663.

Figure 5:
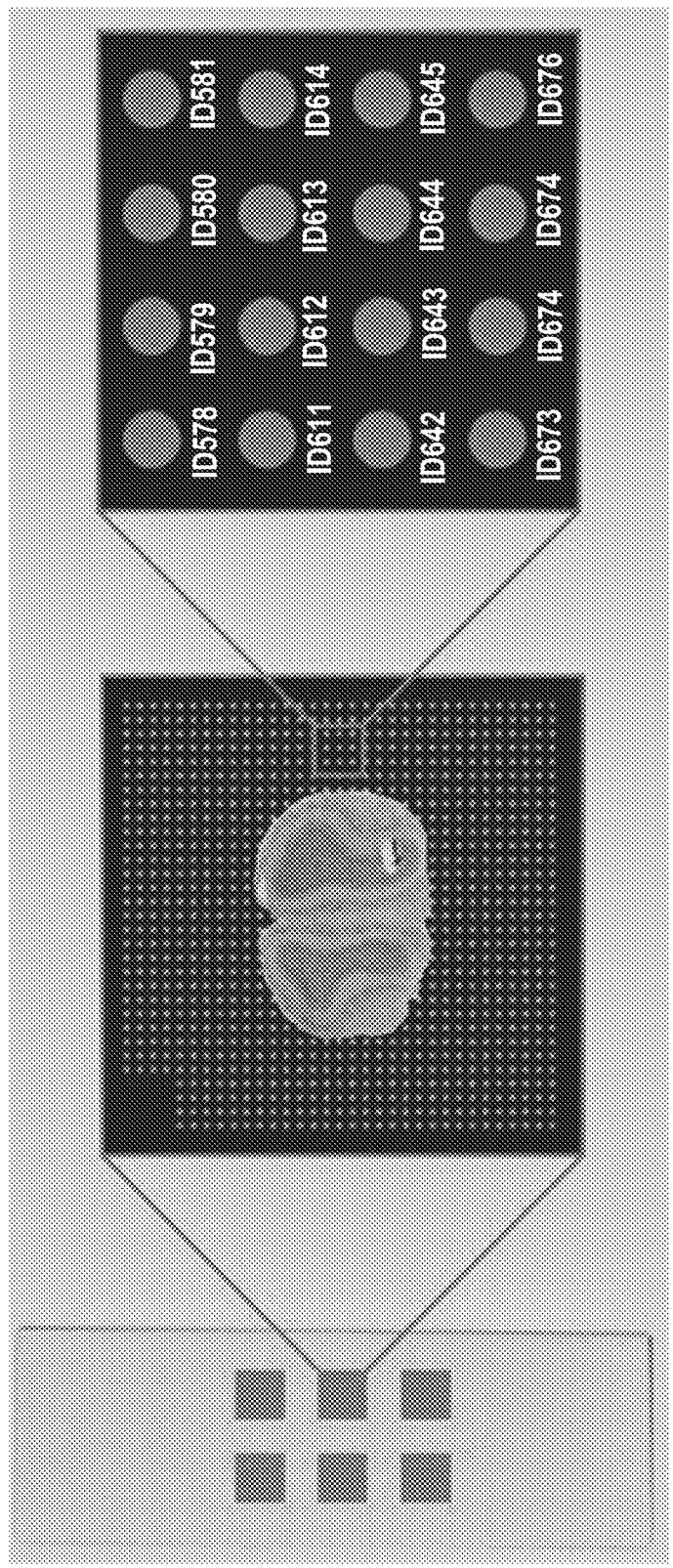
FIG. 5 is a schematic showing the exemplary arrangement of barcoded features within an array.

FIG. 5 depicts an exemplary arrangement of barcoded features within an array. From left to right, FIG. 5 shows (left) a slide including six spatially-barcoded arrays, (center)

an enlarged schematic of one of the six spatially-barcoded arrays, showing a grid of barcoded features in relation to a biological sample, and (right) an enlarged schematic of one section of an array, showing the specific identification of multiple features within the array (labelled as ID578, ID579, ID560, etc.).

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells, areas on a substrate) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in WO 2020/176788 and/or U.S. Patent Application Publication No. 2020/0277663, or any of one or more of the devices or methods described in WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

I. RNA Capture Using RNA-Templated Ligation (A) General Background

Although techniques such as whole genome sequencing and whole exome sequencing are available, these techniques have drawbacks in that they provide a lot of information and increase costs for an experiment. In situations where one prefers to examine a more limited number of analytes, methods herein are provided for targeted RNA capture. Capturing a derivative of an analyte (e.g., a ligation product) provides enhanced specificity with respect to detection of an analyte. This is because at least two probes specific for a target are required to hybridize to the target in order to facilitate ligation and ultimate capture of the nucleic acid.

Referring to FIG. 1, in an exemplary embodiment of the disclosure, provided are methods for identifying a location of an analyte in a biological sample. In some instances, the methods include 101 contacting a biological sample with array of spatially-barcoded capture probes. In some instances, the array is on a substrate and the array includes a plurality of capture probes, wherein a capture probe of the plurality includes: (i) a spatial barcode and (ii) a capture domain. After placing the biological sample on the array, the biological sample 102 is contacted with a first probe and a second probe, wherein the first probe and the second probe each include one or more sequences that are substantially complementary to sequences of the analyte, and wherein the second probe includes a capture probe capture domain; the first probe and the second probe 103 hybridize to complementary sequences in the analyte. After hybridization a ligation product comprising the first probe and the second probe 104 is generated, and the ligation product is released from the analyte. The liberated ligation product is then freed 105 to hybridize to the capture domain of a probe on the array. After capture, (i) all or a part of the sequence of the ligation product specifically bound to the capture domain, or a complement thereof, and (ii) all or a part of the sequence of the spatial barcode, or a complement thereof 106 can be determined, and then one can use the determined sequence of (i) and (ii) 107 to identify the location of the analyte in the biological sample.

Figure 13:
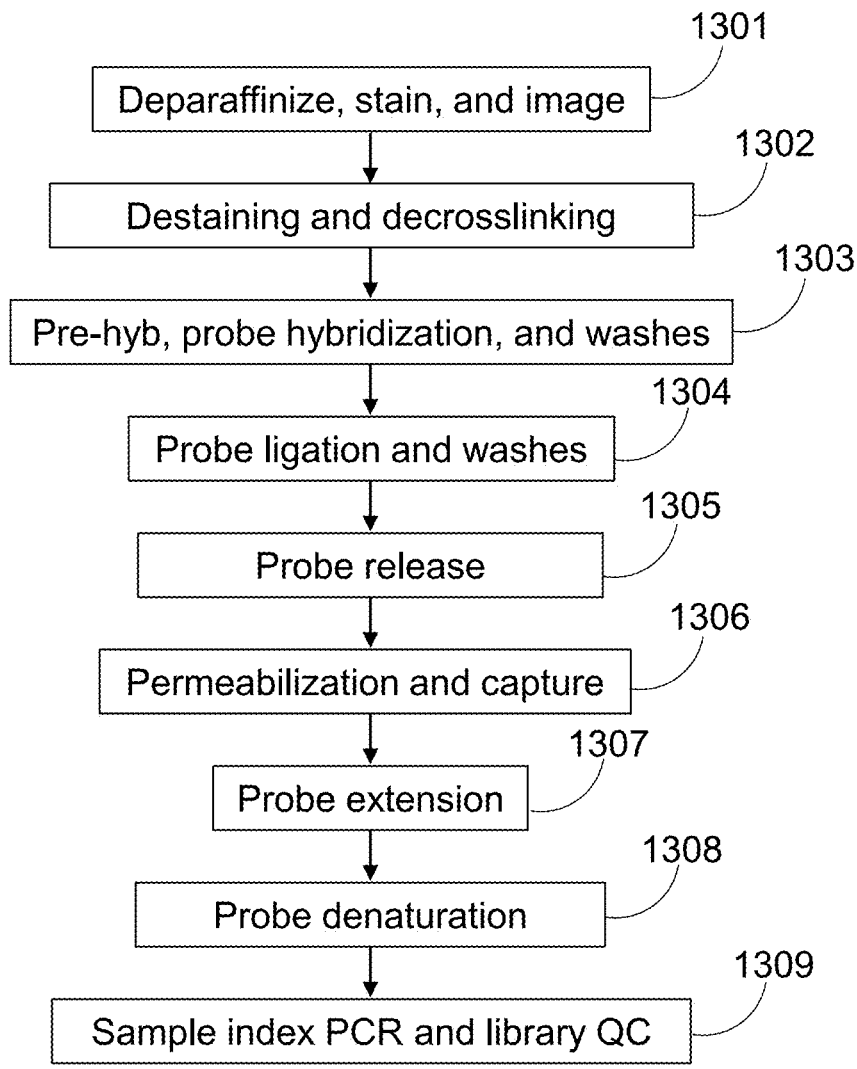
FIG. 13 shows an exemplary RNA-templated ligation workflow.

Referring to FIG. 13, in another non-limiting example, a biological sample is deparaffinized, stained, and imaged 1301. After destaining and decrosslinking 1302, probes are added to the sample and hybridize to an analyte 1303. In some instances, the probes are DNA probes. In some instances, the probes are diribo-containing probes. Probes are ligated 1304 and then released using an endonuclease such as RNAse H 1305. Ligated probes are captured on an array by a capture probe 1306, extended using a polymerase 1307 and denatured 1308. After quality control cleanup 1309, the abundance and location of an analyte is determined.

Figure 6:
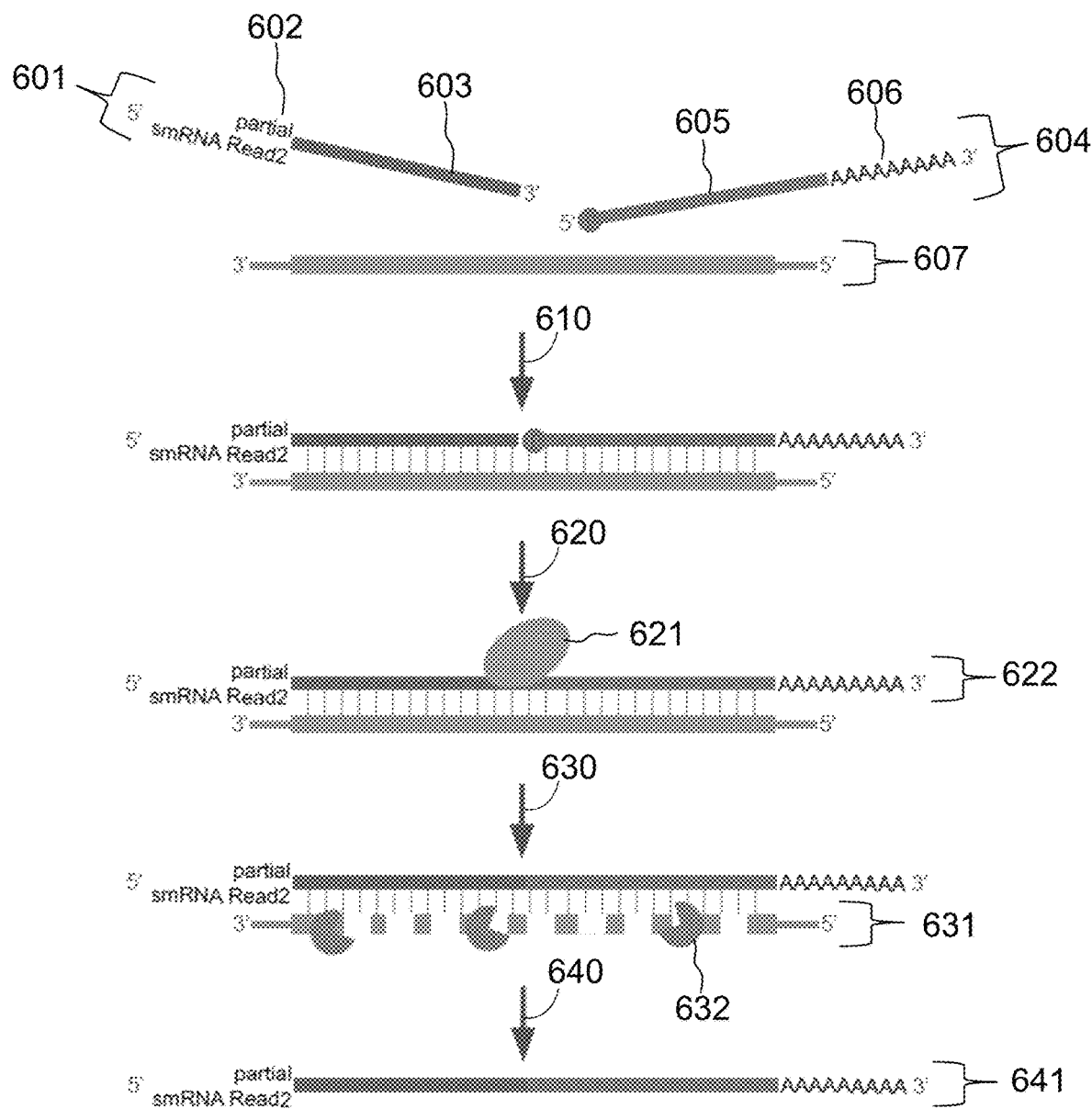
FIG. 6 is a schematic diagram showing an exemplary workflow for RNA-templated ligation.

A non-limiting example of the methods disclosed herein is depicted in FIG. 6. After a biological sample is contacted with a substrate including a plurality of capture probes and contacted with (a) a first probe 601 having a target-hybridization sequence 603 and a primer sequence 602 and (b) a second probe 604 having a target-hybridization sequence 605 and a capture domain (e.g., a poly-A sequence) 606, the first probe 601 and a second probe 604 hybridize 610 to an analyte 607. A ligase 621 ligates 620 the first probe to the second probe thereby generating a ligation product 622. The ligation product is released 630 from the analyte 631 by digesting the analyte using an endoribonuclease 632. The sample is permeabilized 640 and the ligation product 641 is able to hybridize to a capture probe on the substrate.

Also provided herein are methods for identifying a location of an analyte in a biological sample that includes a second probe including a pre-adenylated phosphate group at its 5' end, which enables the ligating to use a ligase that does not require adenosine triphosphate for ligase activity.

Also provided herein are methods for identifying a location of an analyte in a biological sample that includes one or more spanning probes, in addition to the first and second probes. Using a spanning probe enables greater flexibility in designing RTL probes, primarily by increasing the sequences within the analyte that can be used as optional target sequences.

Also provided herein are methods for identifying a location of an analyte in a biological sample that includes optimized hybridizing, washing, and releasing steps.

Figure 7:
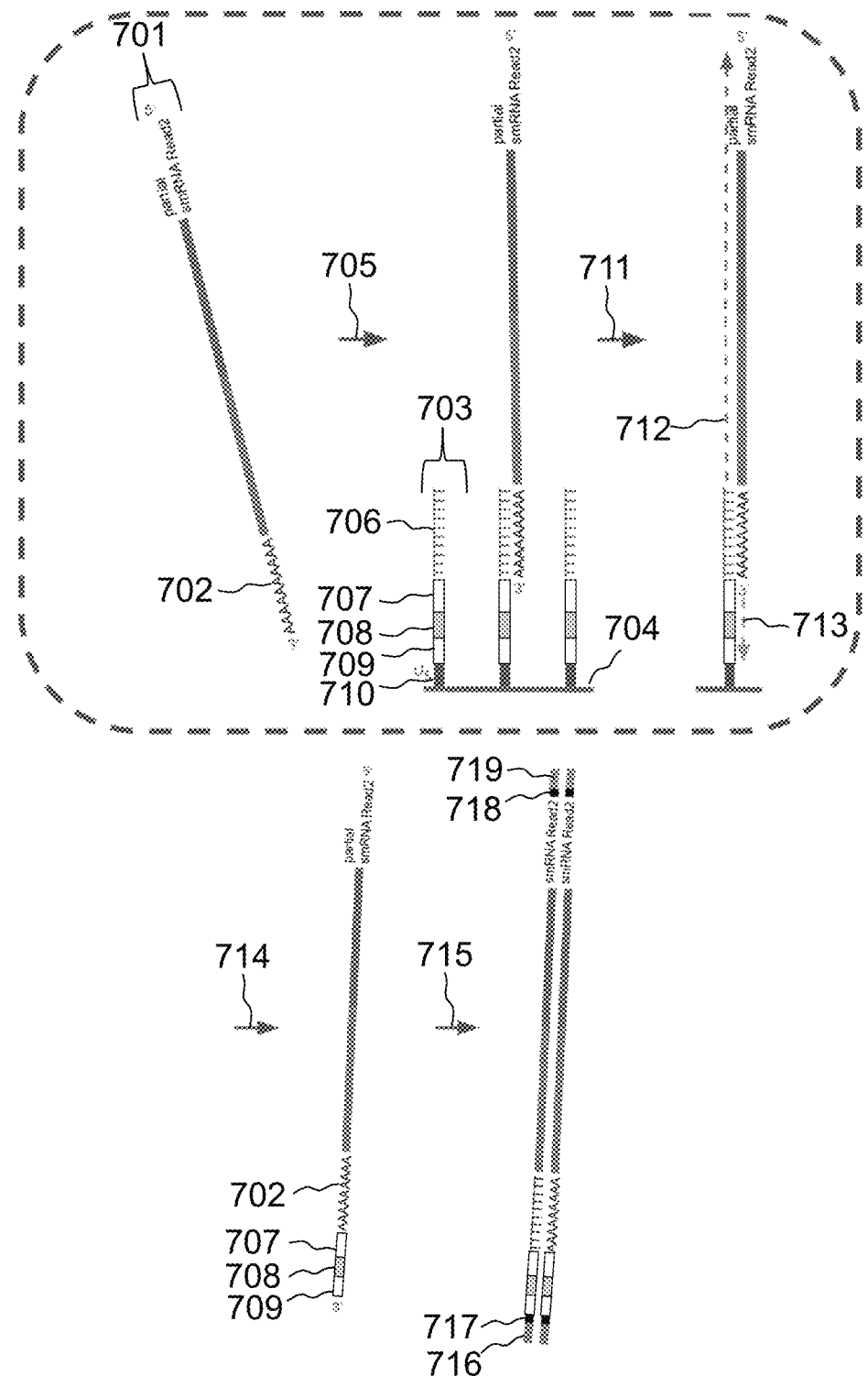
FIG. 7 is a schematic diagram showing an exemplary workflow for capturing a ligation product on a substrate that includes capture probes.

In some embodiments, as shown in FIG. 7, the ligation product 701 includes a capture probe capture domain 702, which can bind to a capture probe 703 (e.g., a capture probe immobilized, directly or indirectly, on a substrate 704). In some embodiments, methods provided herein include contacting 705 a biological sample with a substrate 704, wherein the capture probe 703 is affixed to the substrate (e.g., immobilized to the substrate, directly or indirectly). In some embodiments, the capture probe capture domain 702 of the ligated product specifically binds to the capture domain 706. The capture probe can also include a unique molecular identifier (UMI) 707, a spatial barcode 708, a functional sequence 709, and a cleavage domain 710.

In some embodiments, methods provided herein include permeabilization of the biological sample such that the capture probe can more easily bind to the captured ligated probe (i.e., compared to no permeabilization). In some embodiments, reverse transcription (RT) reagents can be added to permeabilized biological samples. Incubation with the RT reagents can extend the capture probes 711 to produce spatially-barcoded full-length cDNA 712 and 713 from the captured analytes (e.g., polyadenylated mRNA). Second strand reagents (e.g., second strand primers, enzymes) can be added to the biological sample on the slide to initiate second strand synthesis.

In some embodiments, cDNA can be denatured 714 from the capture probe template and transferred (e.g., to a clean tube) for amplification, and/or library construction. The spatially-barcoded, full-length cDNA can be amplified 715 via PCR prior to library construction. The cDNA can then be enzymatically fragmented and size-selected in order to optimize the cDNA amplicon size. P5 716, i5 717, i7 718, and P7 719, and can be used as sample indexes, and TruSeq Read 2 can be added via End Repair, A-tailing, Adaptor Ligation, and PCR. The cDNA fragments can then be sequenced using paired-end sequencing using TruSeq Read 1 and TruSeq Read 2 as sequencing primer sites.

(b) Probes for RNA-Templated Ligation

The methods provided herein utilize probe pairs (or sets; the terms are interchangeable). In some instances, the probe pairs are designed so that each probe hybridizes to a sequence in an analyte that is specific to the analyte (e.g., compared to the entire genome). That is, in some instances, a single probe pair can be specific to a single analyte.

In other embodiments, probes can be designed so that one of the probes of a pair is a probe that hybridizes to a specific sequence. Then, the other probe can be designed to detect a mutation of interest. Accordingly, in some instances, multiple second probes can be designed and can vary so that each binds to a specific sequence. For example, one second probe can be designed to hybridize to a wild-type sequence, and another second probe can be designed to detect a mutated sequence. Thus, in some instances, a probe set can include one first probe and two second probes (or vice versa).

On the other hand, in some instances, probes can be designed so that they cover conserved regions of an analyte. Thus, in some instances, a probe (or probe pair can hybridize to similar analytes in a biological sample (e.g., to detect conserved or similar analytes) or in different biological samples (e.g., across different species).

In some embodiments, probe sets cover all or nearly all of a genome (e.g., human genome). In instances where probe sets are designed to cover an entire genome (e.g., the human genome), the methods disclosed herein can detect analytes in an unbiased manner. In some instances, one probe oligonucleotide pair is designed to cover one analyte (e.g., transcript). In some instances, more than one probe oligonucleotide pair (e.g., a probe pair comprising a first probe and a second probe) is designed to cover one analyte (e.g., transcript). For example, at least two, three, four, five, six, seven, eight, nine, ten, or more probe sets can be used to hybridize to a single analyte. Factors to consider when designing probes is presence of variants (e.g., SNPs, mutations) or multiple isoforms expressed by a single gene. In some instances, the probe oligonucleotide pair does not hybridize to the entire analyte (e.g., a transcript), but instead the probe oligonucleotide pair hybridizes to a portion of the entire analyte (e.g., transcript).

In some instances, about 5000, 10,000, 15,000, 20,000, or more probe oligonucleotides pair (e.g., a probe pair comprising a first probe and a second probe) are used in the methods described herein. In some instances, about 20,000 probe oligonucleotides pair are used in the methods described herein In some instances, RNA capture is targeted RNA capture. Targeted RNA capture using the methods disclosed herein allows for examination of a subset of RNA analytes from the entire transcriptome. In some embodiments, the subset of analytes includes an individual target RNA. In some embodiments, the subset of analytes includes two or more targeted RNAs. In some embodiments, the subset of analytes includes one or more mRNAs transcribed by one or more targeted genes. In some embodiments, the subset of analytes includes one or more mRNA splice variants of one or more targeted genes. In some embodiments, the subset of analytes includes non-polyadenylated RNAs in a biological sample. In some embodiments, the subset of analytes includes detection of mRNAs having one or more single nucleotide polymorphisms (SNPs) in a biological sample.

In some embodiments, the subset of analytes includes mRNAs that mediate expression of a set of genes of interest. In some embodiments, the subset of analytes includes mRNAs that share identical or substantially similar sequences, which mRNAs are translated into polypeptides having similar functional groups or protein domains. In some embodiments, the subset of analytes includes mRNAs that do not share identical or substantially similar sequences, which mRNAs are translated into proteins that do not share similar functional groups or protein domains. In some embodiments, the subset of analytes includes mRNAs that are translated into proteins that function in the same or similar biological pathways. In some embodiments, the biological pathways are associated with a pathologic disease. For example, targeted RNA capture can detect genes that are overexpressed or underexpressed in cancer.

In some embodiments, the subset of analytes includes 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 110, about 120, about 130, about 140, about 150, about 160, about 170, about 180, about 190, about 200, about 225, about 250, about 275, about 300, about 325, about 350, about 375, about 400, about 425, about 450, about 475, about 500, about 600, about 700, about 800, about 900, or about 1000 analytes.

In some instances, the methods disclosed herein can detect the abundance and location of at least 5,000, 10,000, 15,000, 20,000, or more different analytes.

In some embodiments, the subset of analytes detected by targeted RNA capture methods provided herein includes a large proportion of the transcriptome of one or more cells. For example, the subset of analytes detected by targeted RNA capture methods provided herein can include at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more of the mRNAs present in the transcriptome of one or more cells.

In some instances, the probes are DNA probes. In some instances, the probes are diribo-containing probes.

Additional embodiments of probe(s) and probe set(s) are described herein.

(i) First Probe

In some embodiments, the methods described herein include a first probe. As used herein, a "first probe" can refer to a probe that hybridizes to all or a portion of an analyte and can be ligated to one or more additional probes (e.g., a second probe or a spanning probe). In some embodiments, "first probe" can be used interchangeably with "first probe oligonucleotide."

In some embodiments, the first probe includes ribonucleotides, deoxyribonucleotides, and/or synthetic nucleotides that are capable of participating in Watson-Crick type or analogous base pair interactions. In some embodiments, the first probe includes deoxyribonucleotides. In some embodiments, the first probe includes deoxyribonucleotides and ribonucleotides. In some embodiments, the first probe includes a deoxyribonucleic acid that hybridizes to an analyte, and includes a portion of the oligonucleotide that is not a deoxyribonucleic acid. For example, in some embodiments, the portion of the first oligonucleotide that is not a deoxyribonucleic acid is a ribonucleic acid or any other non-deoxyribonucleic acid nucleic acid as described herein. In some embodiments where the first probe includes deoxyribonucleotides, hybridization of the first probe to the mRNA molecule results in a DNA:RNA hybrid. In some embodiments, the first probe includes only deoxyribonucleotides and upon hybridization of the first probe to the mRNA molecule results in a DNA:RNA hybrid.

In some embodiments, the method includes a first probe that includes one or more sequences that are substantially complementary to one or more sequences of an analyte. In some embodiments, a first probe includes a sequence that is substantially complementary to a first target sequence in the analyte. In some embodiments, the sequence of the first probe that is substantially complementary to the first target sequence in the analyte is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the first target sequence in the analyte.

In some embodiments, a first probe includes a sequence that is about 10 nucleotides to about 100 nucleotides (e.g., a sequence of about 10 nucleotides to about 90 nucleotides, about 10 nucleotides to about 80 nucleotides, about 10 nucleotides to about 70 nucleotides, about 10 nucleotides to about 60 nucleotides, about 10 nucleotides to about 50 nucleotides, about 10 nucleotides to about 40 nucleotides, about 10 nucleotides to about 30 nucleotides, about 10 nucleotides to about 20 nucleotides, about 20 nucleotides to about 100 nucleotides, about 20 nucleotides to about 90 nucleotides, about 20 nucleotides to about 80 nucleotides, about 20 nucleotides to about 70 nucleotides, about 20 nucleotides to about 60 nucleotides, about 20 nucleotides to about 50 nucleotides, about 20 nucleotides to about 40 nucleotides, about 20 nucleotides to about 30 nucleotides, about 30 nucleotides to about 100 nucleotides, about 30 nucleotides to about 90 nucleotides, about 30 nucleotides to about 80 nucleotides, about 30 nucleotides to about 70 nucleotides, about 30 nucleotides to about 60 nucleotides, about 30 nucleotides to about 50 nucleotides, about 30 nucleotides to about 40 nucleotides, about 40 nucleotides to about 100 nucleotides, about 40 nucleotides to about 90 nucleotides, about 40 nucleotides to about 80 nucleotides, about 40 nucleotides to about 70 nucleotides, about 40 nucleotides to about 60 nucleotides, about 40 nucleotides to about 50 nucleotides, about 50 nucleotides to about 100 nucleotides, about 50 nucleotides to about 90 nucleotides, about 50 nucleotides to about 80 nucleotides, about 50 nucleotides to about 70 nucleotides, about 50 nucleotides to about 60 nucleotides, about 60 nucleotides to about 100 nucleotides, about 60 nucleotides to about 90 nucleotides, about 60 nucleotides to about 80 nucleotides, about 60 nucleotides to about 70 nucleotides, about 70 nucleotides to about 100 nucleotides, about 70 nucleotides to about 90 nucleotides, about 70 nucleotides to about 80 nucleotides, about 80 nucleotides to about 100 nucleotides, about 80 nucleotides to about 90 nucleotides, or about 90 nucleotides to about 100 nucleotides).

In some embodiments, a sequence of the first probe that is substantially complementary to a sequence in the analyte includes a sequence that is about 5 nucleotides to about 50 nucleotides (e.g., about 5 nucleotides to about 45 nucleotides, about 5 nucleotides to about 40 nucleotides, about 5 nucleotides to about 35 nucleotides, about 5 nucleotides to about 30 nucleotides, about 5 nucleotides to about 25 nucleotides, about 5 nucleotides to about 20 nucleotides, about 5 nucleotides to about 15 nucleotides, about 5 nucleotides to about 10 nucleotides, about 10 nucleotides to about 50 nucleotides, about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 25 nucleotides, about 10 nucleotides to about 20 nucleotides, about 10 nucleotides to about 15 nucleotides, about 15 nucleotides to about 50 nucleotides, about 15 nucleotides to about 45 nucleotides, about 15 nucleotides to about 40 nucleotides, about 15 nucleotides to about 35 nucleotides, about 15 nucleotides to about 30 nucleotides, about 15 nucleotides to about 25 nucleotides, about 15 nucleotides to about 20 nucleotides, about 20 nucleotides to about 50 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 25 nucleotides, about 25 nucleotides to about 50 nucleotides, about 25 nucleotides to about 45 nucleotides, about 25 nucleotides to about 40 nucleotides, about 25 nucleotides to about 35 nucleotides, about 25 nucleotides to about 30 nucleotides, about 30 nucleotides to about 50 nucleotides, about 30 nucleotides to about 45 nucleotides, about 30 nucleotides to about 40 nucleotides, about 30 nucleotides to about 35 nucleotides, about 35 nucleotides to about 50 nucleotides, about 35 nucleotides to about 45 nucleotides, about 35 nucleotides to about 40 nucleotides, about 40 nucleotides to about 50 nucleotides, about 40 nucleotides to about 45 nucleotides, or about 45 nucleotides to about 50 nucleotides).

In some embodiments, a first probe includes a functional sequence. In some embodiments, a functional sequence includes a primer sequence.

In some embodiments, a first probe includes at least two ribonucleic acid bases at the 3' end. In such cases, a second probe oligonucleotide comprises a phosphorylated nucleotide at the 5' end. In some embodiments, a first probe includes at least three, at least four, at least five, at least six, at least seven, at least eight, at least nine, or at least ten ribonucleic acid bases at the 3' end.

As shown in FIG. 6, a non-limiting example of a first probe 601, which can be referred to as an LHS probe, includes a functional sequence 602, a sequence 603 that is substantially complementary to a first target sequence in the analyte 607, and two ribonucleic acid bases at the 3' end.

In some embodiments, a first probe includes an auxiliary sequence that does not hybridize to an analyte. In some embodiments, the auxiliary sequence can be used to hybridize to additional probes.

(ii) Second Probe

In some embodiments, the methods described herein include a second probe. As used herein, a "second probe" can refer to a probe that hybridizes to all or a portion of an analyte and can be ligated to one or more additional probes (e.g., a first probe or a spanning probe). In some embodiments, "second probe" can be used interchangeably with "second probe oligonucleotide." One of skill in the art will appreciate that the order of the probes is arbitrary, and thus the contents of the first probe and/or second probe as disclosed herein are interchangeable.

In some embodiments, the second probe includes ribonucleotides, deoxyribonucleotides, and/or synthetic nucleotides that are capable of participating in Watson-Crick type or analogous base pair interactions. In some embodiments, the second probe includes deoxyribonucleotides. In some embodiments, the second probe includes deoxyribonucleotides and ribonucleotides. In some embodiments, the second probe includes a deoxyribonucleic acid that hybridizes to an analyte and includes a portion of the oligonucleotide that is not a deoxyribonucleic acid. For example, in some embodiments, the portion of the second probe that is not a deoxyribonucleic acid is a ribonucleic acid or any other non-deoxyribonucleic acid nucleic acid as described herein. In some embodiments where the second probe includes deoxyribonucleotides, hybridization of the second probe to the mRNA molecule results in a DNA:RNA hybrid. In some embodiments, the second probe includes only deoxyribonucleotides and upon hybridization of the first probe to the mRNA molecule results in a DNA:RNA hybrid.

In some embodiments, the method includes a second probe that includes one or more sequences that are substantially complementary to one or more sequences of an analyte. In some embodiments, a second probe includes a sequence that is substantially complementary to a second target sequence in the analyte. In some embodiments, the sequence of the second probe that is substantially complementary to the second target sequence in the analyte is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the second target sequence in the analyte.

In some embodiments, a second probe includes a sequence that is about 10 nucleotides to about 100 nucleotides (e.g., a sequence of about 10 nucleotides to about 90 nucleotides, about 10 nucleotides to about 80 nucleotides, about 10 nucleotides to about 70 nucleotides, about 10 nucleotides to about 60 nucleotides, about 10 nucleotides to about 50 nucleotides, about 10 nucleotides to about 40 nucleotides, about 10 nucleotides to about 30 nucleotides, about 10 nucleotides to about 20 nucleotides, about 20 nucleotides to about 100 nucleotides, about 20 nucleotides to about 90 nucleotides, about 20 nucleotides to about 80 nucleotides, about 20 nucleotides to about 70 nucleotides, about 20 nucleotides to about 60 nucleotides, about 20 nucleotides to about 50 nucleotides, about 20 nucleotides to about 40 nucleotides, about 20 nucleotides to about 30 nucleotides, about 30 nucleotides to about 100 nucleotides, about 30 nucleotides to about 90 nucleotides, about 30 nucleotides to about 80 nucleotides, about 30 nucleotides to about 70 nucleotides, about 30 nucleotides to about 60 nucleotides, about 30 nucleotides to about 50 nucleotides, about 30 nucleotides to about 40 nucleotides, about 40 nucleotides to about 100 nucleotides, about 40 nucleotides to about 90 nucleotides, about 40 nucleotides to about 80 nucleotides, about 40 nucleotides to about 70 nucleotides, about 40 nucleotides to about 60 nucleotides, about 40 nucleotides to about 50 nucleotides, about 50 nucleotides to about 100 nucleotides, about 50 nucleotides to about 90 nucleotides, about 50 nucleotides to about 80 nucleotides, about 50 nucleotides to about 70 nucleotides, about 50 nucleotides to about 60 nucleotides, about 60 nucleotides to about 100 nucleotides, about 60 nucleotides to about 90 nucleotides, about 60 nucleotides to about 80 nucleotides, about 60 nucleotides to about 70 nucleotides, about 70 nucleotides to about 100 nucleotides, about 70 nucleotides to about 90 nucleotides, about 70 nucleotides to about 80 nucleotides, about 80 nucleotides to about 100 nucleotides, about 80 nucleotides to about 90 nucleotides, or about 90 nucleotides to about 100 nucleotides).

In some embodiments, a sequence of the second probe that is substantially complementary to a sequence in the analyte includes a sequence that is about 5 nucleotides to about 50 nucleotides (e.g., about 5 nucleotides to about 45 nucleotides, about 5 nucleotides to about 40 nucleotides, about 5 nucleotides to about 35 nucleotides, about 5 nucleotides to about 30 nucleotides, about 5 nucleotides to about 25 nucleotides, about 5 nucleotides to about 20 nucleotides, about 5 nucleotides to about 15 nucleotides, about 5 nucleotides to about 10 nucleotides, about 10 nucleotides to about 50 nucleotides, about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 25 nucleotides, about 10 nucleotides to about 20 nucleotides, about 10 nucleotides to about 15 nucleotides, about 15 nucleotides to about 50 nucleotides, about 15 nucleotides to about 45 nucleotides, about 15 nucleotides to about 40 nucleotides, about 15 nucleotides to about 35 nucleotides, about 15 nucleotides to about 30 nucleotides, about 15 nucleotides to about 25 nucleotides, about 15 nucleotides to about 20 nucleotides, about 20 nucleotides to about 50 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 25 nucleotides, about 25 nucleotides to about 50 nucleotides, about 25 nucleotides to about 45 nucleotides, about 25 nucleotides to about 40 nucleotides, about 25 nucleotides to about 35 nucleotides, about 25 nucleotides to about 30 nucleotides, about 30 nucleotides to about 50 nucleotides, about 30 nucleotides to about 45 nucleotides, about 30 nucleotides to about 40 nucleotides, about 30 nucleotides to about 35 nucleotides, about 35 nucleotides to about 50 nucleotides, about 35 nucleotides to about 45 nucleotides, about 35 nucleotides to about 40 nucleotides, about 40 nucleotides to about 50 nucleotides, about 40 nucleotides to about 45 nucleotides, or about 45 nucleotides to about 50 nucleotides).

In some embodiments, a second probe includes a capture probe capture domain sequence. As used herein, a "capture probe capture domain" is a sequence, domain, or moiety that can bind specifically to a capture domain of a capture probe. In some embodiments, "capture domain capture domain" can be used interchangeably with "capture probe binding domain." In some embodiments, a second probe includes a sequence from 5' to 3': a sequence that is substantially complementary to a sequence in the analyte and a capture probe capture domain.

In some embodiments, a capture probe capture domain includes a poly(A) sequence. In some embodiments, the capture probe capture domain includes a poly-uridine sequence, a poly-thymidine sequence, or both. In some embodiments, the capture probe capture domain includes a random sequence (e.g., a random hexamer or octamer). In some embodiments, the capture probe capture domain is complementary to a capture domain in a capture probe that detects a particular target(s) of interest. In some embodiments, a capture probe capture domain blocking moiety that interacts with the capture probe capture domain is provided. In some embodiments, a capture probe capture domain blocking moiety includes a sequence that is complementary or substantially complementary to a capture probe capture domain. In some embodiments, a capture probe capture domain blocking moiety prevents the capture probe capture domain from binding the capture probe when present. In some embodiments, a capture probe capture domain blocking moiety is removed prior to binding the capture probe capture domain (e.g., present in a ligated probe) to a capture probe. In some embodiments, a capture probe capture domain blocking moiety includes a poly-uridine sequence, a poly-thymidine sequence, or both. In some embodiments, the capture probe capture domain sequence includes ribonucleotides, deoxyribonucleotides, and/or synthetic nucleotides that are capable of participating in Watson-Crick type or analogous base pair interactions. In some embodiments, the capture probe binding domain sequence includes at least 10, 11, 12, 13, 14, 15, 16, 17, 18, 19, or 20 nucleotides. In some embodiments, the capture probe binding domain sequence includes at least 25, 30, or 35 nucleotides.

In some embodiments, a second probe includes a phosphorylated nucleotide at the 5' end. The phosphorylated nucleotide at the 5' end can be used in a ligation reaction to ligate the second probe to the first probe.

As shown in FIG. 6, a non-limiting example of a second probe 604, which can be referred to a RHS probe, includes a sequence 605 that is substantially complementary to a second target sequence on the analyte 607 and a capture probe capture domain 606.

In some embodiments, a second probe includes an auxiliary sequence that does not hybridize to an analyte. In some embodiments, the auxiliary sequence can be used to hybridize to additional probes.

(iii) Multiple Probes

In some embodiments, the methods of target RNA capture as disclosed herein include multiple probe oligonucleotides. In some embodiments, the methods include 2, 3, 4, or more probe oligonucleotides. In some embodiments, each of the probe oligonucleotides includes ribonucleotides, deoxyribonucleotides, and/or synthetic nucleotides that are capable of participating in Watson-Crick type or analogous base pair interactions. In some embodiments, each of the probe oligonucleotides includes deoxyribonucleotides. In some embodiments, each of the probe oligonucleotides includes deoxyribonucleotides and ribonucleotides.

In some instances, the multiple probes span different target sequences, and multiple, serial ligation steps are carried out to determine the location and abundance of an analyte.

In some instances, the methods include a first probe and multiple second probes (or vice versa) are used, with the multiple second probes hybridizing to different sequences (e.g., wild-type versus mutant sequence, different isoforms, splice variants) in order to identify the sequence of an analyte. It is appreciated that this method can be utilized to detect single mutations (e.g., point mutations, SNPs, splice variants, etc.) or can multi-nucleotide mutations (e.g., insertions, deletions, etc.).

Methods provided herein may be applied to a single nucleic acid molecule or a plurality of nucleic acid molecules. A method of analyzing a sample comprising a nucleic acid molecule may comprise providing a plurality of nucleic acid molecules (e.g., RNA molecules), where each nucleic acid molecule comprises a first target region (e.g., a first target sequence) and a second target region (e.g., a second target sequence), a plurality of first probe oligonucleotides, and a plurality of second probe oligonucleotides. In some cases, one or more target regions of nucleic acid molecules of the plurality of nucleic acid molecules may comprise the same sequence. The first and second target regions (e.g., the first and second target sequences) of a nucleic acid molecule of the plurality of nucleic acid molecules may be adjacent to one another.

(iv) First Probe Having a Linker Sequence

Also provided herein are methods for identifying a location of an analyte in a biological sample where the method includes a first probe that includes a linker and a second probe. Using a pair of probes where the first probe includes a linker sequence enables greater flexibility in designing RTL probes, primarily by increasing the sequences within the analyte that can be used as optional target sequences.

As used herein, a "linker sequence" can refer to one or more nucleic acids sequences on a probe (e.g., a first probe, a second probe, or a spanning probe that are disposed between sequences that hybridize to an analyte, sequences that link together the analyte specific sequences of a probe). In some embodiments, a linker includes a sequence that is not substantially complementary to either the sequence of the target analyte or to the analyte specific sequences of a first probe, a second probe, or a spanning probe. In some embodiments, the linker sequence includes ribonucleotides, deoxyribonucleotides, and/or synthetic nucleotides, where the sequence within the linker is not substantially complementary to the target analyte or the analyte specific sequences of a first probe, a second probe, or a spanning probe.

In some embodiments where a first and/or a second probe include a linker sequence, the linker sequence can include a total of about 10 nucleotides to about 100 nucleotides, or any of the subranges described herein.

In some embodiments, a linker sequence includes a barcode sequence that serves as a proxy for identifying the analyte. In some embodiments, the barcode sequence is a sequence that is at least 70% identical (e.g., at least 75% identical, at least 80% identical, at least 85% identical, at least 90% identical, at least 95% identical, or at least 99% identical) to a sequence in the analyte. In some embodiments where a linker sequence includes a barcode sequence, the barcode sequence is located 5' to the linker sequence. In some embodiments where a linker sequence includes a barcode sequence, the barcode sequence is located 3' to the linker sequence. In some embodiments, the barcode sequence is disposed between two linker sequences. In such cases, the two linker sequences flanking the barcode sequence can be considered to be a part of the same linker sequence.

In some embodiments where a first and/or a second probe include a linker sequence, the linker sequence can include ribonucleotides, deoxyribonucleotides, and/or synthetic nucleotides.

A non-limiting example of a method for identifying a location of an analyte in a biological sample includes a first probe that includes a linker sequence and a second probe comprising: (a) contacting the biological sample with a substrate including a plurality of capture probes, wherein a capture probe of the plurality of capture probes includes a capture domain and a spatial barcode; (b) contacting the biological sample with a first probe and a second probe, wherein a portion of the first probe and a portion of the second probe are substantially complementary to adjacent sequences of the analyte, wherein the first probe includes: (i) a first sequence that is substantially complementary to a first target sequence of the analyte; (ii) a linker sequence; (iii) a second sequence that is substantially complementary to a second target sequence of the analyte; and wherein the second probe includes a sequence that is substantially complementary to a third target sequence of the analyte and a capture probe capture domain that is capable of binding to a capture domain of a capture probe; (c) hybridizing the first probe and the second probe to the analyte; (d) ligating the first probe and the second probe, thereby creating a ligation product; (e) releasing the ligation product from the analyte; (f) hybridizing the capture probe binding domain to a capture domain; and (g) determining (i) all or a part of the sequence of the ligation product specifically bound to the capture domain, or a complement thereof, and (ii) all or a part of the sequence of the spatial barcode, or a complement thereof, and using the determined sequence of (i) and (ii) to identify the location of the analyte in the biological sample.

Figure 8:
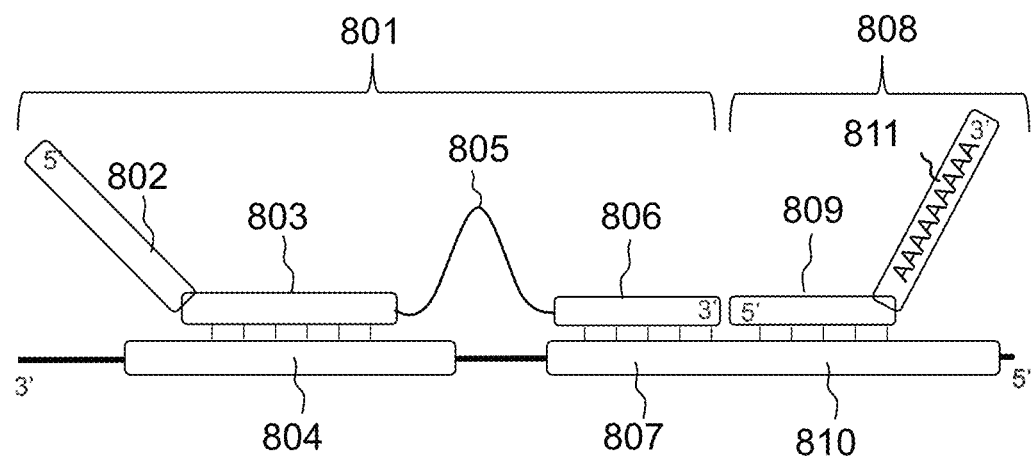
FIG. 8 is a schematic diagram showing an example of a first probe that includes a linker sequence and a second probe.

A non-limiting example of a method for identifying a location of an analyte in a biological sample where the method includes a first probe that includes a linker and a second probe can include the components as shown FIG. 8. A first probe 801 includes a functional sequence 802, a first sequence 803 that sequence that is substantially complementary to a first target sequence 804 of the analyte, a linker sequence 805; and a second sequence 806 that is substantially complementary to a second target sequence 807 of the analyte. A second probe 808 includes a sequence 809 that is substantially complementary to a third target sequence 810 of the analyte and a capture probe capture domain 811 that is capable of binding to a capture domain of a capture probe.

1) First Probe

In some embodiments where first probe includes a linker sequence, the first probe includes a first sequence that is substantially complementary to a first target sequence of the analyte, a linker sequence, and a second sequence that is substantially complementary to second target sequence of the analyte. In some embodiments, a first probe includes from 5' to 3': a first sequence that is substantially complementary to a first target sequence of the analyte, a linker sequence, and a second sequence that is substantially complementary to second target sequence of the analyte.

In some embodiments where a first probe includes a linker sequence, the first probe includes a functional sequence. In some embodiments, a first probe includes a functional sequence, a first sequence that is substantially complementary to a first target sequence of the analyte, a linker sequence, and a second sequence that is substantially complementary to second target sequence of the analyte. In some embodiments, the functional sequence includes a primer sequence.

In some embodiments where a first probe includes a linker sequence, a first probe includes at least two ribonucleic acid bases at the 3' end. In some embodiments, a first probe includes at least three, at least four, at least five, at least six, at least seven, at least eight, at least nine, or at least ten ribonucleic acid bases at the 3' end.

In some embodiments where a first probe includes a linker, the first probe includes a sequence that is about 10 nucleotides to about 300 nucleotides (e.g., a sequence of about 10 nucleotides to about 300 nucleotides, about 10 nucleotides to about 250 nucleotides, about 10 nucleotides to about 200 nucleotides, about 10 nucleotides to about 150 nucleotides, about 10 nucleotides to about 100 nucleotides, about 10 nucleotides to about 50 nucleotides, about 50 nucleotides to about 300 nucleotides, about 50 nucleotides to about 250 nucleotides, about 50 nucleotides to about 200 nucleotides, about 50 nucleotides to about 150 nucleotides, about 50 nucleotides to about 100 nucleotides, about 100 nucleotides to about 300 nucleotides, about 100 nucleotides to about 250 nucleotides, about 100 nucleotides to about 200 nucleotides, about 100 nucleotides to about 150 nucleotides, about 150 nucleotides to about 300 nucleotides, about 150 nucleotides to about 250 nucleotides, about 150 nucleotides to about 200 nucleotides, about 200 nucleotides to about 300 nucleotides, about 200 nucleotides to about 250 nucleotides, or about 250 nucleotides to about 300 nucleotides).

In some embodiments where a first probe includes a linker sequence, the first probe includes a first sequence that is substantially complementary to a first target sequence of the analyte. In some embodiments, the first sequence of the first probe is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the first target sequence in the analyte. In some embodiments, the first sequence of the first probe that is substantially complementary to a first target sequence can include a sequence that is about 5 nucleotides to about 50 nucleotides, or any of the subranges described herein.

In some embodiments where a first probe includes a linker, the first probe includes a second sequence that is substantially complementary to a second target sequence of the analyte. In some embodiments, the second sequence of the first probe is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the second target sequence in the analyte. In some embodiments, the second sequence of the first probe that is substantially complementary to a second target sequence can include a sequence that is about 5 nucleotides to about 50 nucleotides, or any of the subranges described herein.

In some embodiments, a first probe that includes a linker sequence includes ribonucleotides, deoxyribonucleotides, and/or synthetic nucleotides that are capable of participating in Watson-Crick type or analogous base pair interactions. In some embodiments, the first probe that includes a linker sequence includes deoxyribonucleotides. In some embodiments, the first probe that includes a linker sequence includes deoxyribonucleotides and ribonucleotides. In some embodiments where the first probe that includes a linker sequence includes deoxyribonucleotides, hybridization of the first probe to the mRNA molecule results in a DNA:RNA hybrid. In some embodiments, the first probe that includes a linker sequence includes only deoxyribonucleotides and upon hybridization of the first probe to the mRNA molecule results in a DNA:RNA hybrid.

2) Second Probe

In some embodiments where a first probe includes a linker sequence, a second probe includes a sequence that is substantially complementary to a third target sequence of the analyte and a capture probe capture domain that is capable of binding to a capture domain of a capture probe. In some embodiments where a first probe includes a linker, a second probe includes a sequence that is about 10 nucleotides to about 100 nucleotides, or any of the subranges described herein.

In some embodiments where a first probe includes a linker, the sequence of the second probe is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the third target sequence in the analyte. In some embodiments, the sequence of the second probe that is substantially complementary to a third target sequence can include a sequence that is about 5 nucleotides to about 50 nucleotides, or any of the subranges described herein.

In some embodiments where a first probe includes a linker sequence, a first target sequence is not adjacent to a second target sequence. For example, the first target sequence and second target sequences are located on different exons of the same mRNA molecule. In another example, the first target sequence and the second target sequence are located on the same exon of the same mRNA molecule but are not adjacent. In some instances, the first probe and the second probe hybridize to sequences that at least about 1, 2, 3, 4, 5, 6, 7, 8, 9, 10, 11, 12, 13, 14, 15, 16, 17, 18, 19, 20, 21, 22, 23, 24, 25, or more nucleotides apart.

In some embodiments where a first probe includes a linker sequence, a second target sequence is directly adjacent to a third target sequence.

In some embodiments where a first probe includes a linker sequence, the second probe includes ribonucleotides, deoxyribonucleotides, and/or synthetic nucleotides that are capable of participating in Watson-Crick type or analogous base pair interactions. In some embodiments, the second probe includes deoxyribonucleotides. In some embodiments, the second probe includes deoxyribonucleotides and ribonucleotides. In some embodiments where the second probe includes deoxyribonucleotides, hybridization of the second probe to the mRNA molecule results in a DNA:RNA hybrid. In some embodiments, the second probe includes only deoxyribonucleotides and upon hybridization of the second probe to the mRNA molecule results in a DNA:RNA hybrid.

(v) Second Probe Having a Linker

Also provided herein are methods for identifying a location of an analyte in a biological sample where the method includes a first probe and a second probe that includes a linker sequence. Using a pair of probes where the second probe includes a linker sequence enables greater flexibility in designing RTL probes, primarily by increasing the sequences within the analyte that can be used as optional target sequences.

A non-limiting example of a method for identifying a location of an analyte in a biological sample where the method includes a first probe and a second probe that includes a linker includes: (a) contacting the biological sample with a substrate including a plurality of capture probes, wherein a capture probe of the plurality of capture probes includes a capture domain and a spatial barcode; (b) contacting the biological sample with a first probe and a second probe, wherein a portion of the first probe and a portion of the second probe are substantially complementary to adjacent sequences of the analyte, wherein the first probe includes a sequence that is substantially complementary to a first target sequence of the analyte, wherein the second probe includes: (i) a first sequence that is substantially complementary to a second target sequence of the analyte; (ii) a linker sequence; (iii) a second sequence that is substantially complementary to a third target sequence of the analyte; and (iv) a capture probe binding domain that is capable of binding to a capture domain of a capture probe; (c) hybridizing the first probe and the second probe to the analyte; (d) ligating the first probe and the second probe, thereby creating a ligation product; (e) releasing the ligation product from the analyte; (f) hybridizing the capture probe binding domain to a capture domain; and (g) determining (i) all or a part of the sequence of the ligation product specifically bound to the capture domain, or a complement thereof, and (ii) all or a part of the sequence of the spatial barcode, or a complement thereof, and using the determined sequence of (i) and (ii) to identify the location of the analyte in the biological sample.

Figure 9:
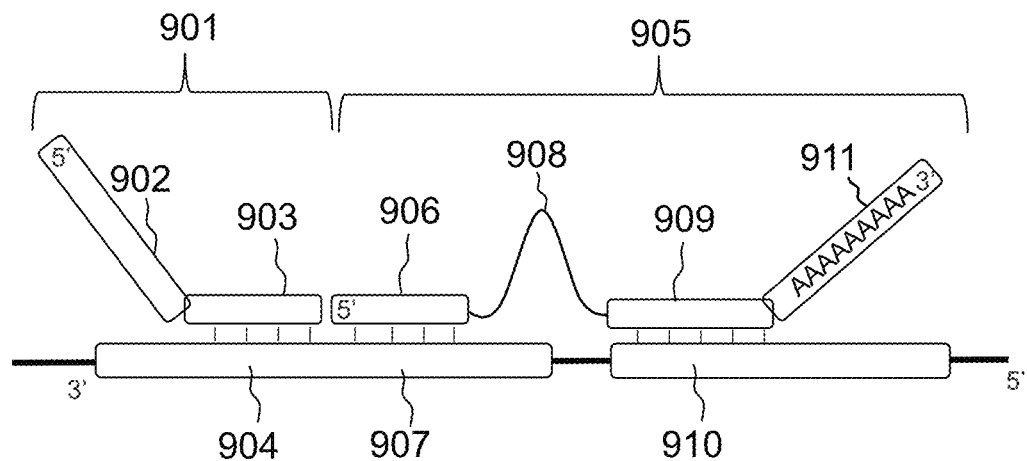
FIG. 9 is a schematic diagram showing an example of a second probe that includes a linker sequence and a first probe.

A non-limiting example of a method for identifying a location of an analyte in a biological sample where the method includes a first probe and a second probe that includes a linker can include the components as shown FIG. 9. A first probe 901 includes a functional sequence 902 and a sequence 903 that is substantially complementary to a first target sequence 904 of the analyte. A second probe 905 includes a first sequence 906 that is substantially complementary to a second target sequence 907 of the analyte, a linker sequence 908; and a second sequence 909 that is substantially complementary to a second target sequence 910 of the analyte, and a capture probe capture domain 911 that is capable of binding to a capture domain of a capture probe.

1) First Probe

In some embodiments where a second probe includes a linker sequence, a first probe includes a sequence that is substantially complementary to a first target sequence of the analyte.

In some embodiments where a second probe includes a linker sequence, a first probe includes a functional sequence. In some embodiments, a first probe includes a functional sequence and a sequence that is substantially complementary to a first target sequence of the analyte. In some embodiments, the functional sequence includes a primer sequence. In some embodiments, the first probe oligonucleotide includes from 5' to 3': a functional sequence, and a sequence that is substantially complementary to a first target sequence.

In some embodiments where a linker is on a second probe, a first probe includes a sequence that is about 10 nucleotides to about 100 nucleotides, or any of the subranges described herein.

In some embodiments where the second probe includes a linker sequence, a sequence of a first probe that is substantially complementary to a first target sequence of the analyte is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the first target sequence in the analyte. In some embodiments, the sequence that is substantially complementary to a first target sequence can include a sequence that is about 5 nucleotides to about 50 nucleotides, or any of the subranges described herein.

In some embodiments where a second probe includes a linker sequence, a first probe includes at least two ribonucleic acid bases at the 3' end. In some embodiments, a first probe includes at least three, at least four, at least five, at least six, at least seven, at least eight, at least nine, or at least ten ribonucleic acid bases at the 3' end.

In some embodiments where a second probe includes a linker sequence, the first probe includes ribonucleotides, deoxyribonucleotides, and/or synthetic nucleotides that are capable of participating in Watson-Crick type or analogous base pair interactions. In some embodiments, the first probe includes deoxyribonucleotides. In some embodiments, the first probe includes deoxyribonucleotides and ribonucleotides. In some embodiments where the first probe includes deoxyribonucleotides, hybridization of the first probe to the mRNA molecule results in a DNA:RNA hybrid. In some embodiments, the first probe includes only deoxyribonucleotides and upon hybridization of the first probe to the mRNA molecule results in a DNA:RNA hybrid.

2) Second Probe

In some embodiments where a linker is on a second probe, the second probe includes (i) a first sequence that is substantially complementary to a second target sequence of the analyte; (ii) a linker sequence (e.g., any of the exemplary linker sequences described herein); (iii) a second sequence that is substantially complementary to third target sequence of the analyte; and (iv) a capture probe capture domain (e.g., any of the exemplary capture probe capture domains described herein) that is capable of binding to a capture domain of a capture probe.

In some embodiments where a second probe includes a linker sequence, the second probe includes a sequence that is about 10 nucleotides to about 300 nucleotides, or any of the subranges described herein.

In some embodiments where a second probe includes a linker sequence, the second probe includes a first sequence that is substantially complementary to a second target sequence of the analyte. In some embodiments, the first sequence of the second probe is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the second target sequence in the analyte. In some embodiments, the first sequence of the second probe that is substantially complementary to a second target sequence can include a sequence that is about 5 nucleotides to about 50 nucleotides, or any of the subranges described herein.

In some embodiments where a second probe includes a linker sequence, the second probe includes a second sequence that is substantially complementary to a third target sequence of the analyte. In some embodiments, the second sequence of the second probe is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the third target sequence in the analyte. In some embodiments, the second sequence of the second probe that is substantially complementary to a third target sequence can include a sequence that is about 5 nucleotides to about 50 nucleotides, or any of the subranges described herein.

In some embodiments where a second probe includes a linker sequence, a second target sequence is not adjacent to a third target sequence in the mRNA molecule. For example, the second target sequence and third target sequence are located on different exons of the same mRNA molecule. In another example, the second target sequence and the third target sequence are located on the same exon of the same mRNA molecule but are not adjacent.

In some embodiments where a second probe includes a linker sequence, a first target sequence is directly adjacent to a second target sequence.

In some embodiments, a second probe that includes a linker sequence includes ribonucleotides, deoxyribonucleotides, and/or synthetic nucleotides that are capable of participating in Watson-Crick type or analogous base pair interactions. In some embodiments, the second probe that includes a linker sequence includes deoxyribonucleotides. In some embodiments, the second probe that includes a linker sequence includes deoxyribonucleotides and ribonucleotides. In some embodiments where the second probe that includes a linker sequence includes deoxyribonucleotides, hybridization of the second probe to the mRNA molecule results in a DNA:RNA hybrid. In some embodiments, the second probe that includes a linker sequence includes only deoxyribonucleotides and upon hybridization of the second probe to the mRNA molecule results in a DNA:RNA hybrid.

(vii) Probe Combination with Linkers on the First Probe and the Second Probe

Also provided herein are methods for identifying a location of an analyte in a biological sample where the method includes a first probe that includes a linker sequence and a second probe that includes a linker sequence. Using a pair of probes where the first probe and second probe each include a linker sequence enables greater flexibility in designing RTL probes, primarily by increasing the sequences within the analyte that can be used as optional target sequences.

(c) Probe Combinations Including a First Probe, a Second Probe and a Spanning Probe Also provided herein are methods for identifying a location of an analyte in a biological sample where the method includes a first probe, a spanning probe, and a second probe. Using a spanning probe enables greater flexibility in designing RTL probes, primarily by increasing the sequences within the analyte that can be used as optional target sequences. In some cases, using a spanning probe can also be used to interrogate the variants (e.g., splice variants) that span greater distances that can be interrogated using a first or second probe with a linker sequence.

A non-limiting example of a method for identifying a location of an analyte in a biological sample where the method includes a first probe, a spanning probe, and a second probe, includes: (a) contacting the biological sample with a substrate including a plurality of capture probes, wherein a capture probe of the plurality of capture probes includes a capture domain and a spatial barcode; (b) contacting the biological sample with a first probe, a second probe, and one or more spanning probes, wherein the first probe is substantially complementary to a first portion of the analyte, wherein the second probe is substantially complementary to a second portion of the analyte and further includes a capture probe binding domain, and wherein the spanning probe includes: (i) a first sequence that is substantially complementary to a first target sequence of the analyte, and (ii) a second sequence that is substantially complementary to a second target sequence of the analyte; (c) hybridizing the first probe, the second probe, and the spanning probe to the analyte; (d) ligating the first probe, the one or more spanning probes, and the second probe, thereby creating a ligation product that is substantially complementary to the analyte; (e) releasing the ligation product from the analyte; (f) hybridizing the capture probe binding domain to a capture domain; and (g) determining (i) all or a part of the sequence of the ligation product specifically bound to the capture domain, or a complement thereof, and (ii) all or a part of the sequence of the spatial barcode, or a complement thereof, and using the determined sequence of (i) and (ii) to identify the location of the analyte in the biological sample.

Figure 10:
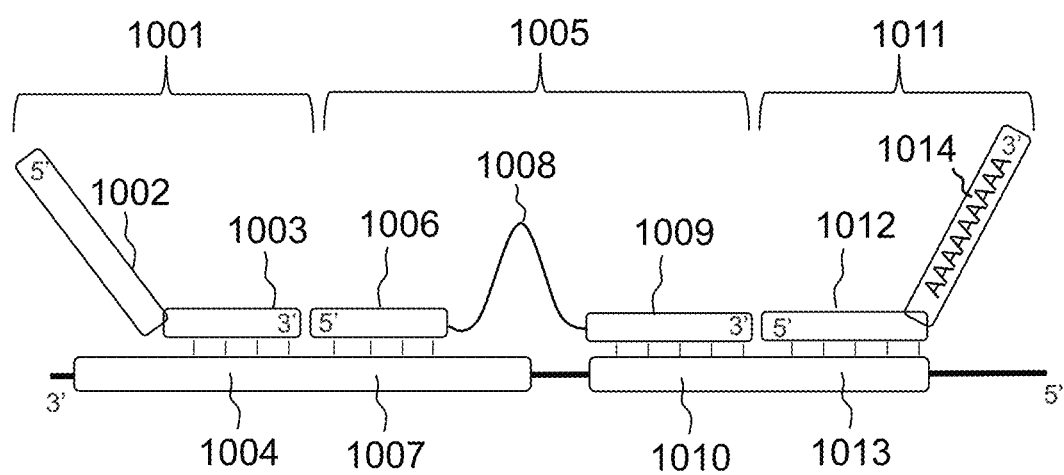
FIG. 10 is a schematic diagram showing an example of a first probe, a second probe, and a spanning probe.

A non-limiting example of a method for identifying a location of an analyte in a biological sample where the method includes a first probe, a second probe, and a spanning probe can include the components as shown FIG. 10. A first probe 1001 includes a functional sequence 1002, a sequence 1003 that is substantially complementary to a first portion 1004 of the analyte. A spanning probe 1005 includes a first sequence 1006 that is substantially complementary to a first target sequence 1007 of the analyte, a linker sequence 1008, and a second sequence 1009 that is substantially complementary to a second target sequence 1010 of the analyte. A second probe 1011 includes a sequence 1012 that is substantially complementary to a second portion 1013 of the analyte and a capture probe capture domain 1014.

(i) First Probe

In some embodiments where the method includes a spanning probe, a first probe includes a sequence that is substantially complementary to a first portion of the analyte. In some embodiments, a sequence of the first probe is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a first portion of the analyte. In some embodiments, the sequence of the first probe that is substantially complementary to a first portion of the analyte can include a sequence that is about 5 nucleotides to about 50 nucleotides, or any of the subranges described herein. In some embodiments, the first probe includes a functional sequence. In some embodiments, the functional sequence is a primer sequence.

In some embodiments where the method includes a spanning probe, a first probe includes at least two ribonucleic acid bases at the 3' end. In some embodiments, a first probe includes at least three, at least four, at least five, at least six, at least seven, at least eight, at least nine, or at least ten ribonucleic acid bases at the 3' end.

In some embodiments where the method includes a spanning probe, a first probe includes from 5' to 3': a functional sequence, a sequence that is substantially complementary to a first portion of the analyte, and two or more ribonucleic acid bases.

In some embodiments where the method includes a spanning probe, a first probe includes ribonucleotides, deoxyribonucleotides, and/or synthetic nucleotides that are capable of participating in Watson-Crick type or analogous base pair interactions. In some embodiments, the first probe includes deoxyribonucleotides. In some embodiments, the first probe includes deoxyribonucleotides and ribonucleotides. In some embodiments where the first probe includes deoxyribonucleotides, hybridization of the first probe to the mRNA molecule results in a DNA:RNA hybrid. In some embodiments, the first probe includes only deoxyribonucleotides and upon hybridization of the first probe to the mRNA molecule results in a DNA:RNA hybrid.

(ii) Spanning Probe

In some embodiments where the method includes a spanning probe, the spanning probe includes a first sequence that is substantially complementary to a first target sequence of the analyte, and a second sequence that is substantially complementary to a second target sequence of the analyte. In some embodiments, the spanning probe includes a first sequence that is substantially complementary to a first target sequence of the analyte, a functional sequence, and a second sequence that is substantially complementary to a second target sequence of the analyte. In some embodiments, a spanning probe includes from 5' to 3': a first sequence, a functional sequence, and a second sequence. In some embodiments, the functional sequence is a linker sequence. The linker sequence can include a total of about 10 nucleotides to about 100 nucleotides, or any of the subranges described herein.

In some embodiments, the functional sequence includes a barcode sequence. In some embodiments, the spanning probe can include a linker and a barcode sequence. In such cases, linker sequences can flank the barcode, the barcode can be 5' to a linker sequence, or the barcode can be 3' to a linker sequence. In some embodiments, a barcode sequence is flanked by a 5' linker sequence (e.g., any of the exemplary linker sequences described herein) and a 3' linker sequence (e.g., any of the exemplary linker sequences described herein).

In some embodiments, the spanning probe includes from 5' to 3': a first sequence, a 5' linker sequence, a barcode, a 3' linker sequence, and a second sequence.

In some embodiments, the spanning probes includes a sequence that is about 10 nucleotides to about 300 nucleotides or any of the subranges described herein.

In some embodiments, a first sequence of the spanning probe is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the first target sequence of the analyte. In some embodiments, a second sequence of the spanning probe is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the second target sequence of the analyte.

In some embodiments, the first sequence of the spanning probe and the second sequence of the spanning probe are substantially complementary to sequences within the same exon.

In some embodiments, the first target sequence of the analyte and the second target of the analyte are located within the same exon. In such cases, the first target sequence and the second target sequence are not directly adjacent.

In some embodiments, the first sequence of the spanning probe and the second sequence of the spanning probe are substantially complementary to sequences within the different exons of the same gene. In some embodiments, the first target sequence of the analyte and the second target sequence of the analyte are located on different exons of the same gene.

In some embodiments, the spanning probe includes ribonucleotides, deoxyribonucleotides, and/or synthetic nucleotides that are capable of participating in Watson-Crick type or analogous base pair interactions. In some embodiments, the spanning probe includes deoxyribonucleotides. In some embodiments, the spanning probe includes deoxyribonucleotides and ribonucleotides. In some embodiments where the spanning probe includes deoxyribonucleotides, hybridization of the spanning probe to the mRNA molecule results in a DNA:RNA hybrid. In some embodiments, the spanning probe includes only deoxyribonucleotides and upon hybridization of the spanning probe to the mRNA molecule results in a DNA:RNA hybrid.

(iii) Second Probe

In some embodiments where the method includes a spanning probe, a second probe includes a sequence that is substantially complementary to a second portion of the analyte and a capture probe capture domain (e.g., any of the exemplary capture probe capture domains described herein).

In some embodiments where the method includes a spanning probe, a sequence of the second probe is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a second portion of the analyte. In some embodiments, the sequence of the second probe that is substantially complementary to a second portion of the analyte can include a sequence that is about 5 nucleotides to about 50 nucleotides, or any of the subranges described herein.

In some embodiments where the method includes a spanning probe, the first portion of the analyte is directly adjacent to the first target sequence, and/or the second portion of the analyte is directly adjacent to the second target sequence. In such cases, the sequence of the first probe is ligated to the first sequence of the spanning probe, and the sequence of the second probe is ligated to the second sequence of the spanning probe. In some embodiments, the spanning probe includes at least two ribonucleic acid based at the 3' end, the first probe includes at least two ribonucleic acids at the 3' end, or both. In some embodiments, the spanning probe includes a phosphorylated nucleotide at the 5' end, the second probe includes a phosphorylated nucleotide at the 5' end, or both.

In some embodiments where the method includes a spanning probe, a second probe includes ribonucleotides, deoxyribonucleotides, and/or synthetic nucleotides that are capable of participating in Watson-Crick type or analogous base pair interactions. In some embodiments, the second probe includes deoxyribonucleotides. In some embodiments, the second probe includes deoxyribonucleotides and ribonucleotides. In some embodiments where the second probe includes deoxyribonucleotides, hybridization of the second probe to the mRNA molecule results in a DNA:RNA hybrid. In some embodiments, the second probe includes only deoxyribonucleotides and upon hybridization of the second probe to the mRNA molecule results in a DNA:RNA hybrid.

(iv) Probe Combinations Including a First Probe, a Second Probe, and Multiple Spanning Probes Also provided herein are methods for identifying a location of an analyte in a biological sample where the method includes a first probe, at least two spanning probes, and a second probe. Using two or more spanning probes enables greater flexibility in designing RTL probes, primarily by increasing the sequences within the analyte that can be used as optional target sequences. In some cases, using two or more spanning probe can also be used to interrogate the variants (e.g., splice variants) that span greater distances that can be interrogated using one spanning probe.

A non-limiting example of a method for identifying a location of an analyte in a biological sample where the method includes a first probe, two or more spanning probes, and a second probe, includes: (a) contacting the biological sample with a substrate including a plurality of capture probes, wherein a capture probe of the plurality of capture probes includes a capture domain and a spatial barcode; (b) contacting the biological sample with a first probe, a second probe, and two spanning probes, wherein the first probe is substantially complementary to a first portion of the analyte, wherein the second probe is substantially complementary to a second portion of the analyte and further includes a capture probe binding domain, and wherein the first spanning probe includes: (i) a first sequence that is substantially complementary to a first target sequence of the analyte, and (ii) a second sequence that is substantially complementary to a second target sequence of the analyte; and the second spanning probe includes (i) a third sequence that is substantially complementary to a third target sequence of the analyte, and (ii) a fourth sequence that is substantially complementary to a fourth target sequence of the analyte; (c) hybridizing the first probe, the second probe, and the spanning probe to the analyte; (d) ligating the first probe, the one or more spanning probes, and the second probe, thereby creating a ligation product that is substantially complementary to the analyte; (e) releasing the ligation product from the analyte; (f) hybridizing the capture probe binding domain to a capture domain; and (g) determining (i) all or a part of the sequence of the ligation product specifically bound to the capture domain, or a complement thereof, and (ii) all or a part of the sequence of the spatial barcode, or a complement thereof, and using the determined sequence of (i) and (ii) to identify the location of the analyte in the biological sample.

In some embodiments, the methods that include one or more spanning probes include at least two, at least three, at least four, at least five, or more spanning probes. In such cases, the one or more spanning probes includes (i) a third sequence that is substantially complementary to a third target sequence of the analyte, and (ii) a fourth sequence that is substantially complementary to a fourth target sequence of the analyte.

In some embodiments where the method includes two (or more) spanning probes, the first target sequence is located in a first exon, the second target sequence is located in a second exon, and the third target sequence and the fourth target sequence are located in a third exon. In some embodiments where the method includes two (or more) spanning probes, the first target sequence is located in a first exon, the second target sequence is located in a second exon, and the third target sequence is located in a third exon, and the fourth target sequence is located in a fourth exon. In some embodiments where the method includes two (or more) spanning probes, the first target sequence and the second target sequences are located in a first exon, and the third target sequence and the fourth target sequence are located in a second exon. In some embodiments where the method includes two (or more) spanning probes, the first target sequence and the second target sequences are located in a first exon, and the third target sequence is located in a second exon, and the fourth target sequence is located in a third exon.

In some embodiments, where the methods include two (or more) spanning probes, the method includes ligating: the first probe to the spanning probe, the spanning probe to the one or more additional spanning probes, and the one or more additional spanning probes spanning oligonucleotide to the second probe, thereby creating a ligation product that includes one or more sequences that are substantially complementary to the analyte. In some embodiments, where the methods include two (or more) spanning probes, the method includes ligating: the first probe to the one or more additional spanning probes, the one or more additional spanning probes to the spanning probe, and the spanning probe to the second probe, thereby creating a ligation product that includes one or more sequences that are substantially complementary to the analyte.

In some embodiments, each additional spanning probe can include a functional sequence (e.g., any of the functional sequence described herein). For example, each additional spanning probe can include a linker sequence (e.g., any of the exemplary linker sequences described herein). In another example, each additional spanning probe can include a barcode sequence (e.g., any of the exemplary barcode sequences described herein) and a linker sequence (e.g., any of the linker sequences described herein). In some embodiments where an additional spanning probe includes a barcode and a linker, a linker sequences can flank the barcode, the barcode can be 5' to a linker sequence, or the barcode can be 3' to a linker sequence. In some embodiments, a barcode sequence is flanked by a 5' linker sequence (e.g., any of the exemplary linker sequences described herein) and a 3' linker sequence (e.g., any of the exemplary linker sequences described herein). In some embodiments, an additional spanning probe can include from 5' to 3': a first sequence, a 5' linker sequence, a barcode, a 3' linker sequence, and a second sequence.

(d) Pre-Hybridization Methods (i) Imaging and Staining

Prior to addition of the probes, in some instances, biological samples can be stained using a wide variety of stains and staining techniques. In some instances, the biological sample is a section on a slide (e.g., a 10 μm section). In some instances, the biological sample is dried after placement onto a glass slide. In some instances, the biological sample is dried at 42° C. In some instances, drying occurs for about 1 hour, about 2, hours, about 3 hours, or until the sections become transparent. In some instances, the biological sample can be dried overnight (e.g., in a desiccator at room temperature).

In some embodiments, a sample can be stained using any number of biological stains, including but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin. In some instances, the methods disclosed herein include imaging the biological sample. In some instances, imaging the sample occurs prior to deaminating the biological sample. In some instances, the sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation. In some instances, the stain is an H&E stain.

In some embodiments, the biological sample can be stained using a detectable label (e.g., radioisotopes, fluorophores, chemiluminescent compounds, bioluminescent compounds, and dyes) as described elsewhere herein. In some embodiments, a biological sample is stained using only one type of stain or one technique. In some embodiments, staining includes biological staining techniques such as H&E staining. In some embodiments, staining includes identifying analytes using fluorescently-conjugated antibodies. In some embodiments, a biological sample is stained using two or more different types of stains, or two or more different staining techniques. For example, a biological sample can be prepared by staining and imaging using one technique (e.g., H&E staining and brightfield imaging), followed by staining and imaging using another technique (e.g., IHC/IF staining and fluorescence microscopy) for the same biological sample.

In some embodiments, biological samples can be destained. Methods of destaining or discoloring a biological sample are known in the art, and generally depend on the nature of the stain(s) applied to the sample. For example, H&E staining can be destained by washing the sample in HCl, or any other acid (e.g., selenic acid, sulfuric acid, hydroiodic acid, benzoic acid, carbonic acid, malic acid, phosphoric acid, oxalic acid, succinic acid, salicylic acid, tartaric acid, sulfurous acid, trichloroacetic acid, hydrobromic acid, hydrochloric acid, nitric acid, orthophosphoric acid, arsenic acid, selenous acid, chromic acid, citric acid, hydrofluoric acid, nitrous acid, isocyanic acid, formic acid, hydrogen selenide, molybdic acid, lactic acid, acetic acid, carbonic acid, hydrogen sulfide, or combinations thereof). In some embodiments, destaining can include 1, 2, 3, 4, 5, or more washes in an acid (e.g., HCl). In some embodiments, destaining can include adding HCl to a downstream solution (e.g., permeabilization solution). In some embodiments, destaining can include dissolving an enzyme used in the disclosed methods (e.g., pepsin) in an acid (e.g., HCl) solution. In some embodiments, after destaining hematoxylin with an acid, other reagents can be added to the destaining solution to raise the pH for use in other applications. For example, SDS can be added to an acid destaining solution in order to raise the pH as compared to the acid destaining solution alone. As another example, in some embodiments, one or more immunofluorescence stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., J. Histochem. Cytochem. 2017; 65(8): 431-444, Lin et al., Nat Commun. 2015; 6:8390, Pirici et al., J. Histochem. Cytochem. 2009; 57:567-75, and Glass et al., J. Histochem. Cytochem. 2009; 57:899-905, the entire contents of each of which are incorporated herein by reference.

In some embodiments, immunofluorescence or immunohistochemistry protocols (direct and indirect staining techniques) can be performed as a part of, or in addition to, the exemplary spatial workflows presented herein. For example, tissue sections can be fixed according to methods described herein. The biological sample can be transferred to an array (e.g., capture probe array), wherein analytes (e.g., proteins) are probed using immunofluorescence protocols. For example, the sample can be rehydrated, blocked, and permeabilized (3×SSC, 2% BSA, 0.1% Triton X, 1 U/μl RNAse inhibitor for 10 minutes at 4° C.) before being stained with fluorescent primary antibodies (1:100 in 3×SSC, 2% BSA, 0.1% Triton X, 1 U/μl RNAse inhibitor for 30 minutes at 4° C.). The biological sample can be washed, coverslipped (in glycerol+1 U/μl RNAse inhibitor), imaged (e.g., using a confocal microscope or other apparatus capable of fluorescent detection), washed, and processed according to analyte capture or spatial workflows described herein.

In some instances, a glycerol solution and a cover slip can be added to the sample. In some instances, the glycerol solution can include a counterstain (e.g., DAPI).

As used herein, an antigen retrieval buffer can improve antibody capture in IF/IHC protocols. An exemplary protocol for antigen retrieval can be preheating the antigen retrieval buffer (e.g., to 95° C.), immersing the biological sample in the heated antigen retrieval buffer for a predetermined time, and then removing the biological sample from the antigen retrieval buffer and washing the biological sample.

In some embodiments, optimizing permeabilization can be useful for identifying intracellular analytes. Permeabilization optimization can include selection of permeabilization agents, concentration of permeabilization agents, and permeabilization duration. Tissue permeabilization is discussed elsewhere herein.

In some embodiments, blocking an array and/or a biological sample in preparation of labeling the biological sample decreases nonspecific binding of the antibodies to the array and/or biological sample (decreases background). Some embodiments provide for blocking buffers/blocking solutions that can be applied before and/or during application of the label, wherein the blocking buffer can include a blocking agent, and optionally a surfactant and/or a salt solution. In some embodiments, a blocking agent can be bovine serum albumin (BSA), serum, gelatin (e.g., fish gelatin), milk (e.g., non-fat dry milk), casein, polyethylene glycol (PEG), polyvinyl alcohol (PVA), or polyvinylpyrrolidone (PVP), biotin blocking reagent, a peroxidase blocking reagent, levamisole, Carnoy's solution, glycine, lysine, sodium borohydride, pontamine sky blue, Sudan Black, trypan blue, FITC blocking agent, and/or acetic acid. The blocking buffer/blocking solution can be applied to the array and/or biological sample prior to and/or during labeling (e.g., application of fluorophore-conjugated antibodies) to the biological sample.

(ii) Preparation of Sample for Application of Probes

In some instances, the biological sample is deparaffinized. Deparaffinization can be achieved using any method known in the art. For example, in some instances, the biological samples is treated with a series of washes that include xylene and various concentrations of ethanol. In some instances, methods of deparaffinization include treatment of xylene (e.g., three washes at 5 minutes each). In some instances, the methods further include treatment with ethanol (e.g., 100% ethanol, two washes 10 minutes each; 95% ethanol, two washes 10 minutes each; 70% ethanol, two washes 10 minutes each; 50% ethanol, two washes 10 minutes each). In some instances, after ethanol washes, the biological sample can be washed with deionized water (e.g., two washes for 5 minutes each). It is appreciated that one skilled in the art can adjust these methods to optimize deparaffinization.

In some instances, the biological sample is decrosslinked. In some instances, the biological sample is decrosslinked in a solution containing TE buffer (comprising Tris and EDTA). In some instances, the TE buffer is basic (e.g., at a pH of about 9). In some instances, decrosslinking occurs at about 50° C. to about 80° C. In some instances, decrosslinking occurs at about 70° C. In some instances, decrosslinking occurs for about 1 hour at 70° C. Just prior to decrosslinking, the biological sample can be treated with an acid (e.g., 0.1M HCl for about 1 minute). After the decrosslinking step, the biological sample can be washed (e.g., with 1×PBST).

In some instances, the methods of preparing a biological sample for probe application include permeabilizing the sample. In some instances, the biological sample is permeabilized using a phosphate buffer. In some instances, the phosphate buffer is PBS (e.g., 1×PBS). In some instances, the phosphate buffer is PBST (e.g., 1×PBST). In some instances, the permeabilization step is performed multiple times (e.g., 3 times at 5 minutes each).

In some instances, the methods of preparing a biological sample for probe application include steps of equilibrating and blocking the biological sample. In some instances, equilibrating is performed using a pre-hybridization (pre-Hyb) buffer. In some instances, the pre-Hyb buffer is RNase-free. In some instances, the pre-Hyb buffer contains no bovine serum albumin (BSA), solutions like Denhardt's, or other potentially nuclease-contaminated biological materials.

In some instances, the equilibrating step is performed multiple times (e.g., 2 times at 5 minutes each; 3 times at 5 minutes each). In some instances, the biological sample is blocked with a blocking buffer. In some instances, the blocking buffer includes a carrier such as tRNA, for example yeast tRNA such as from brewer's yeast (e.g., at a final concentration of 10-20 µg/mL). In some instances, blocking can be performed for 5, 10, 15, 20, 25, or 30 minutes.

Any of the foregoing steps can be optimized for performance. For example, one can vary the temperature. In some instances, the pre-hybridization methods are performed at room temperature. In some instances, the pre-hybridization methods are performed at 4° C. (in some instances, varying the timeframes provided herein).

(e) Hybridizing the Probes

In some embodiments, the methods of targeted RNA capture provided herein include hybridizing a first probe oligonucleotide and a second probe oligonucleotide (e.g., a probe pair). In some instances, the first and second probe oligonucleotides each include sequences that are substantially complementary to one or more sequences (e.g., one or more target sequences) of an analyte of interest. In some embodiments, the first probe and the second probe bind to complementary sequences that are completely adjacent (i.e., no gap of nucleotides) to one another or are on the same transcript.

In some instances, the methods include hybridization of probe sets, wherein the probe pairs are in a medium at a concentration of about 1 to about 100 nM. In some instances, the concentration of the probe pairs is about 1, 2, 3, 4, 5, 6, 7, 8, 9, 10, 15, 20, 25, 30, 35, 40, 45, 50, 60, 70, 80, 90, 100, 200, 300, 400, or 500 nM. In some instances, the concentration of the probe pairs is 5 nM. In some instances, the probe sets are diluted in a hybridization (Hyb) buffer. In some instances, the probe sets are at a concentration of 5 nM in Hyb buffer.

In some instances, probe hybridization occurs at about 50° C. In some instances, the temperature of probe hybridization ranges from about 30° C. to about 75° C., from about 35° C. to about 70° C., or from about 40° C. to about 65° C. In some embodiments, the temperature is about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., or about 70° C. In some instances, probe hybridization occurs for about 30 minutes, about 1 hour, about 2 hours, about 2.5 hours, about 3 hours, or more. In some instances, probe hybridization occurs for about 2.5 hours at 50° C.

In some instances, the hybridization buffer includes SSC (e.g., 1×SSC) or SSPE. In some instances, the hybridization buffer includes formamide or ethylene carbonate. In some instances, the hybridization buffer includes one or more salts, like Mg salt for example $MgCl_2$, Na salt for example NaCl, Mn salt for example $MnCl_2$. In some instances, the hybridization buffer includes Denhardt's solution, dextran sulfate, ficoll, PEG or other hybridization rate accelerators. In some instances, the hybridization buffer includes a carrier such as yeast tRNA, salmon sperm DNA, and/or lambda phage DNA. In some instances, the hybridization buffer includes one or more blockers. In some instances, the hybridization buffer includes RNase inhibitor(s). In some instances, the hybridization buffer can include BSA, sequence specific blockers, non-specific blockers, EDTA, RNase inhibitor(s), betaine, TMAC, or DMSO. In some instances, a hybridization buffer can further include detergents such as Tween, Triton-X 100, sarkosyl, and SDS. In some instances, the hybridization buffer includes nuclease-free water, DEPC water.

In some embodiments, the complementary sequences to which the first probe oligonucleotide and the second probe oligonucleotide bind are 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, about 125, about 150, about 175, about 200, about 250, about 300, about 350, about 400, about 450, about 500, about 600, about 700, about 800, about 900, or about 1000 nucleotides away from each other. Gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, when the first and second probe oligonucleotides are separated from each other by one or more nucleotides, nucleotides are ligated between the first and second probe oligonucleotides. In some embodiments, when the first and second probe oligonucleotides are separated from each other by one or more nucleotides, deoxyribonucleotides are ligated between the first and second probe oligonucleotides.

In some instances, after hybridization, the biological sample is washed with a post-hybridization wash buffer. In some instances, the post-hybridization wash buffer includes one or more of SSC, yeast tRNA, formamide, ethylene carbonate, and nuclease-free water.

Additional embodiments regarding probe hybridization are further provided.

(i) Hybridizing Temperatures

In some embodiments, the method described utilizes oligonucleotides that include deoxyribonucleic acids (instead of strictly utilizing ribonucleotides) at the site of ligation. Utilizing deoxyribonucleic acids in the methods described herein create a more uniform efficiency that can be readily-controlled and flexible for various applications.

In a non-limiting example, the methods disclosed herein include contacting a biological sample with a plurality of oligonucleotides (e.g., probes) including a first oligonucleotide (e.g., a first probe) and a second oligonucleotide (e.g., a second probe), wherein the first oligonucleotide (e.g., the first probe) and the second oligonucleotide (e.g., the second probe) are complementary to a first sequence present in an analyte and a second sequence present in the analyte, respectively; hybridizing the first oligonucleotide (e.g., the first probe) and the second oligonucleotide (e.g., the second probe) to the analyte at a first temperature; hybridizing the first oligonucleotide (e.g., the first probe) and the second oligonucleotide (e.g., the second probe) to a third oligonucleotide (e.g., a splint oligonucleotide) at a second temperature such that the first oligonucleotide (e.g., the first probe) and the second oligonucleotide (e.g., the second probe) abut each other; ligating the first oligonucleotide (e.g., the first probe) to the second oligonucleotide (e.g., the second probe) to create a ligation product; contacting the biological sample with a substrate, wherein a capture probe is immobilized on the substrate, wherein the capture probe includes a spatial barcode and a capture domain; allowing the ligation product to specifically bind to the capture domain; and determining (i) all or a part of the sequence of the ligation product specifically bound to the capture domain, or a complement thereof, and (ii) all or a part of the sequence of the spatial barcode, or a complement thereof, and using the determined sequence of (i) and (ii) to identify the location of the analyte in the biological sample; wherein the first oligonucleotide (e.g., the first probe), the second oligonucleotide (e.g., the second probe), and the third oligonucleotide are DNA oligonucleotides, and wherein the first temperature is a higher temperature than the second temperature.

Figure 11:
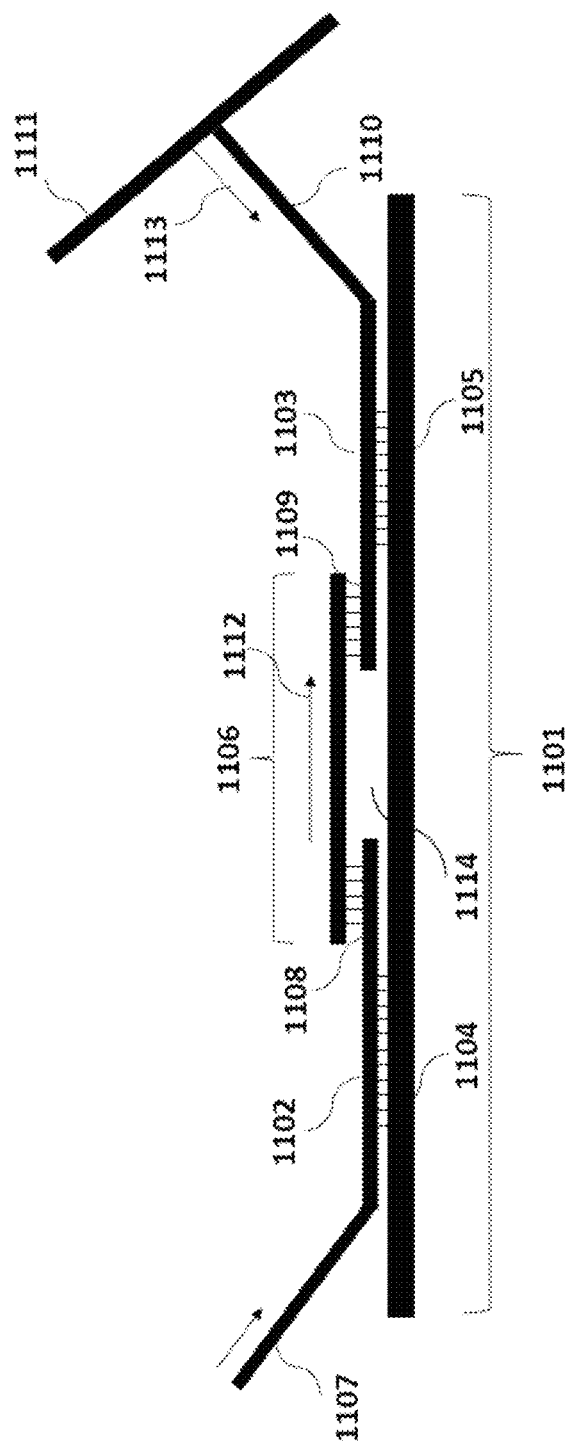
FIG. 11 is a schematic diagram showing an example of an RNA-templated ligation using a first probe oligonucleotide, a second probe oligonucleotide, and a third probe oligonucleotide.

A non-limiting example of this method is shown in FIG. 11. A biological sample including an analyte 1101 is contacted with a first probe 1102 and a second probe 1103. The first probe 1102 and the second probe 1103 hybridize to the analyte at a first target sequence 1104 and a second target sequence 1105, respectively. The first probe and the second probe include free ends 1107-1110. As shown in FIG. 11, the first and second target sequences are not directly adjacent in the analyte. After hybridization, unbound first and second probes are washed away. Then, a third oligonucleotide 1106 hybridizes to the first and the second probes at 1108 and 1109, respectively. After hybridization, the first probe is extended 1112 and a ligation product is created that includes the first probe sequence and the second probe sequence. Alternatively, instead of extending the first probe, the third oligonucleotide is used to "bind" the first probe and the second probe together. In such cases, the first probe and the second probe bound together by the third oligonucleotide can be referred to as a ligation product. The ligation product then is contacted with a substrate 1111, and the ligation product is bound to a capture probe 1113 of the substrate 1111 on the array at distinct spatial positions. In some embodiments, the biological sample is contacted with the substrate 1111 prior to being contacted with the first probe and the second probe.

In some embodiments, the first oligonucleotide (e.g., the first probe) and the second oligonucleotide (e.g., the second probe) hybridize to an analyte at a first temperature. In some embodiments, the first temperature ranges from about 50° C. to about 75° C., from about 55° C. to about 70° C., or from about 60° C. to about 65° C. In some embodiments, the first temperature is about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., or about 70° C.

In some embodiments, after the step of hybridizing the first oligonucleotide (e.g., the first probe) and the second oligonucleotide (e.g., the second probe) to the analyte, a wash step is performed to remove unbound oligonucleotides (e.g., probes). The wash step can be performed using any of the wash methods and solutions described herein.

In some embodiments, after the step of hybridizing the first oligonucleotide (e.g., the first probe) and the second oligonucleotide (e.g., the second probe) to the analyte, a third oligonucleotide (e.g., a splint oligonucleotide) is added to the analyte. In some embodiments, the third oligonucleotide is an oligonucleotide. In some embodiments, the third oligonucleotide is a DNA oligonucleotide.

In some embodiments, the third oligonucleotide includes a sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a portion of the first probe oligonucleotide (e.g., a portion of the first probe that is not hybridized to the analyte (e.g., an auxiliary sequence)). In some embodiments, the third oligonucleotide includes a sequence that is 100% complementary to a portion of the first oligonucleotide (e.g., the first probe). In some embodiments, the third oligonucleotide includes a sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a portion of the second probe oligonucleotide (e.g., a portion of the second probe that is not hybridized to the analyte (e.g., an auxiliary sequence)). In some embodiments, the third oligonucleotide includes a sequence that is 100% complementary to a portion of the second oligonucleotide (e.g., the second probe). In some embodiments, the third oligonucleotide hybridizes to the first oligonucleotide (e.g., the first probe) at the complementary portion. In some embodiments, the third oligonucleotide hybridizes to the second oligonucleotide (e.g., the second probe) at the complementary portion.

In some embodiments, the third oligonucleotide hybridizes to the first oligonucleotide (e.g., the first probe) and to the second oligonucleotide (e.g., the second probe) at a second temperature. In some embodiments, the second temperature is lower than the first temperature at which the first and second oligonucleotides (e.g., the first and second probes) bind the analyte. In some embodiments, the second temperature ranges from about 15° C. to about 35° C., from about 20° C. to about 30° C., or from about 25° C. to about 30° C. In some embodiments, the first temperature is about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., or about 35° C. Methods including a third, or splint, oligonucleotide have been described in U.S. Patent Pub. No. 2019/0055594A1, which is herein incorporated by reference in its entirety.

In some embodiments, after the step of hybridizing the third oligonucleotide to the analyte, a wash step is performed to remove unbound third oligonucleotides. The wash step can be performed using any of the wash methods and solutions described herein. In some embodiments, after the washing step, the first and second oligonucleotides (e.g., the first and second probes) are bound to (e.g., hybridized to) the analyte, and the third oligonucleotide is bound to (e.g., hybridized to) the first and second oligonucleotides (e.g., at portions of the first and second probes that are not bound to the analyte).

In some embodiments, the first oligonucleotide (e.g., the first probe), the second oligonucleotide (e.g., the second probe), and the third oligonucleotide are added to the biological sample at the same time. Then, in some embodiments, the temperature is adjusted to the first temperature to allow the first oligonucleotide (e.g., the first probe) and the second oligonucleotide (e.g., the second probe) to hybridize to the analyte in the biological sample. Next, the temperature is adjusted to the second temperature to allow the third oligonucleotide to hybridize to the first oligonucleotide and the second oligonucleotide.

In some embodiments where a third oligonucleotide hybridizes to a first probe and a second probe that are hybridized to targets sequences that are not directly adjacent in the analyte, the third oligonucleotide is extended to fill the gap between the first probe and the second probe. In some instances, a polymerase (e.g., a DNA polymerase) can extend one of the probes (e.g., the first probe) prior to ligation. For example, as shown in FIG. 11, the first probe 1102 is extended 1112 to fill the gap 1114 between the first probe 1102 and the second probe 1103.

In some embodiments, a ligation step is performed. Ligation can be performed using any of the methods described herein. In some embodiments, the step includes ligation of the first oligonucleotide (e.g., the first probe) and the second oligonucleotide (e.g., the second probe), forming a ligation product. In some embodiments, the third oligonucleotide serves as an oligonucleotide splint to facilitate ligation of the first oligonucleotide (e.g., the first probe) and the second oligonucleotide (e.g., the second probe). In some embodiments, ligation is chemical ligation. In some embodiments, ligation is enzymatic ligation. In some embodiments, the ligase is a T4 RNA ligase (Rnl2), a splintR ligase, a single stranded DNA ligase, or a T4 DNA ligase.

(ii) Hybridization Buffer

In some embodiments, a first probe and a second probe are hybridized to the analyte in a hybridization buffer. In some instances, the hybridization buffer contains formamide. In other instances the hybridization buffer is formamide free. Formamide is not human friendly and it is a known health hazard. Chemically, it can oxidize over time, thereby impacting reagent shelf life and, most importantly, reagent efficacy. As such, the methods described herein can include formamide-free buffers, including formamide-free hybridization buffer.

In some embodiments, the formamide-free hybridization buffer is a saline-sodium citrate (SSC) hybridization buffer. In some embodiment, the SSC is present in the SSC hybridization buffer from about 1×SSC to about 6×SSC (e.g., about 1×SSC to about 5×SSC, about 1×SSC to about 4×SSC, about 1×SSC to about 3×SSC, about 1×SSC to about 2×SSC, about 2×SSC to about 6×SSC, about 2×SSC to about 5×SSC, about 2×SSC to about 4×SSC, about 2×SSC to about 3×SSC, about 3×SSC to about 5×SSC, about 3×SSC to about 4×SSC, about 4×SSC to about 6×SSC, about 4×SSC to about 6×SSC, about 4×SSC to about 5×SSC, or about 5×SSC to about 6×SSC). In some embodiments, the SSC is present in the SSC hybridization buffer from about 2×SSC to about 4×SSC. In some embodiments, SSPE hybridization buffer can be used.

In some embodiments, the SSC hybridization buffer comprises a solvent. In some embodiments, the solvent comprises ethylene carbonate instead of formamide (2020, Kalinka et al., Scientia Agricola 78(4):e20190315). In some embodiments, ethylene carbonate is present in the SSC hybridization buffer from about 10% (w/v) to about 25% (w/v) (e.g., about 10% (w/v) to about 20% (w/v), about 10%

(w/v) to about 15% (w/v), about 15% (w/v) to about 25% (w/v), about 15% (w/v) to about 20% (w/v), or about 20% (w/v) to about 25% (w/v)). In some embodiments, ethylene carbonate is present in the SSC hybridization buffer from about 15% (w/v) to about 20% (w/v). In some embodiments, ethylene carbonate is present in the SSC hybridization buffer at about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), or about 25% (w/v). In some embodiments, ethylene carbonate is present in the SSC hybridization buffer at about 13% (w/v).

In some embodiments, the SSC hybridization buffer is at a temperature from about 40° C. to about 60° C. (e.g., about 40° C. to about 55° C., about 40° C. to about 50° C., about 40° C. to about 45° C., about 45° C. to about 60° C., about 45° C. to about 55° C., about 45° C. to about 50° C., about 50° C. to about 60° C., about 50° C. to about 55° C., or about 55° C. to about 60° C.). In some embodiments, the SSC hybridization buffer is at temperature from about 45° C. to about 55° C., or any of the subranges described herein. In some embodiments, the SSC hybridization buffer is at a temperature of about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., or about 60° C. In some embodiments, the SSC hybridization buffer is at a temperature of about 50° C.

In some embodiments, the SSC hybridization buffer further comprises one or more of a carrier, a crowder, or an additive. Non-limiting examples of a carrier that can be included in the hybridization buffer include: yeast tRNA, salmon sperm DNA, lambda phage DNA, glycogen, and cholesterol. Non-limiting examples of a molecular crowder that can be included in the hybridization buffer include: Ficoll, dextran, Denhardt's solution, and PEG. Non-limiting examples of additives that can be included in the hybridization buffer include: binding blockers, RNase inhibitors, Tm adjustors and adjuvants for relaxing secondary nucleic acid structures (e.g., betaine, TMAC, and DMSO). Further, a hybridization buffer can include detergents such as SDS, Tween, Triton-X 100, and sarkosyl (e.g., N-Lauroylsarcosine sodium salt). A skilled artisan would understand that a buffer for hybridization of nucleic acids could include many different compounds that could enhance the hybridization reaction.

(f) Washing

In some embodiments, the methods disclosed herein also include a wash step. The wash step removes any unbound probes. Wash steps could be performed between any of the steps in the methods disclosed herein. For example, a wash step can be performed after adding probes to the biological sample. As such, free/unbound probes are washed away, leaving only probes that have hybridized to an analyte. In some instances, multiple (i.e., at least 2, 3, 4, 5, or more) wash steps occur between the methods disclosed herein. Wash steps can be performed at times (e.g., 1, 2, 3, 4, or 5 minutes) and temperatures (e.g., room temperature; 4° C. known in the art and determined by a person of skill in the art.

In some instances, wash steps are performed using a wash buffer. In some instances, the wash buffer includes SSC (e.g., 1×SSC). In some instances, the wash buffer includes PBS (e.g., 1×PBS). In some instances, the wash buffer includes PBST (e.g., 1×PBST). In some instances, the wash buffer can also include formamide or be formamide free.

Additional embodiments regarding wash steps are provided herein.

(i) Formamide Free Wash Buffer

In some embodiments, after ligating a first probe and a second probe, the one or more unhybridized first probes, one or more unhybridized second probes, or both, are removed from the array. In some embodiments, after ligating a first probe, one or more spanning probes, and a second probe, the one or more unhybridized first, second, and/or spanning probes, are removed from the array. In some embodiments, after ligating a first probe, a second probe, and a third oligonucleotide, the one or more unhybridized first probes, one or more unhybridized second probes, or one or more third oligonucleotides, or all the above, are removed from the array.

In some embodiments, a pre-hybridization buffer is used to wash the sample. In some embodiments, a phosphate buffer is used. In some embodiments, multiple wash steps are performed to remove unbound oligonucleotides.

In some embodiments, removing includes washing the one or more unhybridized probes (e.g., a first probe, a second probe, a spanning probe, additional spanning probes, and a third oligonucleotide) from the array in a formamide-free wash buffer.

In some embodiments, the formamide-free wash buffer is an SSC wash buffer. In some embodiments, SSC is present in the SSC wash buffer from about 0.01×SSC to about 1×SSC (e.g., about 0.01×SSC to about 0.5×SSC, 0.01×SSC to about 0.1×SSC, about 0.01×SSC to about 0.05×SSC, about 0.05×SSC to about 1×SSC, about 0.05×SSC to about 0.5×SSC, about 0.05×SSC to about 0.1×SSC, about 0.1× SSC to about 1×SSC, about 0.1×SSC to about 0.5×SSC, or about 0.5×SSC to about 1×SSC). In some embodiments, SSC is present in the SSC wash buffer at about 0.01×SSC, about 0.02×SSC, about 0.03×SSC, about 0.04×SSC, about 0.05×SSC, about 0.06×SSC, about 0.07×SSC, about 0.08× SSC, about 0.09×SSC, about 0.1×SSC, about 0.2×SSC, about 0.3×SSC, about 0.4×SSC, about 0.5×SSC, about 0.6× SSC, about 0.7×SSC, about 0.8×SSC, about 0.9×SSC, or about 0.1×SSC. In some embodiments, SSC is present in the SSC wash buffer at about 0.1×SSC.

In some embodiments, the SSC wash buffer comprises a detergent. In some embodiments, the detergent comprises sodium dodecyl sulfate (SDS). In some embodiments, SDS is present in the SSC wash buffer from about 0.01% (v/v) to about 0.5% (v/v) (e.g., about 0.01% (v/v) to about 0.4% (v/v), about 0.01% (v/v) to about 0.3% (v/v), about 0.01% (v/v) to about 0.2% (v/v), about 0.01% (v/v) to about 0.1% (v/v), about 0.05% (v/v) to about 0.5% (v/v), about 0.05% (v/v) to about 0.4% (v/v), about 0.05% (v/v) to about 0.3% (v/v), about 0.05% (v/v) to about 0.2% (v/v), about 0.05% (v/v) to about 0.1% (v/v), about 0.1% (v/v) to about 0.5% (v/v), about 0.1% (v/v) to about 0.4% (v/v), about 0.1% (v/v) to about 0.3% (v/v), about 0.1% (v/v) to about 0.2% (v/v), about 0.2% (v/v) to about 0.5% (v/v), about 0.2% (v/v) to about 0.4% (v/v), about 0.2% (v/v) to about 0.3% (v/v), about 0.3% (v/v) to about 0.5% (v/v), about 0.3% (v/v) to about 0.4% (v/v), or about 0.4% (v/v) to about 0.5% (v/v)). In some embodiments, the SDS is present the SSC wash buffer at about 0.01% (v/v), about 0.02% (v/v), about 0.03% (v/v), about 0.04% (v/v), about 0.05% (v/v), about 0.06% (v/v), about 0.07% (v/v), about 0.08% (v/v), about 0.09% (v/v), about 0.10% (v/v), about 0.2% (v/v), about 0.3% (v/v), about 0.4% (v/v), or about 0.5% (v/v), In some embodiments, the SDS is present in the SSC wash buffer at about 0.1% (v/v). In some embodiments, sarkosyl may be present in the SSC wash buffer.

In some embodiments, the SSC wash buffer comprises a solvent. In some embodiments, the solvent comprises ethylene carbonate. In some embodiments, ethylene carbonate is present in the SSC wash buffer from about 10% (w/v) to about 25% (w/v), or any of the subranges described herein. In some embodiments, ethylene carbonate is present in the SSC wash buffer from about 15% (w/v) to about 20% (w/v). In some embodiments, ethylene carbonate is present in the SSC wash buffer at about 16% (w/v).

In some embodiments, the SSC wash buffer is at a temperature from about 50° C. to about 70° C. (e.g., about 50° C. to about 65° C., about 50° C. to about 60° C., about 50° C. to about 55° C., about 55° C. to about 70° C., about 55° C. to about 65° C., about 55° C. to about 60° C., about 60° C. to about 70° C., about 60° C. to about 65° C., or about 65° C. to about 70° C.). In some embodiments, the SSC wash buffer is at a temperature from about 55° C. to about 65° C. In some embodiments, the SSC wash buffer is at a temperature about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., or about 70° C. In some embodiments, the SSC wash buffer is at a temperature of about 60° C.

In some embodiments, the method includes releasing the ligation product, where releasing is performed after the array is washed to remove the one or more unhybridized first and second probes.

(g) Ligation

In some embodiments, after hybridization of the probe oligonucleotides (e.g., a first probe, a second probe, a spanning probe, additional spanning probes, and/or a third oligonucleotide) to the analyte, the probe (e.g., a first probe, a second probe, a spanning probe, additional spanning probes, and/or a third oligonucleotide) can be ligated together, creating a single ligation product that includes one or more sequences that are complementary to the analyte. Ligation can be performed enzymatically or chemically, as described herein.

In some instances, the ligation is an enzymatic ligation reaction, using a ligase (e.g., T4 RNA ligase (Rnl2), a SplintR ligase, a single stranded DNA ligase, or a T4 DNA ligase). See, e.g., Zhang et al.; *RNA Biol.* 2017; 14(1): 36-44, which is incorporated by reference in its entirety, for a description of KOD ligase. Following the enzymatic ligation reaction, the probes (e.g., a first probe, a second probe, a spanning probe, additional spanning probes, and/or a third oligonucleotide) may be considered ligated.

In some embodiments, a polymerase catalyzes synthesis of a complementary strand of the ligation product, creating a double-stranded ligation product. In some instances, the polymerase is DNA polymerase. In some embodiments, the polymerase has 5' to 3' polymerase activity. In some embodiments, the polymerase has 3' to 5' exonuclease activity for proofreading. In some embodiments, the polymerase has 5' to 3' polymerase activity and 3' to 5' exonuclease activity for proofreading.

In some embodiments, the probe (e.g., a first probe, a second probe, a spanning probe, additional spanning probes, and/or a third oligonucleotide) may each comprise a reactive moiety such that, upon hybridization to the target and exposure to appropriate ligation conditions, the probe oligonucleotides may ligate to one another. In some embodiments, probe oligonucleotides that include a reactive moiety are ligated chemically. For example, a first probe capable of hybridizing to a first target region (e.g., a first target sequence or a first portion) of a nucleic acid molecule may comprise a first reactive moiety, and a second probe oligonucleotide capable of hybridizing to a second target region (e.g., a second target sequence or a second portion) of the nucleic acid molecule may comprise a second reactive moiety. When the first and second probes are hybridized to the first and second target regions (e.g., first and second target sequences) of the nucleic acid molecule, the first and second reactive moieties may be adjacent to one another. A reactive moiety of a probe may be selected from the non-limiting group consisting of azides, alkynes, nitrones (e.g., 1,3-nitrones), strained alkenes (e.g., trans-cycloalkenes such as cyclooctenes or oxanorbornadiene), tetrazines, tetrazoles, iodides, thioates (e.g., phorphorothioate), acids, amines, and phosphates. For example, the first reactive moiety of a first probe may comprise an azide moiety, and a second reactive moiety of a second probe may comprise an alkyne moiety. The first and second reactive moieties may react to form a linking moiety. A reaction between the first and second reactive moieties may be, for example, a cycloaddition reaction such as a strain-promoted azide-alkyne cycloaddition, a copper-catalyzed azide-alkyne cycloaddition, a strain-promoted alkyne-nitrone cycloaddition, a Diels-Alder reaction, a [3+2] cycloaddition, a [4+2] cycloaddition, or a [4+1] cycloaddition; a thiol-ene reaction; a nucleophilic substation reaction; or another reaction. In some cases, reaction between the first and second reactive moieties may yield a triazole moiety or an isoxazoline moiety. A reaction between the first and second reactive moieties may involve subjecting the reactive moieties to suitable conditions such as a suitable temperature, pH, or pressure and providing one or more reagents or catalysts for the reaction. For example, a reaction between the first and second reactive moieties may be catalyzed by a copper catalyst, a ruthenium catalyst, or a strained species such as a difluorooctyne, dibenzylcyclooctyne, or biarylazacyclooctynone. Reaction between a first reactive moiety of a first probe hybridized to a first target region (e.g., a first target sequence or first portion) of the nucleic acid molecule and a second reactive moiety of a third probe oligonucleotide hybridized to a second target region (e.g., a first target sequence or a first portion) of the nucleic acid molecule may link the first probe and the second probe to provide a ligated probe. Upon linking, the first and second probe may be considered ligated. Accordingly, reaction of the first and second reactive moieties may comprise a chemical ligation reaction such as a copper-catalyzed 5' azide to 3' alkyne "click" chemistry reaction to form a triazole linkage between two probe oligonucleotides. In other non-limiting examples, an iodide moiety may be chemically ligated to a phosphorothioate moiety to form a phosphorothioate bond, an acid may be ligated to an amine to form an amide bond, and/or a phosphate and amine may be ligated to form a phosphoramidate bond.

Figure 12A:
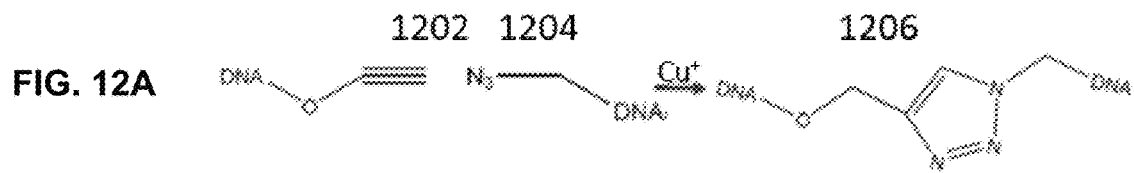
FIGS. 12A-12E show various approaches for chemically-mediated nucleic acid ligation.
Figure 12B:
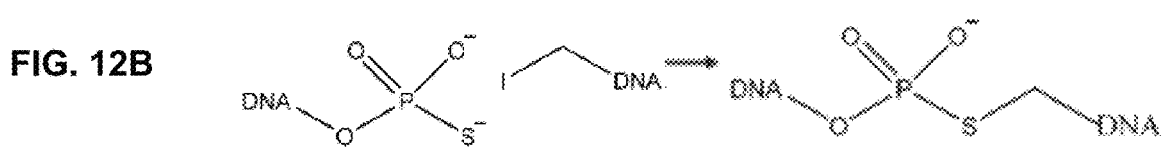
Figure 12C:
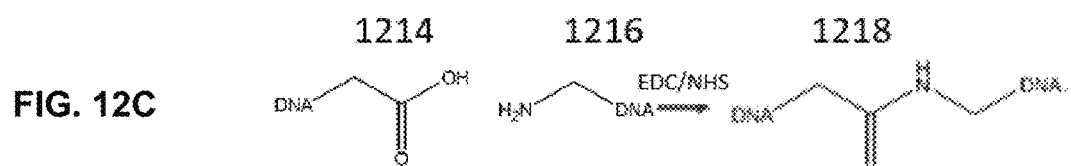
Figure 12D:
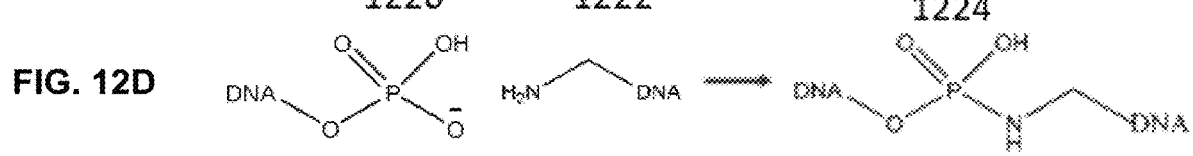
Figure 12E:
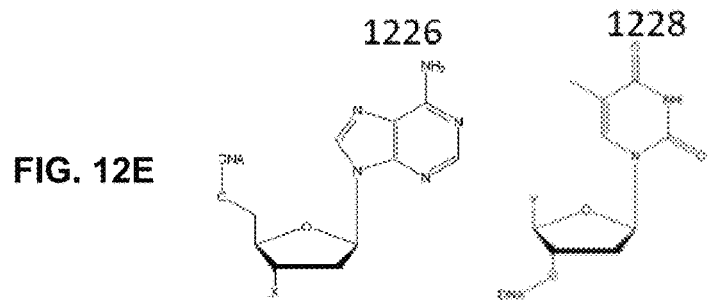

FIGS. 12A-12E illustrates examples of representative reactions. FIG. 12A shows a chemical ligation reaction of an alkyne moiety 1202 and an azide moiety 1204 reacting under copper-mediated cycloaddition to form a triazole linkage 1206. FIG. 12B shows a chemical ligation reaction of a phosphorothioate group 1208 with an iodide group 1210 to form a phosphorothioate linkage 1212. FIG. 12C shows a chemical ligation reaction of an acid 1214 and amine 1216 to form an amide linkage 1218. FIG. 12D shows a chemical ligation reaction of a phosphate moiety 1220 and an amine moiety 1222 to form a phosphoramidate linkage 1224. FIG. 12E shows a conjugation reaction of two species 1226 and 1228.

In some instances, ligation is performed in a ligation buffer. In instances where probe ligation is performed on diribo-containing probes, the ligation buffer can include T4 RNA Ligase Buffer 2, enzyme (e.g., RNL2 ligase), and nuclease free water. In instances where probe ligation is performed on DNA probes, the ligation buffer can include Tris-HCl pH7.5, MnCl2, ATP, DTT, surrogate fluid (e.g., glycerol), enzyme (e.g., SplintR ligase), and nuclease-free water.

In some embodiments, the ligation buffer includes additional reagents. In some instances, the ligation buffer includes adenosine triphosphate (ATP) is added during the ligation reaction. DNA ligase-catalyzed sealing of nicked DNA substrates is first activated through ATP hydrolysis, resulting in covalent addition of an AMP group to the enzyme. After binding to a nicked site in a DNA duplex, the ligase transfers the AMP to the phosphorylated 5'-end at the nick, forming a 5'-5' pyrophosphate bond. Finally, the ligase catalyzes an attack on this pyrophosphate bond by the OH group at the 3'-end of the nick, thereby sealing it, whereafter ligase and AMP are released. If the ligase detaches from the substrate before the 3' attack, e.g. because of premature AMP reloading of the enzyme, then the 5' AMP is left at the 5'-end, blocking further ligation attempts. In some instances, ATP is added at a concentration of about 10 µM, about 100 µM, about 1000 µM, or about 10000 µM during the ligation reaction.

In some embodiments, cofactors that aid in joining of the probe oligonucleotides are added during the ligation process. In some instances, the cofactors include magnesium ions ($Mg^{2+}$). In some instances, the cofactors include manganese ions ($Mn^{2+}$). In some instances, $Mg^{2+}$ is added in the form of $MgCl_2$. In some instances, $Mn^{2+}$ is added in the form of $MnCl_2$. In some instances, the concentration of $MgCl_2$ is at about 1 mM, at about 10 mM, at about 100 mM, or at about 1000 mM. In some instances, the concentration of $MnCl_2$ is at about 1 mM, at about 10 mM, at about 100 mM, or at about 1000 mM.

In some embodiments, the ligation product includes a capture probe capture domain, which can bind to a capture probe (e.g., a capture probe immobilized, directly or indirectly, on a substrate). In some embodiments, methods provided herein include contacting a biological sample with a substrate, wherein the capture probe is affixed to the substrate (e.g., immobilized to the substrate, directly or indirectly). In some embodiments, the capture probe capture domain of the ligated probe specifically binds to the capture domain.

After ligation, in some instances, the biological sample is washed with a post-ligation wash buffer. In some instances, the post-ligation wash buffer includes one or more of SSC (e.g., 1×SSC), ethylene carbonate or formamide, and nuclease free water. In some instances, the biological sample is washed at this stage at about 50° C. to about 70° C. In some instances, the biological sample is washed at about 60° C.

(i) Ligation Including Pre-Adenylated 5' Phosphate on Second Probe

Provided herein are methods for determining a location of a target nucleic acid in a biological sample that include: (a) contacting the biological sample with a substrate comprising a plurality of capture probes, where a capture probe of the plurality of capture probes comprises a capture domain and a spatial barcode; (b) hybridizing a target nucleic acid in the biological sample with a first probe and a second probe, where the first probe comprises, from 3' to 5', a sequence substantially complementary to the capture domain and a sequence that is substantially complementary to a first sequence in the target nucleic acid and has a pre-adenylated phosphate group at its 5' end; the second probe comprises a sequence substantially complementary to a second sequence in the target nucleic acid; (c) generating a ligation product by ligating a 3' end of the second probe to the 5' end of the first probe using a ligase that does not require adenosine triphosphate for ligase activity; (d) releasing the ligation product from the target nucleic acid and binding the capture domain of the ligation product specifically to the capture domain of capture probe; and (e) determining (i) all or a part of a sequence corresponding to the ligation product, or a complement thereof, and (ii) all or a part of a sequence corresponding to the spatial barcode, or a complement thereof, and using the determined sequences of (i) and (ii) to identify the location of the target nucleic acid in the biological sample In some instances, the ligase that does not require adenosine triphosphate for ligase activity (e.g., thermostable 5' AppDNA/RNA Ligase, truncated T4 RNA Ligase 2 (trRnl2), truncated T4 RNA Ligase 2 K227Q, truncated T4 RNA Ligase 2 KQ, *Chlorella* Virus PBCV-1 DNA Ligase, and combinations thereof). See, e.g., Nichols et al., "RNA Ligases," Curr. Protocol. Molec. Biol. 84(1):3.15.1-0.4 (2008); Viollet et al., "T4 RNA Ligase 2 Truncated Active Site Mutants: Improved Tools for RNA Analysis," BMC Biotechnol. 11: 72 (2011); and Ho et al., "Bacteriophage T4 RNA Ligase 2 (gp24.1) Exemplifies a Family of RNA Ligases Found in All Phylogenetic Domains," PNAS 99(20):12709-14 (2002), which are hereby incorporated by reference in their entirety for a description of T4 RNA Ligases and truncated T4 RNA Ligases. Thermostable 5' AppDNA/RNA Ligase is an enzyme belonging to the Ligase family that catalyzes the ligation of the 3' end of ssRNA or ssDNA to a 5'-adenylated ssDNA or 5'-adenylated ssRNA. Truncated T4 RNA Ligase 2 is an enzyme belonging to the Ligase family that catalyzes the ligation of dsRNA nicks and ssRNA to ssRNA. It can also ligate the 3' end of RNA or DNA to a 5'-pDNA when annealed to an RNA complement, and the 3' end of RNA to a 5'-pRNA when annealed to a DNA complement, with reduced efficiency. Truncated T4 RNA Ligase 2 K227Q is an enzyme belonging to the Ligase family that catalyzes the ligation of the 3' end of ssRNA to 5' adenylated ssDNA and 5' adenylated ssRNA. It has a reduction of side products as compared to truncated T4 RNA Ligase 2. Truncated T4 RNA Ligase 2 KQ is an enzyme belonging to the Ligase family that catalyzes the ligation of the 3' end of ssRNA to 5' adenylated ssDNA and 5' adenylated ssRNA. It is a preferred choice for ligation of ssRNA to preadenylated adapters and has a reduction of side products as compared to truncated T4 RNA Ligase 2.

In some embodiments, the T4 RNA Ligase comprises a K227Q mutation. See Viollet et al., "T4 RNA Ligase 2 Truncated Active Site Mutants: Improved Tools for RNA Analysis," *BMC Biotechnol.* 11, which is hereby incorporated by reference in its entirety.

In some instances, cofactors that aid in ligation of the first and second probe are added during ligation. In some instances, the cofactors include magnesium ions ($Mg^{2+}$). In some instances, the cofactors include manganese ions ($Mn^{2+}$). In some instances, $Mg^{2+}$ is added in the form of $MgCl_2$. In some instances, $Mn^{2+}$ is added in the form of $MnCl_2$. In some instances, the concentration of $MgCl_2$ is at about 1 mM to about 10 mM. In some instances, the concentration of $MnCl_2$ is at about 1 mM to about 10 mM.

In some instances, the ligation occurs at a pH in the range of about 6.5 to about 9.0, about 6.5 to about 8.0, or about 7.5 to about 8.0.

In some embodiments, the ligation buffer includes an enzyme storage buffer. In some embodiments, the enzymes storage buffer includes glycerol. In some embodiments, the ligation buffer is supplemented with glycerol. In some embodiments, the glycerol is present in the ligation buffer at a total volume of 15% v/v.

(h) Permeabilization and Releasing the Ligation Product

In some embodiments, the methods provided herein include a permeabilizing step. In some embodiments, permeabilization occurs using a protease. In some embodiments, the protease is an endopeptidase. Endopeptidases that can be used include but are not limited to trypsin, chymotrypsin, elastase, thermolysin, pepsin, clostripan, glutamyl endopeptidase (GluC), ArgC, peptidyl-asp endopeptidase (ApsN), endopeptidase LysC and endopeptidase LysN. In some embodiments, the endopeptidase is pepsin. In some embodiments, after creating a ligation product (e.g., by ligating a first probe and a second probe that are hybridized to adjacent sequences in the analyte), the biological sample is permeabilized. In some embodiments, the biological sample is permeabilized contemporaneously with or prior to contacting the biological sample with a first probe and a second probe, hybridizing the first probe and the second probe to the analyte, generating a ligation product by ligating the first probe and the second probe, and releasing the ligated product from the analyte.

In some embodiments, methods provided herein include permeabilization of the biological sample such that the capture probe can more easily bind to the captured ligated probe (i.e., compared to no permeabilization). In some embodiments, reverse transcription (RT) reagents can be added to permeabilized biological samples. Incubation with the RT reagents can produce spatially-barcoded full-length cDNA from the captured analytes (e.g., polyadenylated mRNA). Second strand reagents (e.g., second strand primers, enzymes) can be added to the biological sample on the slide to initiate second strand synthesis.

In some instances, the permeabilization step includes application of a permeabilization buffer to the biological sample. In some instances, the permeabilization buffer includes a buffer (e.g., Tris pH 7.5), MgCl2, sarkosyl detergent (e.g., sodium lauroyl sarcosinate), enzyme (e.g., proteinase K, and nuclease free water. In some instances, the permeabilization step is performed at 37° C. In some instances, the permeabilization step is performed for about 20 minutes to 2 hours (e.g., about 20 minutes, about 30 minutes, about 40 minutes, about 50 minutes, about 1 hour, about 1.5 hours, or about 2 hours). In some instances, the releasing step is performed for about 40 minutes.

In some instances, after generating a ligation product, the ligation product is released from the analyte. In some embodiments, a ligation product is released from the analyte using an endoribonuclease. In some embodiments, the endoribonuclease is RNase H, RNase A, RNase C, or RNase I. In some embodiments, the endoribonuclease is RNase H. RNase H is an endoribonuclease that specifically hydrolyzes the phosphodiester bonds of RNA, when hybridized to DNA. RNase H is part of a conserved family of ribonucleases which are present in many different organisms. There are two primary classes of RNase H: RNase H1 and RNase H2. Retroviral RNase H enzymes are similar to the prokaryotic RNase H1. All of these enzymes share the characteristic that they are able to cleave the RNA component of an RNA:DNA heteroduplex. In some embodiments, the RNase H is RNase H1, RNase H2, or RNase H1, or RNase H2. In some embodiments, the RNase H includes but is not limited to RNase HII from *Pyrococcus furiosus*, RNase HII from *Pyrococcus horikoshi*, RNase HI from *Thermococcus litoralis*, RNase HI from *Thermus thermophilus*, RNAse HI from *E. coli*, or RNase HII from *E. coli*.

In some instances, the releasing step is performed using a releasing buffer. In some instances, the release buffer includes one or more of a buffer (e.g., Tris pH 7.5), enzyme (e.g., RNAse H) and nuclease-free water. In some instances, the releasing step is performed at 37° C. In some instances, the releasing step is performed for about 20 minutes to 2 hours (e.g., about 20 minutes, about 30 minutes, about 40 minutes, about 50 minutes, about 1 hour, about 1.5 hours, or about 2 hours). In some instances, the releasing step is performed for about 30 minutes.

In some instances, the releasing step occurs before the permeabilization step. In some instances, the releasing step occurs after the permeabilization step. In some instances, the releasing step occurs at the same time as the permeabilization step (e.g., in the same buffer).

(i) Blocking Probes

In some embodiments, a capture probe capture domain is blocked prior to adding a second probe oligonucleotide to a biological sample. This prevents the capture probe capture domain from prematurely hybridizing to the capture domain.

In some embodiments, a blocking probe is used to block or modify the free 3' end of the capture probe capture domain. In some embodiments, a blocking probe can be hybridized to the capture probe capture domain of the second probe to mask the free 3' end of the capture probe capture domain. In some embodiments, a blocking probe can be a hairpin probe or partially double stranded probe. In some embodiments, the free 3' end of the capture probe capture domain of the second probe can be blocked by chemical modification, e.g., addition of an azidomethyl group as a chemically reversible capping moiety such that the capture probes do not include a free 3' end. Blocking or modifying the capture probe capture domain, particularly at the free 3' end of the capture probe capture domain, prior to contacting second probe with the substrate, prevents hybridization of the second probe to the capture domain (e.g., prevents the capture of a poly(A) of a capture probe capture domain to a poly(T) capture domain). In some embodiments, a blocking probe can be referred to as a capture probe capture domain blocking moiety.

In some embodiments, the blocking probes can be reversibly removed. For example, blocking probes can be applied to block the free 3' end of either or both the capture probe capture domain and/or the capture probes. Blocking interaction between the capture probe capture domain and the capture probe on the substrate can reduce non-specific capture to the capture probes. After the second probe hybridizes to the analyte and is ligated to a first probe, one or more spanning probes, or a third oligonucleotide, the blocking probes can be removed from the 3' end of the capture probe capture domain and/or the capture probe, and the ligation product can migrate to and become bound by the capture probes on the substrate. In some embodiments, the removal includes denaturing the blocking probe from capture probe capture domain and/or capture probe. In some embodiments, the removal includes removing a chemically reversible capping moiety. In some embodiments, the removal includes digesting the blocking probe with an RNase (e.g., RNase H).

In some embodiments, the blocking probes are oligo (dT) blocking probes. In some embodiments, the oligo (dT) blocking probes can have a length of 15-30 nucleotides. In some embodiments, the oligo (dT) blocking probes can have a length of 10-50 nucleotides, e.g., 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45, or 45-50 nucleotides. In some embodiments, the analyte capture agents can be blocked at different temperatures (e.g., 4° C. and 37° C.).

(j) Biological Samples

Methods disclosed herein can be performed on any type of sample. In some embodiments, the sample is a fresh tissue. In some embodiments, the sample is a frozen sample. In some embodiments, the sample was previously frozen. In some embodiments, the sample is a formalin-fixed, paraffin embedded (FFPE) sample.

Subjects from which biological samples can be obtained can be healthy or asymptomatic individuals, individuals that have or are suspected of having a disease (e.g., cancer) or a pre-disposition to a disease, and/or individuals that are in need of therapy or suspected of needing therapy. In some instances, the biological sample can include one or more diseased cells. A diseased cell can have altered metabolic properties, gene expression, protein expression, and/or morphologic features. Examples of diseases include inflammatory disorders, metabolic disorders, nervous system disorders, and cancer. In some instances, the biological sample includes cancer or tumor cells. Cancer cells can be derived from solid tumors, hematological malignancies, cell lines, or obtained as circulating tumor cells. In some instances, the biological sample is a heterogenous sample. In some instances, the biological sample is a heterogenous sample that includes tumor or cancer cells and/or stromal cells, In some instances, the cancer is breast cancer. In some instances, the breast cancer is triple positive breast cancer (TPBC). In some instances, the breast cancer is triple negative breast cancer (TNBC).

In some instances, the cancer is colorectal cancer. In some instances, the cancer is ovarian cancer. In certain embodiments, the cancer is squamous cell cancer, small-cell lung cancer, non-small cell lung cancer, gastrointestinal cancer, Hodgkin's or non-Hodgkin's lymphoma, pancreatic cancer, glioblastoma, glioma, cervical cancer, ovarian cancer, liver cancer, bladder cancer, breast cancer, colon cancer, colorectal cancer, endometrial carcinoma, myeloma, salivary gland carcinoma, kidney cancer, basal cell carcinoma, melanoma, prostate cancer, vulval cancer, thyroid cancer, testicular cancer, esophageal cancer, or a type of head or neck cancer. In certain embodiments, the cancer treated is desmoplastic melanoma, inflammatory breast cancer, thymoma, rectal cancer, anal cancer, or surgically treatable or non-surgically treatable brain stem glioma. In some embodiments, the subject is a human.

FFPE samples generally are heavily cross-linked and fragmented, and therefore this type of sample allows for limited RNA recovery using conventional detection techniques. In certain embodiments, methods of targeted RNA capture provided herein are less affected by RNA degradation associated with FFPE fixation than other methods (e.g., methods that take advantage of oligo-dT capture and reverse transcription of mRNA). In certain embodiments, methods provided herein enable sensitive measurement of specific genes of interest that otherwise might be missed with a whole transcriptomic approach.

In some instances, FFPE samples are stained (e.g., using H&E). The methods disclosed herein are compatible with H&E will allow for morphological context overlaid with transcriptomic analysis. However, depending on the need some samples may be stained with only a nuclear stain, such as staining a sample with only hematoxylin and not eosin, when location of a cell nucleus is needed.

In some embodiments, a biological sample (e.g. tissue section) can be fixed with methanol, stained with hematoxylin and eosin, and imaged. In some embodiments, fixing, staining, and imaging occurs before one or more probes are hybridized to the sample. Some embodiments of any of the workflows described herein can further include a destaining step (e.g., a hematoxylin and eosin destaining step), after imaging of the sample and prior to permeabilizing the sample. For example, destaining can be performed by performing one or more (e.g., one, two, three, four, or five) washing steps (e.g., one or more (e.g., one, two, three, four, or five) washing steps performed using a buffer including HCl). The images can be used to map spatial gene expression patterns back to the biological sample. A permeabilization enzyme can be used to permeabilize the biological sample directly on the slide.

In some embodiments, the FFPE sample is deparaffinized, permeabilized, equilibrated, and blocked before target probe oligonucleotides are added. In some embodiments, deparaffinization using xylenes. In some embodiments, deparaffinization includes multiple washes with xylenes. In some embodiments, deparaffinization includes multiple washes with xylenes followed by removal of xylenes using multiple rounds of graded alcohol followed by washing the sample with water. In some aspects, the water is deionized water. In some embodiments, equilibrating and blocking includes incubating the sample in a pre-Hyb buffer. In some embodiments, the pre-Hyb buffer includes yeast tRNA. In some embodiments, permeabilizing a sample includes washing the sample with a phosphate buffer. In some embodiments, the buffer is PBS. In some embodiments, the buffer is PBST.

(k) Determining the Sequence of the Ligation Product

After a ligation product from the sample has hybridized or otherwise been associated with a capture probe according to any of the methods described above in connection with the general spatial cell-based analytical methodology, the barcoded constructs that result from hybridization/association are analyzed.

In some embodiments, after contacting a biological sample with a substrate that includes capture probes, a removal step can optionally be performed to remove all or a portion of the biological sample from the substrate. In some embodiments, the removal step includes enzymatic and/or chemical degradation of cells of the biological sample. For example, the removal step can include treating the biological sample with an enzyme (e.g., a proteinase, e.g., proteinase K) to remove at least a portion of the biological sample from the substrate. In some embodiments, the removal step can include ablation of the tissue (e.g., laser ablation).

In some embodiments, provided herein are methods for spatially detecting an analyte (e.g., detecting the location of an analyte, e.g., a biological analyte) from a biological sample (e.g., present in a biological sample), the method comprising: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; wherein the biological sample is fully or partially removed from the substrate.

In some embodiments, a biological sample is not removed from the substrate. For example, the biological sample is not removed from the substrate prior to releasing a capture probe (e.g., a capture probe bound to an analyte) from the substrate. In some embodiments, such releasing comprises cleavage of the capture probe from the substrate (e.g., via a cleavage domain). In some embodiments, such releasing does not comprise releasing the capture probe from the substrate (e.g., a copy of the capture probe bound to an analyte can be made and the copy can be released from the substrate, e.g., via denaturation). In some embodiments, the biological sample is not removed from the substrate prior to analysis of an analyte bound to a capture probe after it is released from the substrate. In some embodiments, the biological sample remains on the substrate during removal of a capture probe from the substrate and/or analysis of an analyte bound to the capture probe after it is released from the substrate. In some embodiments, the biological sample remains on the substrate during removal (e.g., via denaturation) of a copy of the capture probe (e.g., complement). In some embodiments, analysis of an analyte bound to capture probe from the substrate can be performed without subjecting the biological sample to enzymatic and/or chemical degradation of the cells (e.g., permeabilized cells) or ablation of the tissue (e.g., laser ablation).

In some embodiments, at least a portion of the biological sample is not removed from the substrate. For example, a portion of the biological sample can remain on the substrate prior to releasing a capture probe (e.g., a capture prove bound to an analyte) from the substrate and/or analyzing an analyte bound to a capture probe released from the substrate. In some embodiments, at least a portion of the biological sample is not subjected to enzymatic and/or chemical degradation of the cells (e.g., permeabilized cells) or ablation of the tissue (e.g., laser ablation) prior to analysis of an analyte bound to a capture probe from the substrate.

In some embodiments, provided herein are methods for spatially detecting an analyte (e.g., detecting the location of an analyte, e.g., a biological analyte) from a biological sample (e.g., present in a biological sample) that include: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; where the biological sample is not removed from the substrate.

In some embodiments, provided herein are methods for spatially detecting a biological analyte of interest from a biological sample that include: (a) staining and imaging a biological sample on a substrate; (b) providing a solution comprising a permeabilization reagent to the biological sample on the substrate; (c) contacting the biological sample with an array on a substrate, wherein the array comprises one or more capture probe pluralities thereby allowing the one or more pluralities of capture probes to capture the biological analyte of interest; and (d) analyzing the captured biological analyte, thereby spatially detecting the biological analyte of interest; where the biological sample is not removed from the substrate.

In some embodiments, the method further includes subjecting a region of interest in the biological sample to spatial transcriptomic analysis. In some embodiments, one or more of the capture probes includes a capture domain. In some embodiments, one or more of the capture probes comprises a unique molecular identifier (UMI). In some embodiments, one or more of the capture probes comprises a cleavage domain. In some embodiments, the cleavage domain comprises a sequence recognized and cleaved by a uracil-DNA glycosylase, apurinic/apyrimidinic (AP) endonuclease (APE1), U uracil-specific excision reagent (USER), and/or an endonuclease VIII. In some embodiments, one or more capture probes do not comprise a cleavage domain and is not cleaved from the array.

In some embodiments, a capture probe can be extended (an "extended capture probe," e.g., as described herein). For example, extending a capture probe can include generating cDNA from a captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending a capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, a capture domain of a capture probe includes a primer for producing the complementary strand of a nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA (e.g., cDNA) molecule is generated. In some embodiments, a "full-length" DNA molecule refers to the whole of the captured nucleic acid molecule. However, if a nucleic acid (e.g., RNA) was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Lucigen, Middleton, Wis.). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9° N) DNA ligase (9° N™ DNA ligase, New England Biolabs), Ampligase™ (available from Lucigen, Middleton, Wis.), and SplintR (available from New England Biolabs, Ipswich, Mass.). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g., sequence analysis.

This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probe includes the affinity group. The affinity group can correspond to any of the affinity groups described previously.

In some embodiments, the extended capture probes including the affinity group can be coupled to a substrate specific for the affinity group. In some embodiments, the substrate can include an antibody or antibody fragment. In some embodiments, the substrate includes avidin or streptavidin and the affinity group includes biotin. In some embodiments, the substrate includes maltose and the affinity group includes maltose-binding protein. In some embodiments, the substrate includes maltose-binding protein and the affinity group includes maltose. In some embodiments, amplifying the extended capture probes can function to release the extended probes from the surface of the substrate, insofar as copies of the extended probes are not immobilized on the substrate.

In some embodiments, the extended capture probe or complement or amplicon thereof is released. The step of releasing the extended capture probe or complement or amplicon thereof from the surface of the substrate can be achieved in a number of ways. In some embodiments, an extended capture probe or a complement thereof is released from the array by nucleic acid cleavage and/or by denaturation (e.g., by heating to denature a double-stranded molecule).

In some embodiments, the extended capture probe or complement or amplicon thereof is released from the surface of the substrate (e.g., array) by physical means. For example, where the extended capture probe is indirectly immobilized on the array substrate, e.g., via hybridization to a surface probe, it can be sufficient to disrupt the interaction between the extended capture probe and the surface probe. Methods for disrupting the interaction between nucleic acid molecules include denaturing double stranded nucleic acid molecules are known in the art. A straightforward method for releasing the DNA molecules (i.e., of stripping the array of extended probes) is to use a solution that interferes with the hydrogen bonds of the double stranded molecules. In some embodiments, the extended capture probe is released by an applying heated solution, such as water or buffer, of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the substrate.

In some embodiments, where the extended capture probe includes a cleavage domain, the extended capture probe is released from the surface of the substrate by cleavage. For example, the cleavage domain of the extended capture probe can be cleaved by any of the methods described herein. In some embodiments, the extended capture probe is released from the surface of the substrate, e.g., via cleavage of a cleavage domain in the extended capture probe, prior to the step of amplifying the extended capture probe.

In some embodiments, probes complementary to the extended capture probe can be contacted with the substrate. In some embodiments, the biological sample can be in contact with the substrate when the probes are contacted with the substrate. In some embodiments, the biological sample can be removed from the substrate prior to contacting the substrate with probes. In some embodiments, the probes can be labeled with a detectable label (e.g., any of the detectable labels described herein). In some embodiments, probes that do not specially bind (e.g., hybridize) to an extended capture probe can be washed away. In some embodiments, probes complementary to the extended capture probe can be detected on the substrate (e.g., imaging, any of the detection methods described herein).

In some embodiments, probes complementary to an extended capture probe can be about 4 nucleotides to about 100 nucleotides long. In some embodiments, probes (e.g., detectable probes) complementary to an extended capture probe can be about 10 nucleotides to about 90 nucleotides long. In some embodiments, probes (e.g., detectable probes) complementary to an extended capture probe can be about 20 nucleotides to about 80 nucleotides long. In some embodiments, probes (e.g., detectable probes) complementary to an extended capture probe can be about 30 nucleotides to about 60 nucleotides long. In some embodiments, probes (e.g., detectable probes) complementary to an extended capture probe can be about 40 nucleotides to about 50 nucleotides long. In some embodiments, probes (e.g., detectable probes) complementary to an extended capture probe can be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 nucleotides long.

In some embodiments, about 1 to about 100 probes can be contacted to the substrate and specifically bind (e.g., hybridize) to an extended capture probe. In some embodiments, about 1 to about 10 probes can be contacted to the substrate and specifically bind (e.g., hybridize) to an extended capture probe. In some embodiments, about 10 to about 100 probes can be contacted to the substrate and specifically bind (e.g., hybridize) to an extended capture probe. In some embodiments, about 20 to about 90 probes can be contacted to the substrate and specifically bind (e.g., hybridize) to an extended capture probe. In some embodiments, about 30 to about 80 probes (e.g., detectable probes) can be contacted to the substrate and specifically bind (e.g., hybridize) to an extended capture probe. In some embodiments, about 40 to about 70 probes can be contacted to the substrate and specifically bind (e.g., hybridize) to an extended capture probe. In some embodiments, about 50 to about 60 probes can be contacted to the substrate and specifically bind (e.g., hybridize) to an extended capture probe. In some embodiments, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 probes can be contacted to the substrate and specifically bind (e.g., hybridize) to an extended capture probe.

In some embodiments, the probes can be complementary to a single analyte (e.g., a single gene). In some embodiments, the probes can be complementary to one or more analytes (e.g., analytes in a family of genes). In some embodiments, the probes (e.g., detectable probes) can be for a panel of genes associated with a disease (e.g., cancer, Alzheimer's disease, Parkinson's disease).

In some instances, the ligated probe and capture probe can be amplified or copied, creating a plurality of cDNA molecules. In some embodiments, cDNA can be denatured from the capture probe template and transferred (e.g., to a clean tube) for amplification, and/or library construction. The spatially-barcoded cDNA can be amplified via PCR prior to library construction. The cDNA can then be enzymatically fragmented and size-selected in order to optimize for cDNA amplicon size. P5 and P7 sequences directed to capturing the amplicons on a sequencing flowcell (Illumina sequencing instruments) can be appended to the amplicons, i7, and i5 can be used as sample indexes, and TruSeq Read 2 can be added via End Repair, A-tailing, Adaptor Ligation, and PCR. The cDNA fragments can then be sequenced using paired-end sequencing using TruSeq Read 1 and TruSeq Read 2 as sequencing primer sites. The additional sequences are directed toward Illumina sequencing instruments or sequencing instruments that utilize those sequences; however a skilled artisan will understand that additional or alternative sequences used by other sequencing instruments or technologies are also equally applicable for use in the aforementioned methods.

In some embodiments, where a sample is barcoded directly via hybridization with capture probes or analyte capture agents hybridized, bound, or associated with either the cell surface, or introduced into the cell, as described above, sequencing can be performed on the intact sample.

A wide variety of different sequencing methods can be used to analyze barcoded analyte (e.g., the ligation product). In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based single plex methods, emulsion PCR), and/or isothermal amplification. Non-limiting examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods.

(1) Kits

In some embodiments, also provided herein are kits that include one or more reagents to detect one or more analytes described herein. In some instances, the kit includes a substrate comprising a plurality of capture probes comprising a spatial barcode and the capture domain. In some instances, the kit includes a plurality of probes (e.g., a first probe, a second probe, one or more spanning probes, and/or a third oligonucleotide).

A non-limiting example of a kit used to perform any of the methods described herein includes: (a) a substrate comprising a plurality of capture probes comprising a spatial barcode and a capture domain; (b) a system comprising: a plurality of first probes and second probes, wherein a first probe and a second probe each comprises sequences that are substantially complementary to an analyte, and wherein the second probe comprises a capture binding domain; and (c) instructions for performing the method of any one of the preceding claims.

Another non-limiting example of a kit used to perform any of the methods described herein includes: (a) an array comprising a plurality of capture probes; (b) a plurality of probes comprising a first probe and a second, wherein the first probe and the second probe are substantially complementary to adjacent sequences of an analyte, wherein the second probe comprises (i) a capture probe binding domain that is capable of binding to a capture domain of the capture probe and (ii) a linker sequence; (c) a plurality of enzymes comprising a ribonuclease and a ligase; and (d) instructions for performing the method of any one of the preceding claims.

Another non-limiting example of a kit used to perform any of the methods described herein includes: (a) an array comprising a plurality of capture probes; (b) a plurality of probes comprising a first probe and a second probe, wherein the first probe and the second probe are substantially complementary to adjacent sequences of an analyte, wherein the first probe includes a linker sequence, wherein the second probe comprises a capture probe binding domain that is capable of binding to a capture domain of the capture probe; (c) a plurality of enzymes comprising a ribonuclease and a ligase; and (d) instructions for performing the method of any one of the preceding claims.

In some embodiments of any of the kits described herein, the kit includes a second probe that includes a preadenylated phosphate group at its 5' end and a first probe comprising at least two ribonucleic acid bases at the 3' end.

EXAMPLES

Example 1. Spatial Gene Expression Analysis of FFPE-Fixed Samples Using RNA-Templated Ligation Others have demonstrated in situ ligation. See Credle et al., *Nucleic Acids Research*, Volume 45, Issue 14, 21 Aug. 2017, Page e128, https://doi.org/10.1093/nar/gkx471 (2017). However, the previous approaches have utilized hybridization using poly(A) tails which led to off-target binding. Here, the poly(A) tail on one probe oligonucleotide was switched to another sequence.

As an overview, a non-limiting example of RNA-templated ligation on an FFPE-fixed sample was performed as described in FIG. 13. FFPE-fixed samples were deparaffinized, stained (e.g., H&E stain), and imaged 1301. Samples were destained (e.g., using HCl) and decrosslinked 1302. Following decrosslinking, samples treated with pre-hybridization buffer (e.g., hybridization buffer without the first and second probes), probes were added to the sample, probes hybridized, and samples were washed 1303. Ligase was added to the samples to ligate hybridized probes to generate a ligation product and samples were then washed 1304. Probes were released from the analyte by contacting the biological sample with RNAse H 1305. Samples were then permeabilized to facilitate capture of the ligation product by the capture probes on the substrate 1306. Ligation products that hybridized to the capture probes were then extended 1307. The extended capture probes were denatured 1308. Denatured, extended capture probes were indexed and the amplified libraries were subjected to quality control 1309 before being sequenced.

FFPE sectioned mouse brain tissue slides were deparaffinized, permeabilized with PBST, and equilibrated with a pre-Hyb buffer twice for 5 minutes each. Decrosslinking the sample was performed using either a TE decrosslinking reagent or a PBS-tween decrosslinking reagent. For TE decrosslinking, 100 µl of TE buffer (pH 9.0) (Genemed 10-0046) was added per sample. Samples treated with TE were subjected to a thermal cycler protocol according to Table 1.

TABLE 1

Decrosslinking Thermal Cycler Protocol
Decrosslinking: Lid Temp: 70 C., Volume: 100 uL

| Step | Temp | Time |
| --- | --- | --- |
| Pre-heat | 70° C. | ∞ |
| Decrosslinking | 70° C. | 60 minutes |
| Hold | 22° C. | ∞ |

Following the thermal cycler protocol, slides were placed into a metal cassette and subject to the methods described in Table 2.

TABLE 2

Decrosslinking with HCl*

| Step | Timing |
| --- | --- |
| 1. Wash 1: Added 100 µl 0.1N HCl | 1 minute |
| 2. Wash 2: Removed the HCl and add 100 µl HCl | 1 minute |
| 3. Wash 3: Removed the HCl and add 100 µl HCl | 1 minute |
| 4. Buffer exchange: Removed HCl and add 100 µl TE buffer (pH 9.0) | |
| 5. Removed TE and add 100 µl TE (pH 9.0). | |
| 6. Incubated at 70° C. | 1 hour |
| 7. Removed TE and add 100 µl 1x PBS-Tween (0.05%) | |
| 8. Incubated at room temperature | 15 minutes |

*Note:
All liquid was removed at each step.

RTL probes were designed to hybridize to adjacent sequences of each analyte (e.g., mRNA sequence) of interest in the genome, including estrogen receptor, progesterone receptor, and ERBB2, also known as HER2. Here, 20,056 probe pairs (e.g., RHS and LHS probes) were added to each tissue sample to capture 19,490 different genes. Two RTL probes (a left-hand side (LHS) probe and a right-hand side (RHS) probe (see e.g., FIG. 6)) for each analyte were added simultaneously and hybridized at adjacent sequences of the target mRNA, forming RNA:DNA duplex structures. Following decrosslinking, the PBS-Tween was removed and the DNA probes (1 nM of each probe) were added to the tissue samples in a hybridization buffer for hybridizing the DNA probes to their respective mRNA targets. The hybridization buffer included SSC, formamide or an equivalent, yeast tRNA as carrier and the RHS and LHS DNA probes.

One probe oligonucleotide (e.g., the RHS probe or the 3' probe) comprises a non-target functional sequence at its 5' end while the other probe oligonucleotide (e.g., the LHS probe or the 5' probe) comprises a non-target polyA sequence at their 3' ends. The DNA probes were added to the tissue samples and incubated at 50° C. for 2 hours and 30 minutes according to thermal cycler protocol described in Table 3.

TABLE 3

Hybridization Protocol
Hybridization Thermal Cycler Protocol
Hyb: Lid Temp: 50 C., Volume: 100 uL

| Step | Temp | Time |
| --- | --- | --- |
| Pre-heat | 50° C. | ∞ |
| Hyb | 50° C. | 2 hours and 30 minutes |
| Hold for post hyb washes | 50° C. | ∞ |
| Hold | 22° C. | ∞ |

Following incubation at 50° C. for 2½ hours, the hybridization buffer was removed and the tissue was washed twice with each wash including 5 minutes at 50° C. with post-hybridization wash buffer pre-heated to 50° C. Post-hybridization wash buffer (Post-hyb buffer) included: SSC, yeast tRNA and nuclease free water.

To ligate two diribo probe oligonucleotides that adjacently hybridized on the target mRNA as described above, each sample was incubated with RNL2 T4 DNA ligase reaction mixture (ligation mix). The ligase reaction mixture included: T4 RNA Ligase Buffer (NEB B0293S), RNL2 ligase and nuclease free water.

To ligate two DNA probe oligonucleotides that adjacently hybridized on the target mRNAs as described above, SplintR (NEB) in a ligation buffer was added to each sample. The ligase reaction mixture included: Tris-HCl (pH 7.5) MnCl$_2$ ATP, DTT, surrogate fluid, SplintR ligase (NEB), and nuclease free water per sample. The ligation and wash steps were performed as described in Table 4.

Following DNA probe ligation the tissue samples were washed twice for 5 minutes at 60° C. in a SSC/formamide post ligation wash buffer.

TABLE 4

Ligation Protocol
Probe Lisation

| Step | Time |
|---|---|
| Removed ALL Post-Hyb Buffer before adding Ligase Mix | 1 h |
| Added Ligase Mix and Incubated at 37° C. | |
| Removed post-ligation wash buffer and added 2X SSC**. | |
| Repeated 2X SSC wash. | |
| The cassette was cooled down to room temperature before adding RNAse | |
| Wash 1: Removed Ligase Mix, added post-ligation wash buffer*, and incubated at 60° C. for 5 minutes | 5 min |
| Remaining wash buffer at heated to 60° C. | |
| Wash 2: Removed post-ligation wash buffer, added pre-heated post-ligation buffer and incubated at 60° C. for 5 minutes. | 5 min |

*Post ligation wash buffer included (per sample): SSC, formamide or an equivalent, and nuclease free water.

RNase H was added to digest the RNA strand of the hybridized RNA:DNA duplex. Briefly, the RNA of the DNA:RNA hybrids was digested by incubating the samples with RNase H mix for 30 minutes at 37° C., where the RNAse H mix included: RNAse H buffer and RNaseH. Following the incubation and while the same remained at 37° C., the biological sample was permeabilized to release the ligated RTL probes using 1.25 mg/mL Proteinase K. In particular, the Proteinase K solution included (per sample): Tris (pH 7.5), MgCl2, Sarkosyl, or SDS, Proteinase K (Enzyme), and nuclease free water. The sample was incubated at 37° C. for at least 5 minutes in the Proteinase K solution. The samples were then washed three times with 2×SSC.

The released, ligated DNA probes that served as a proxy for the target mRNA were allowed to hybridize to the capture domain on the capture probe immobilized on the spatial array via the polyA tail on the 3' end of the RHS probe. The captured ligated probes were copied, using the capture probe as a template and the extension product was released from the spatial array. Briefly, the tissues were incubated with a second strand extension mix comprising Kapa Hifi DNA polymerase for 25 minutes at 53° C. Following incubation, the second strand extension mix was removed from the tissues and the tissues were washed with 2×SSC. A solution of KOH was added to each of the tissue wells, the tissues were incubated at room temperature for 10 minutes to release the extension product from the spatial array and the supernatant from each tissue well was transferred for quantification, and library preparation. Sample quantification was performed using qPCR and KAPA SYBR FAST qPCR master mix according to the manufacturer's instructions. Briefly, KAPA SYBR master mix was prepared by adding qPCR primer cDNA_F and qPCR primer sRNA_R2. The thermal cycler protocol included: 3 minutes at 98° C.; 30 cycles with 5 seconds at 98° C., and 30 seconds at 63° C. For library preparation, samples were indexed using an Amp Mix that included dual indexing primers and an Amp Mix. Nucleic acids were then sequenced and analyzed.

As controls, concurrent experiments were run in which no ligase was added, pepsin was added before RNAse H treatment, or pepsin was added after RNAse H treatment.

Figure 14:
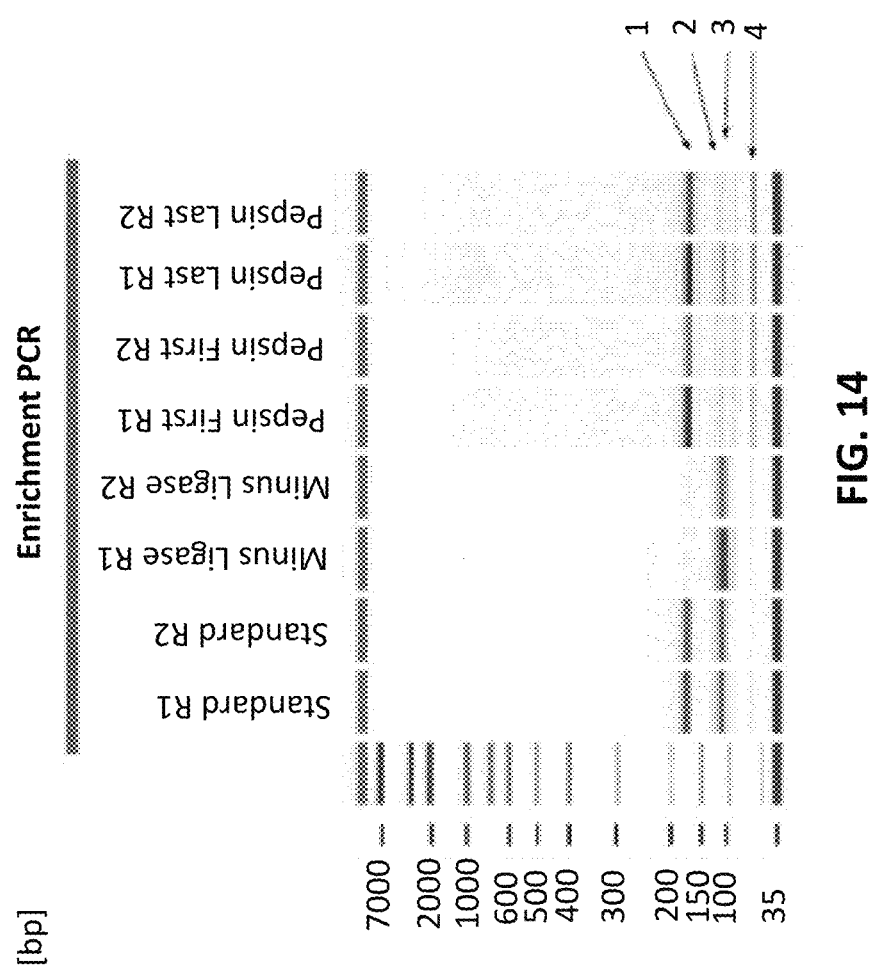
FIG. 14 show enrichment PCR results for detection of various probes. R1=run 1; R2=run 2. (1) represents band for ligation product with capture probe. (2), (3) and (4) represent non-ligation products.
Figure 15:
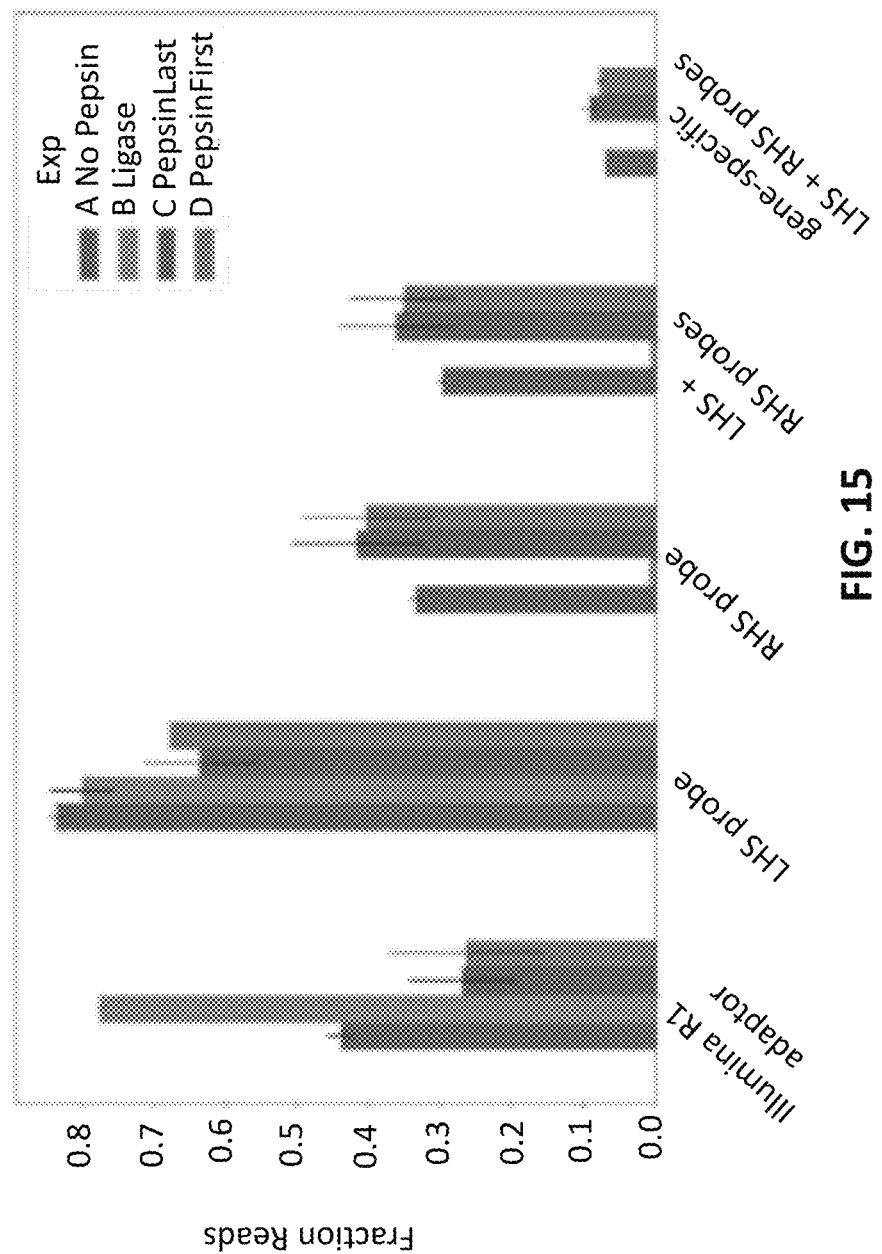
FIG. 15 shows fraction of reads for various combination of conditions and probes.
Figure 16A:
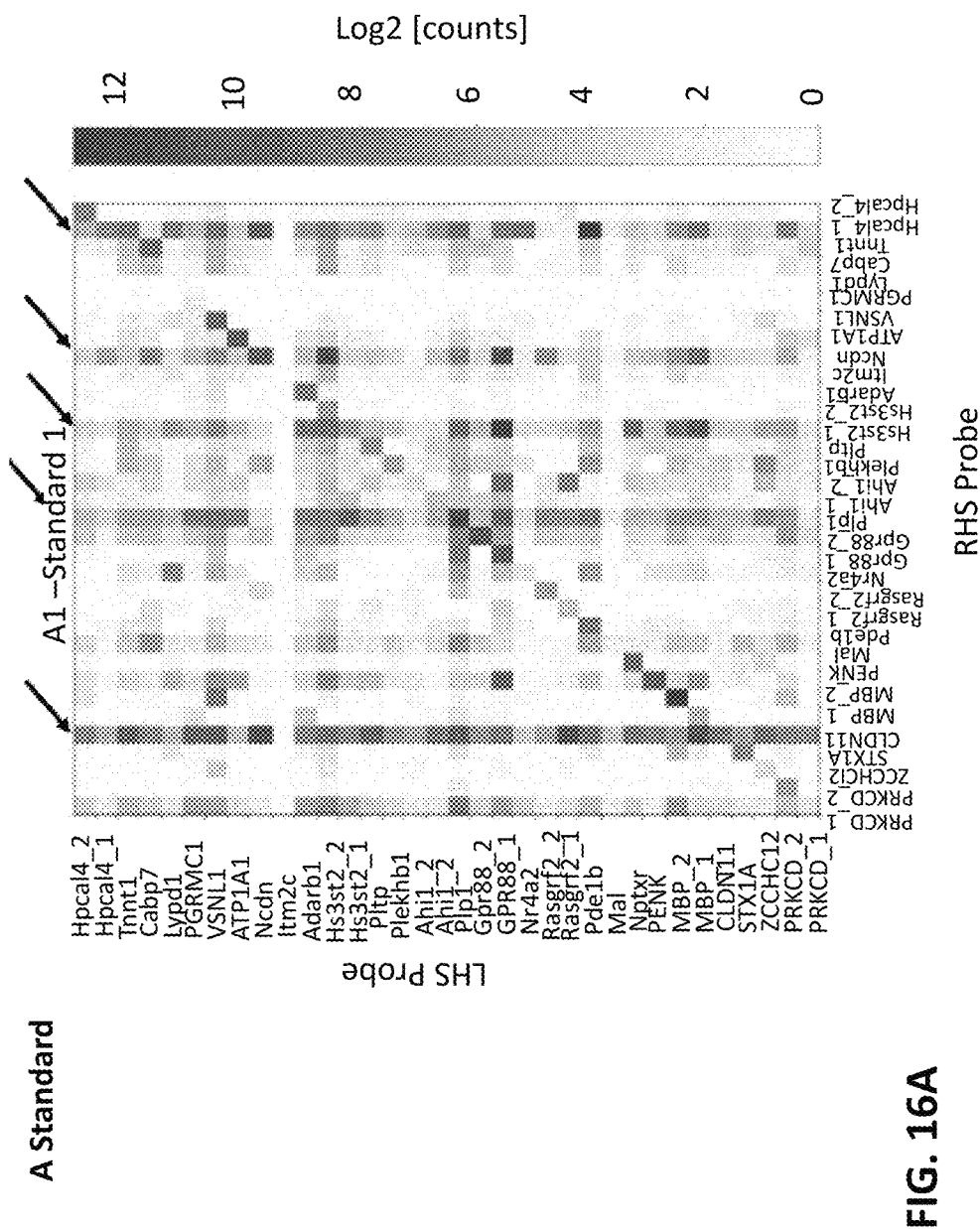
FIGS. 16A-16B show matrices of specific probe combinations.
Figure 16B:
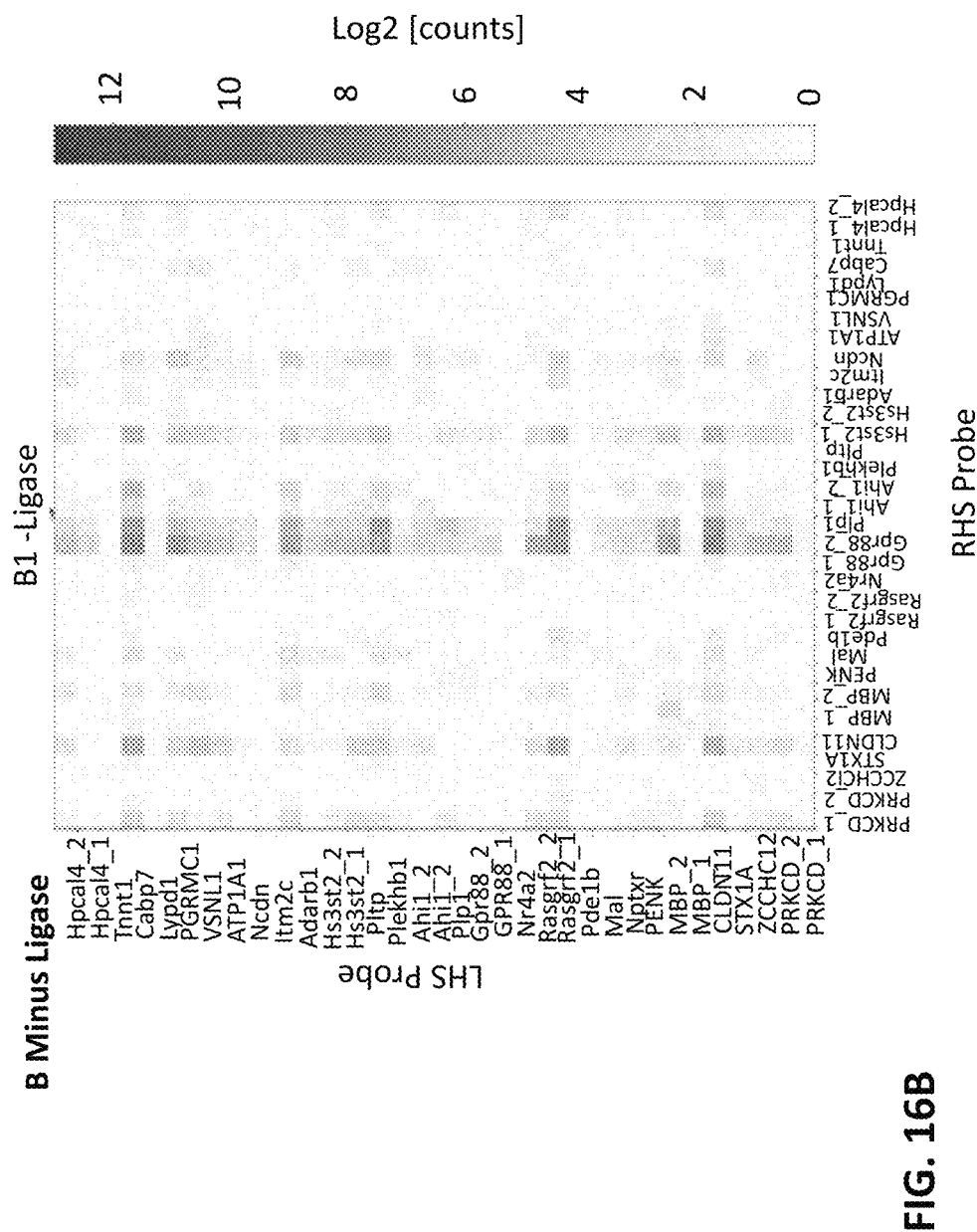
Figure 17C:
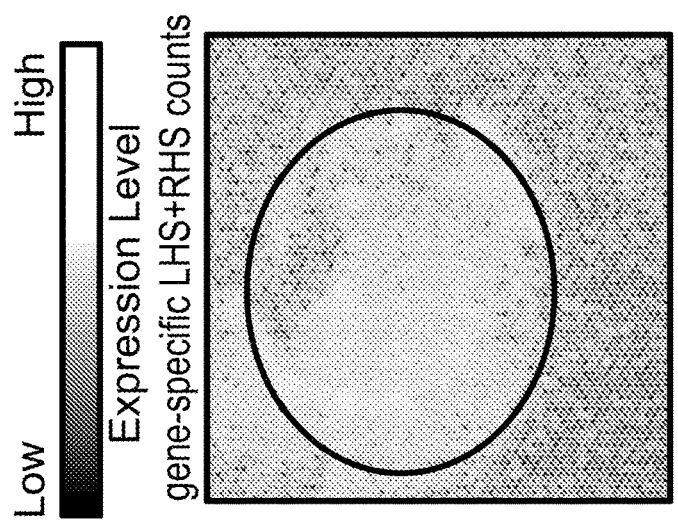
FIGS. 17A-17C show gene expression patterns in mouse brain tissue using total probe oligonucleotide counts (FIG. 17A), nonspecific probe oligonucleotide counts (FIG. 17B), and gene-specific probe oligonucleotide counts (FIG. 17C).
Figure 17B:
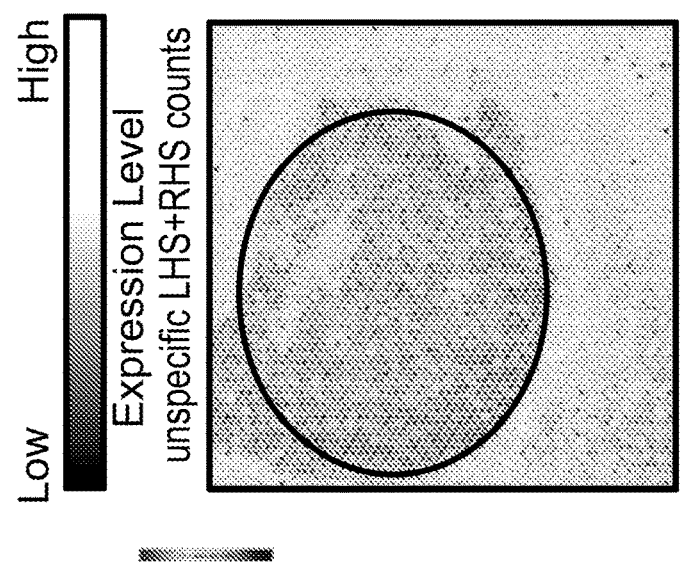
Figure 17A:
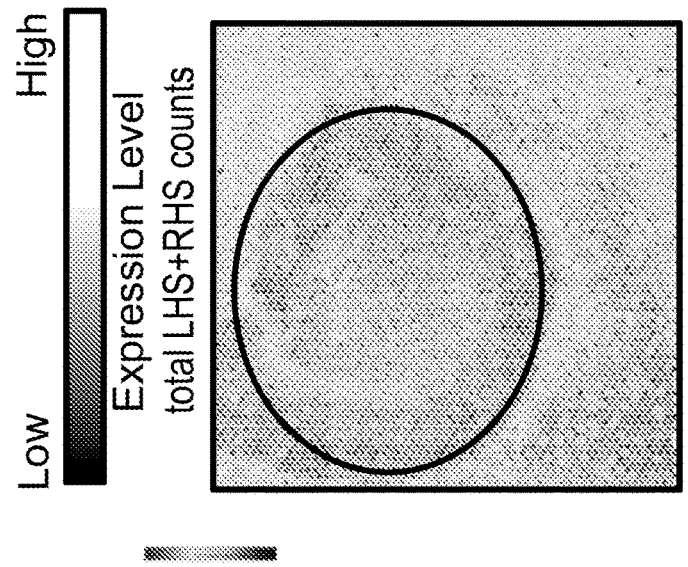
Figure 18A:
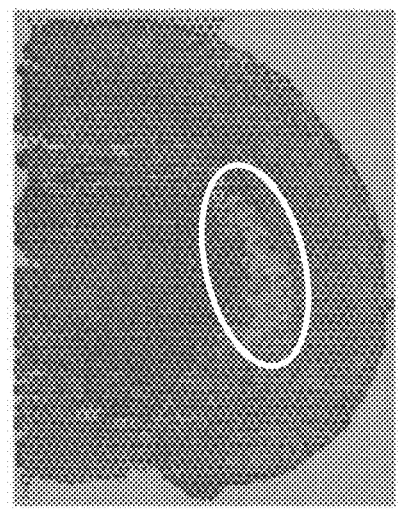
FIGS. 18A-18E show target genes with spatial expression in mouse brain tissue.
Figure 18B:
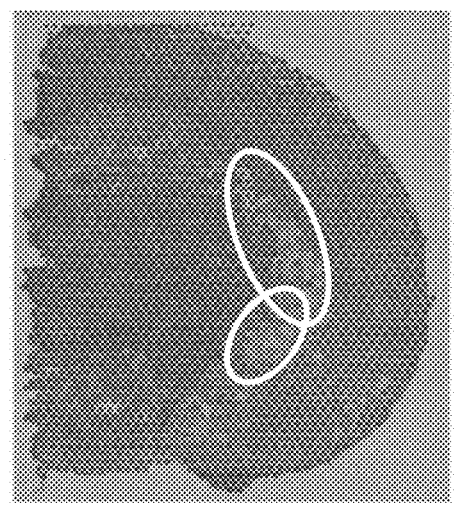
Figure 18C:
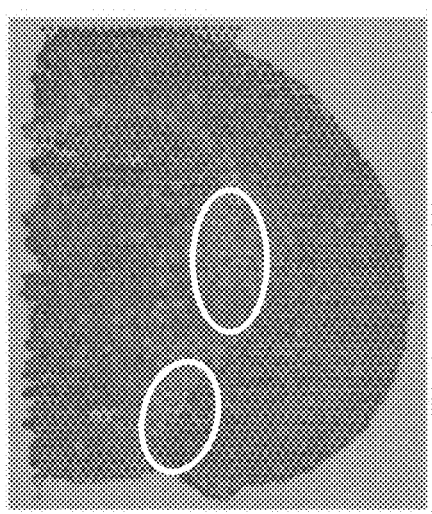
Figure 18D:
Figure 18E:
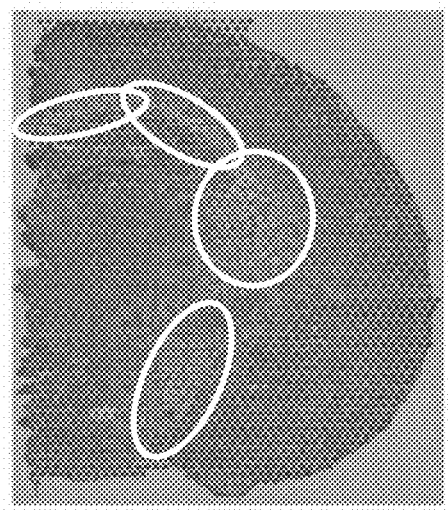
Figure 19A:
Figure 19B:
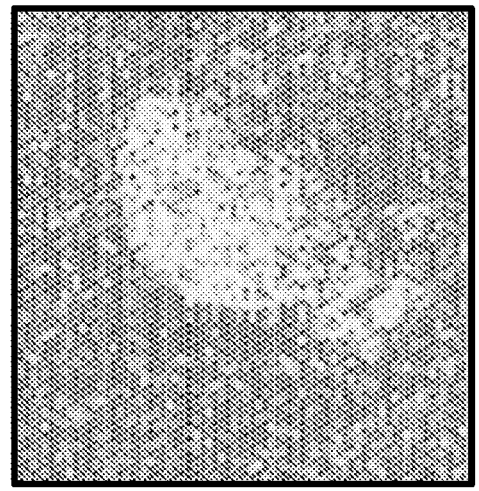
Figure 19C:
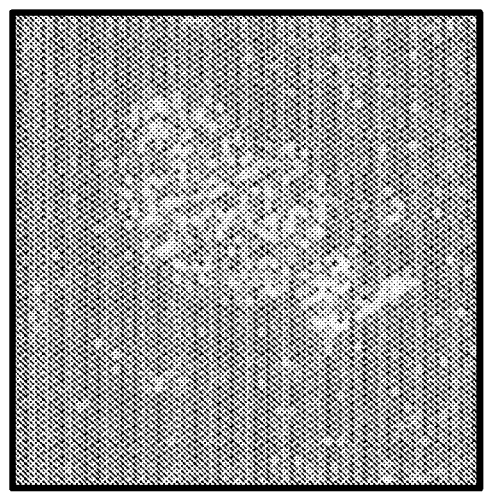
Figure 19D:
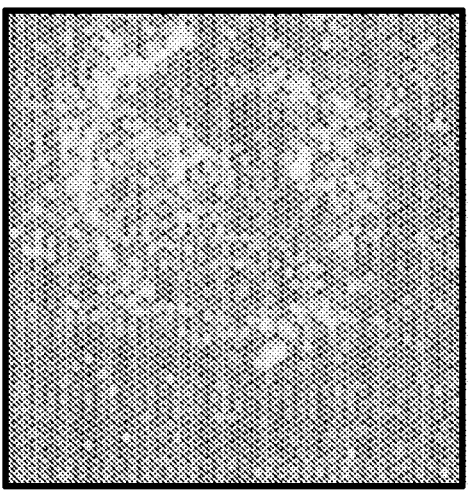

As shown in FIGS. 14-19, spatial expression of ligated probe pairs highlights underlying mouse brain tissue physiology. FIG. 14 shows PCR results demonstrating that a ligation product was captured and amplifiable whether the permeabilization occurred before or after RNase H treatment (positive control=standard, negative control=minus ligase). Arrow 1 points to a PCR band that represents desired ligation products, whereas arrows 2, 3 and 4 represent non-ligation products. FIG. 15 shows non-specific probe detected as a fraction of total reads for each condition. FIGS. 16A-B shows most probe combinations are specific. The arrows indicate RHS probes that had increased background and therefore include some non-specific hybridization. Looking at total counts in FIG. 17, gene-specific LHS+RHS probes overlay with the tissue footprint (see FIGS. 17A-C with black circle indicating tissue footprint).

Further, probes specific for various genes (e.g., Grp88, Penk, Plp1, Nptrx, and Mpb2) were added to the sample in Hybridization buffer first for 30 minutes at 60° C., and then for 2 hours at 45° C. (See, e.g., FIG. 18 and FIG. 19). When target-specific UMIs were counted, a more detailed expression pattern was observed. See, e.g., FIGS. 19B-19F. This analysis revealed that longer hybridization led to higher sensitivity. Referring to FIGS. 18A-18E, white circles indicate spots reporting expression for the indicated gene.

Figure 20A:
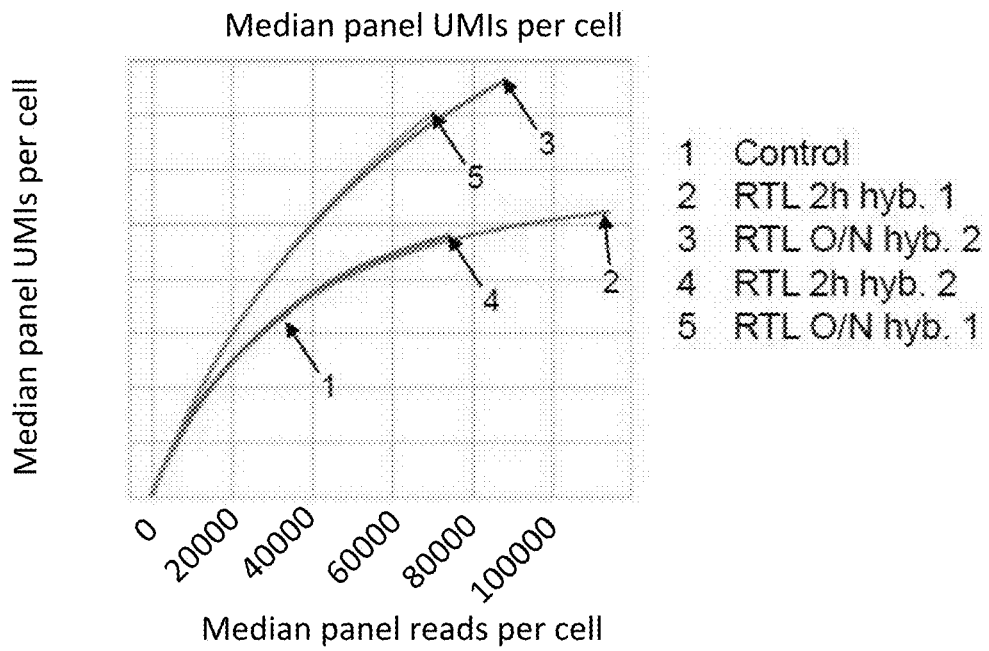
FIG. 20A shows median unique molecular identifiers (UMIs) per cell versus mean reads per cell for different hybridization conditions.
Figure 20B:
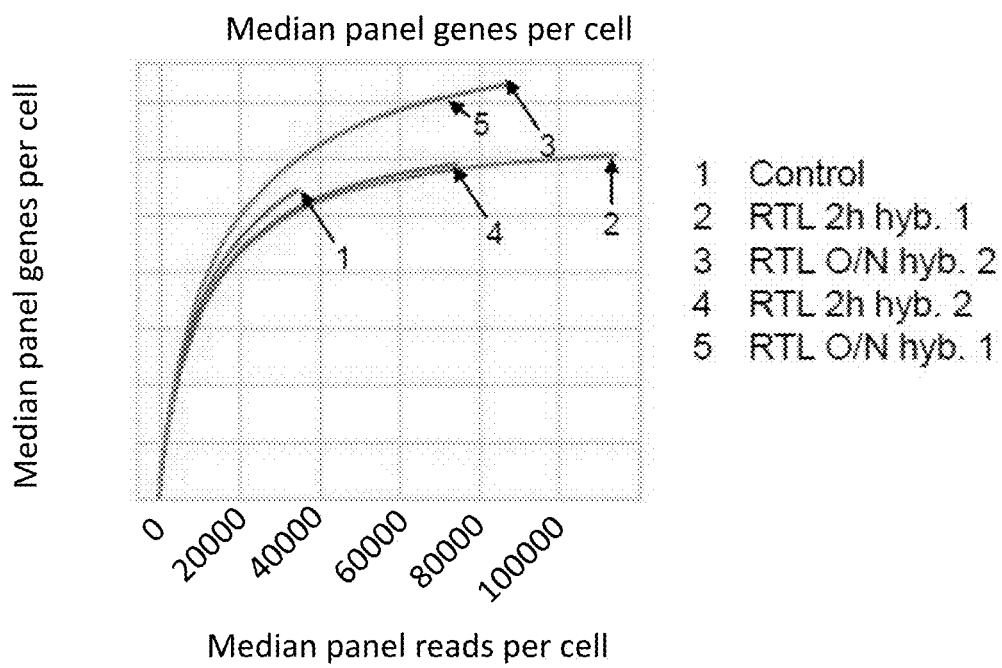
FIG. 20B shows median genes per cell versus mean reads per cell for different hybridization conditions.

An overnight hybridization was performed comparative to a 2 hour hybridization as discussed. Analysis on mouse brain samples using 21,833 probe pairs (e.g., RHS and LHS probes) added to each tissue sample to capture 21,604 different genes revealed that overnight hybridization, thus longer hybridization, led to higher sensitivity compared to a positive control (see FIGS. 20A-20B). The mouse probes were designed from targets derived from Appris (see Rodriguez et al., Nucleic Acids Research, 46: D213-217, doi: 10.1093/nar/gkx997 (2018), which is herein incorporated by reference in its entirety) and GENCODE. All probe pairs were non-overlapping and include generally about 1 probe pair per gene.

Example 2. Spatial Gene Expression Analysis of Triple Positive Breast Cancer (TPBC) Using RNA Templated Ligation (RTL)

This example demonstrates that RTL can be performed on a sample in order to identify analyte abundance and spatial location in an unbiased manner.

Figure 21A:
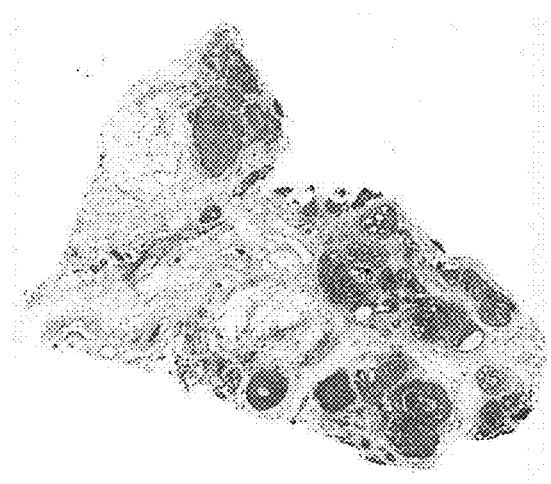
FIG. 21A shows hematoxylin staining for a section of a triple positive breast cancer tissue sample.

A two-year old triple positive ("TPBC," HER2, estrogen receptor, and progesterone receptor-positive) breast cancer sample preserved by FFPE processing was examined for analyte abundance and spatial location. The TPBC samples were queried with DNA probes via RNA-templated ligation methods. Before the ligation step, the TPBC tissue samples were deparaffinized and stained per established protocols. For example, FFPE TPBC tissue samples were prewarmed in a water bath (40° C.), sectioned (10 μm), dried at 42° C. for several hours and placed in a desiccator at room temperature overnight. The dry, sectioned tissues were deparaffinized by baking at 60° C., moved through a series of xylene and EtOH washes, rinsed in water several times. Following rinsing, the deparaffinized tissues were stained with hematoxylin per established protocols. The stained tissues were imaged, identifying regions of tumor and stroma. See FIG. 21A.

The tissues were decrosslinked to remove formaldehyde crosslinks within the sample thereby releasing the analytes for RNA templated ligation. Briefly, the tissue samples were incubated with an HCl solution for 1 minute, repeated twice for a total of 3 minutes. Following HCl incubations, the tissue sections were incubated at 70° C. for 1 hour in TE pH 9.0. TE was removed and the tissues were incubation in 1×PBS-Tween for 15 minutes.

RTL probes were designed to hybridize to adjacent sequences of each analyte (e.g., mRNA sequence) of interest in the genome, including estrogen receptor, progesterone receptor, and ERBB2, also known as HER2.

Probes were designed from targets derived from Appris (see, Rodriguez et al., *Nucleic Acids Research*, 46: D213-217, doi: 10.1093/nar/gkx997 (2018), which is herein incorporated by reference in its entirety) and GENCODE. All probe pairs were non-overlapping and include generally about 1 probe pair per gene.

Here, 20,056 probe pairs (e.g., RHS and LHS probes) were added to each tissue sample to capture 19,490 different genes, including ESR1, PGR and HER2, in the human genome. Two RTL probes (a left-hand side (LHS) probe and a right-hand side (RHS) probe (see, e.g., FIG. 6)) for each analyte were added simultaneously and hybridized at adjacent sequences of the target mRNA, forming RNA:DNA duplex structures.

Following decrosslinking, the DNA probes (1 nm of each probe) were added to the tissue samples in a hybridization buffer for hybridizing the DNA probes to their respective mRNA targets. One probe oligonucleotide (e.g., the RHS probe or the 3' probe) comprises a non-target functional sequence at its 5' end while the other probe oligonucleotide (e.g., the LHS probe or the 5' probe) comprise a non-target polyA sequence at their 3' ends. Briefly, hybridization buffer with the DNA probes was added to the tissue samples and the tissues were incubated at 50° C. of approximately 2½ hrs. The hybridization/DNA probe buffer was removed and the tissues washed by addition of a post hybridization buffer without DNA probes and incubation at 50° C. for 5 minutes, for a total of 3 post hybridization washes.

To ligate the two DNA probe oligonucleotides that adjacently hybridized on the target mRNAs as described above, SplintR (NEB) in a ligation buffer was added to each tissue sample and the tissues were incubated at 37° C. for 60 minutes. Following DNA probe ligation the tissue samples were washed twice for 5 minutes at 60° C. in a SSC/formamide post ligation wash buffer.

Next, RNase H was added to digest the RNA strand of the hybridized RNA:DNA duplex. Briefly, the RNA of the DNA:RNA hybrids was digested by incubating the tissues with RNase H for 30 minutes at 37° C. The biological sample then was permeabilized to release the ligated RTL probes and contacted with a plurality of capture probes attached to a slide. In particular, after 30 minutes, the tissues were washed and permeabilized by adding 1.25 mg/ml Proteinase K, incubated at 37° C. for at least 5 minutes and then washed to remove the protease.

The released, ligated DNA probes that served as a proxy for the target mRNA were allowed to hybridize to the capture domain on the capture probe (capture probes immobilized on the spatial array) via the polyA tail on the 3' end of the RHS probe. The captured ligated probes were copied, using the capture probe as a template and the extension product was released from the spatial array. Briefly, the tissues were incubated with a second strand extension mix comprising Kapa Hifi DNA polymerase (Roche) for 25 minutes at 53° C. Following incubation, the extension mix was removed from the tissues and the tissues were washed with SSC. A solution of KOH was added to each of the tissue wells, the tissues were incubated at room temperature for 10 minutes to release the extension product from the spatial array and the supernatant from each tissue well was transferred for quantitation, library preparation and sequencing on the Illumina NextSeq sequencing instrument.

Figure 21B:
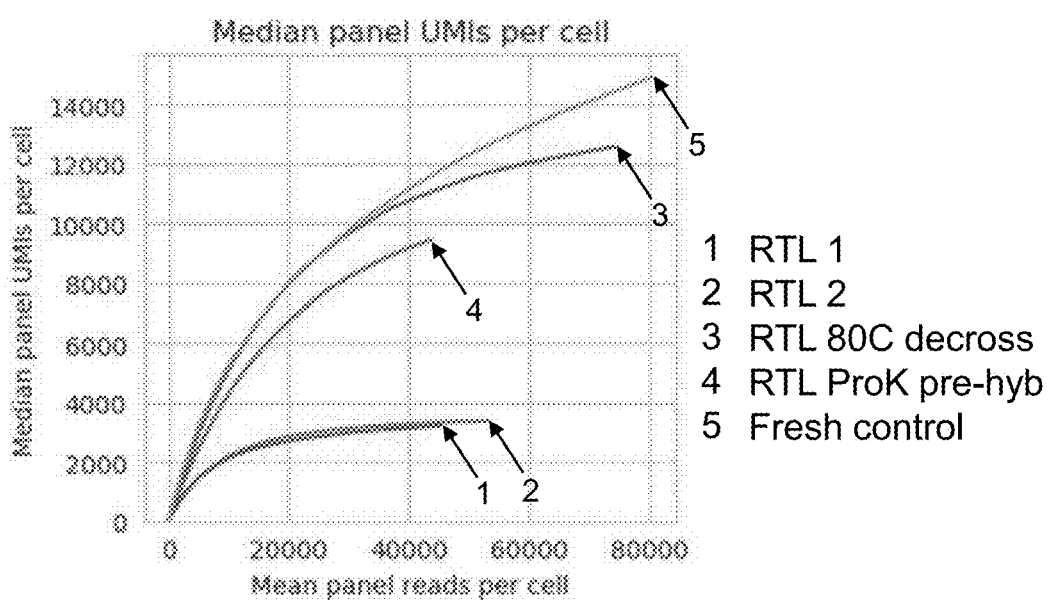
FIG. 21B shows median UMI per cell count versus mean read per cell for the different conditions.
Figure 21C:
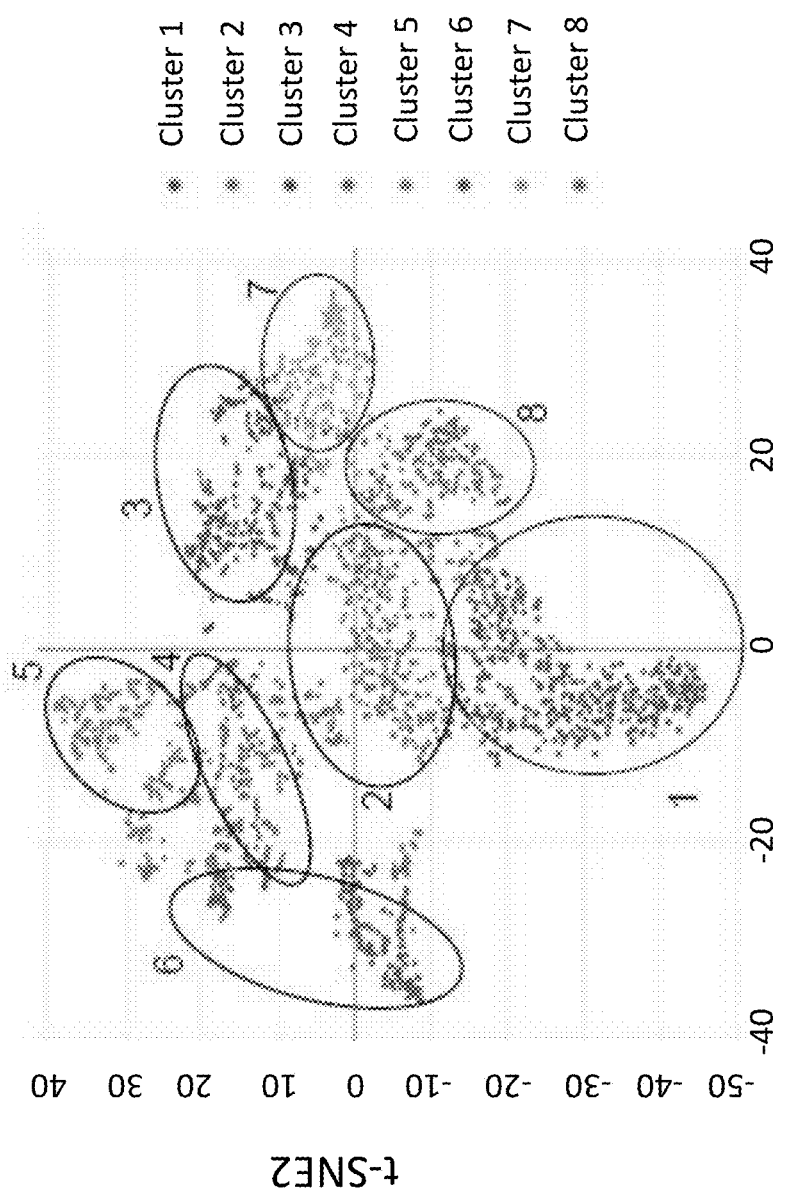
FIG. 21C shows t-SNE projection of spots in eight different clusters.
Figure 21D:
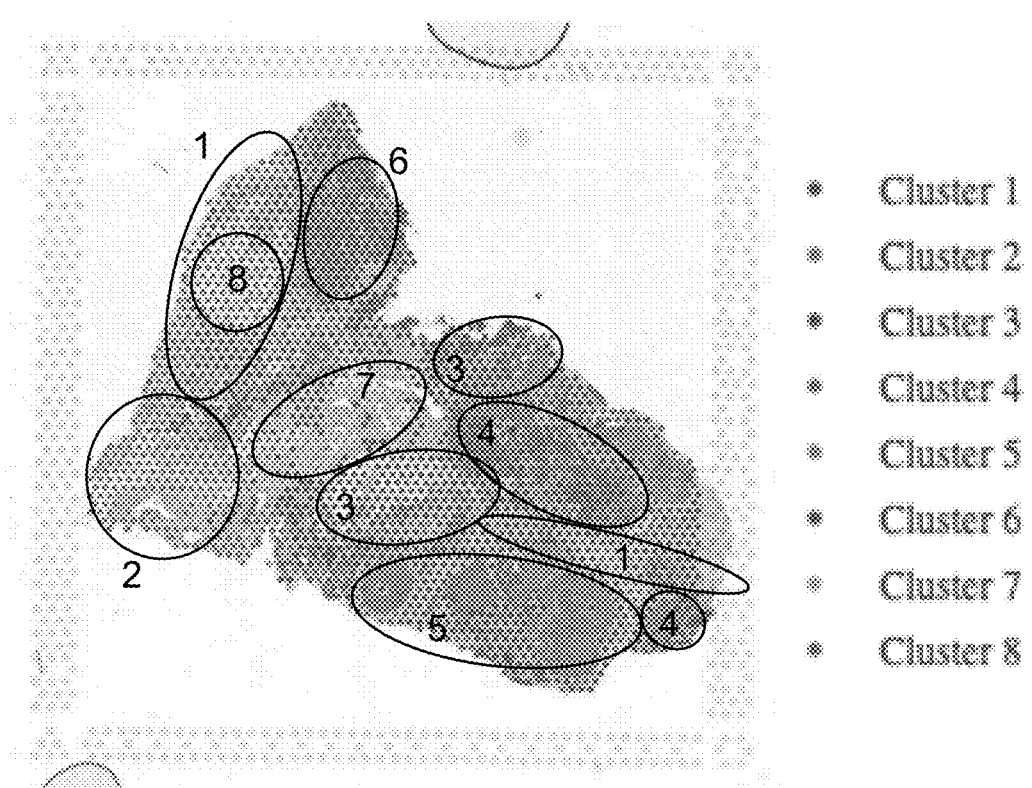
FIG. 21D shows the same tissue from FIG. 21A with various clusters (n=8 clusters) expressed in distinct areas of the tissue.
Figure 21E:
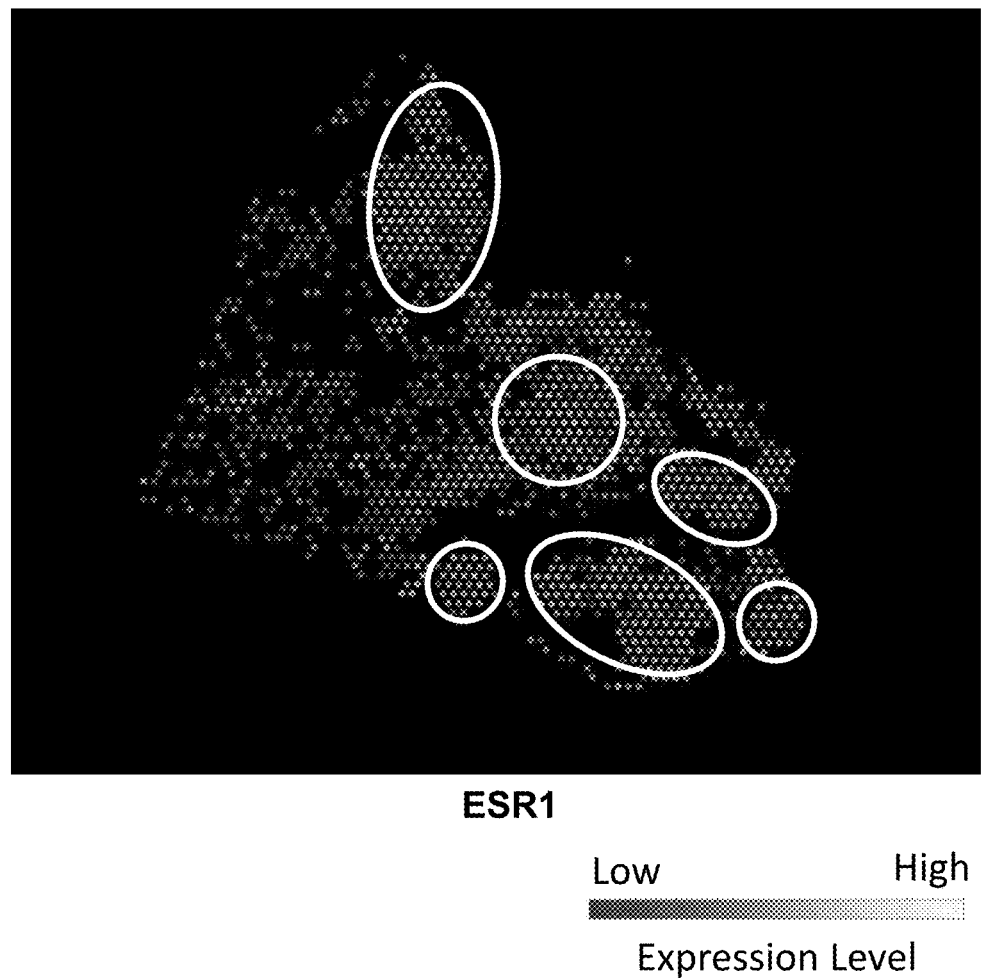
FIG. 21E shows expression of estrogen receptor (ESR1).
Figure 21F:
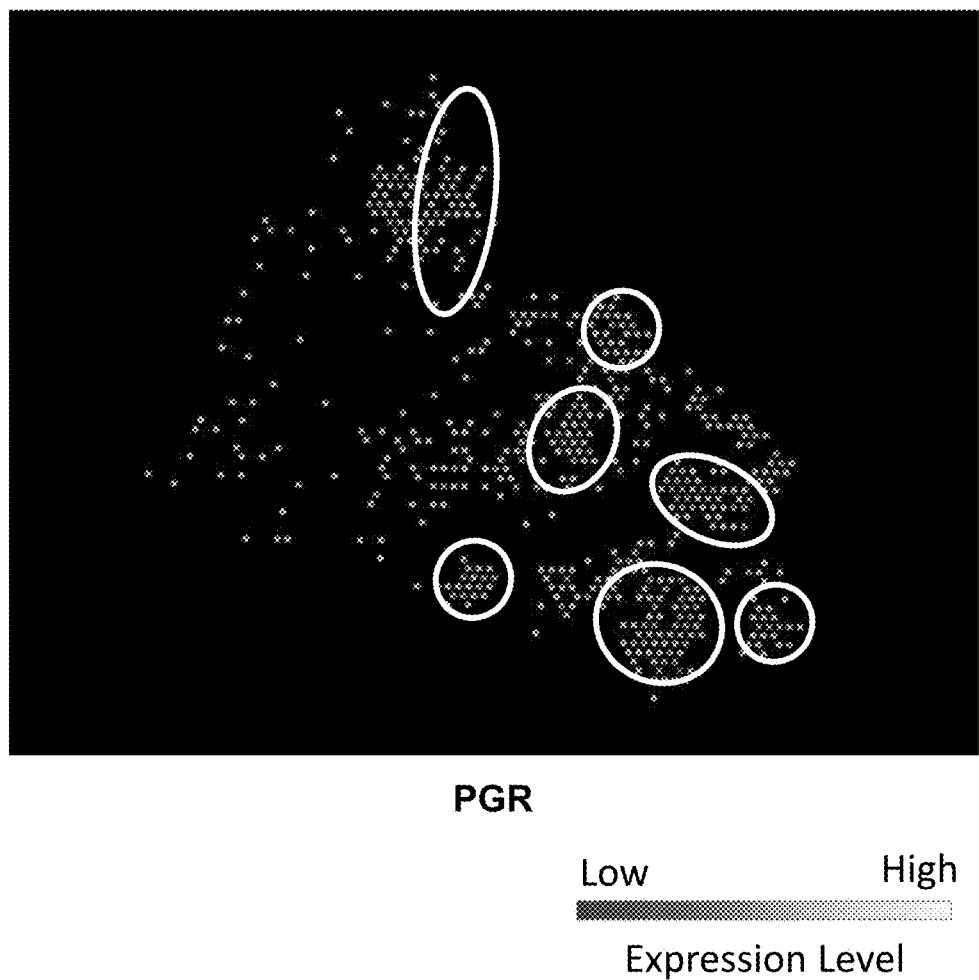
FIG. 21F shows expression of estrogen receptor progesterone receptor (PGR).
Figure 21G:
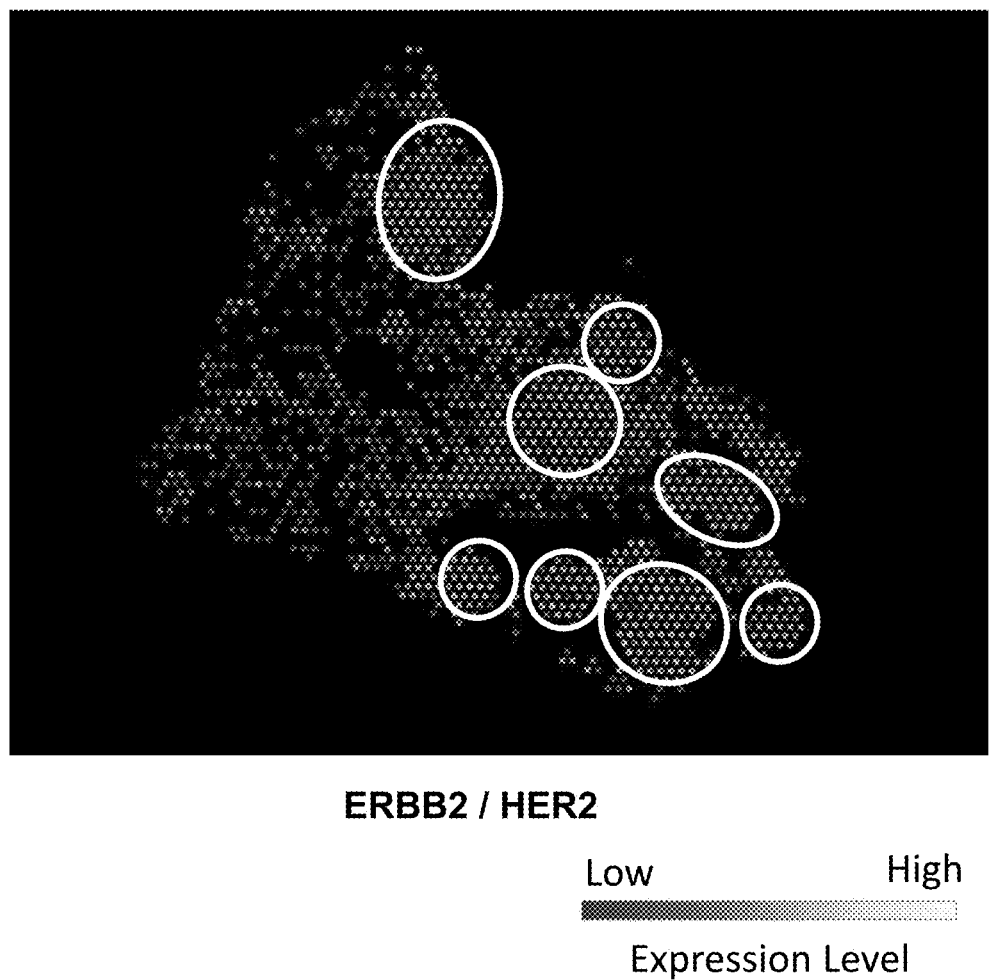
FIG. 21G shows expression of ERBB2, also known as HER2.
Figure 22A:
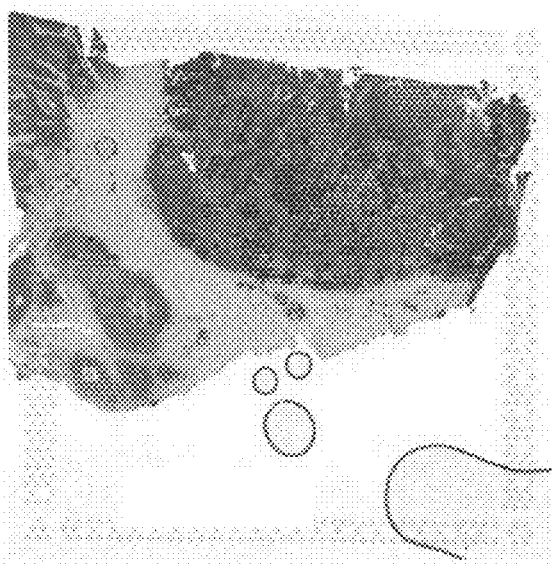
FIG. 22A shows a hematoxylin stain for a section of Ovarian Cancer sample.
Figure 22B:
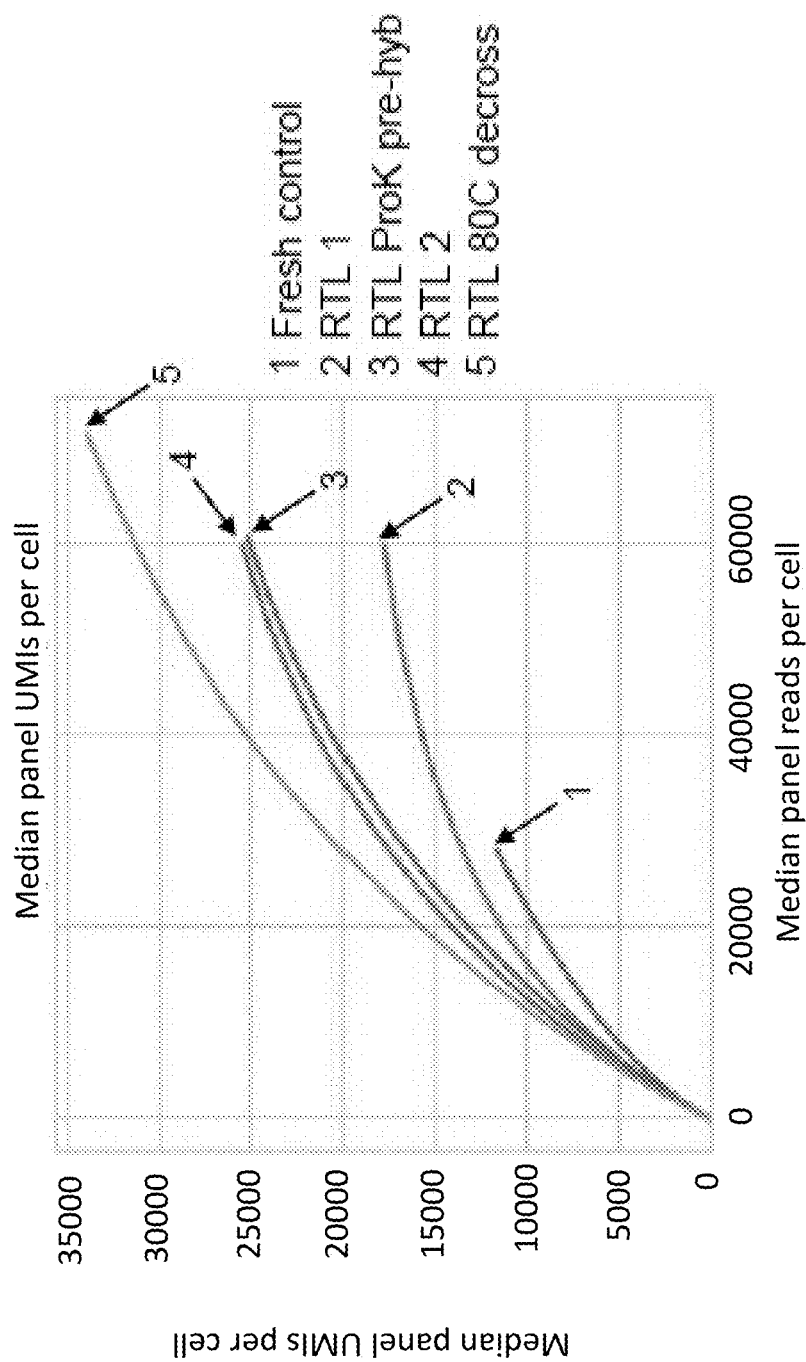
FIG. 22B shows median UMI per cell versus mean read per cell for the different conditions.
Figure 22C:
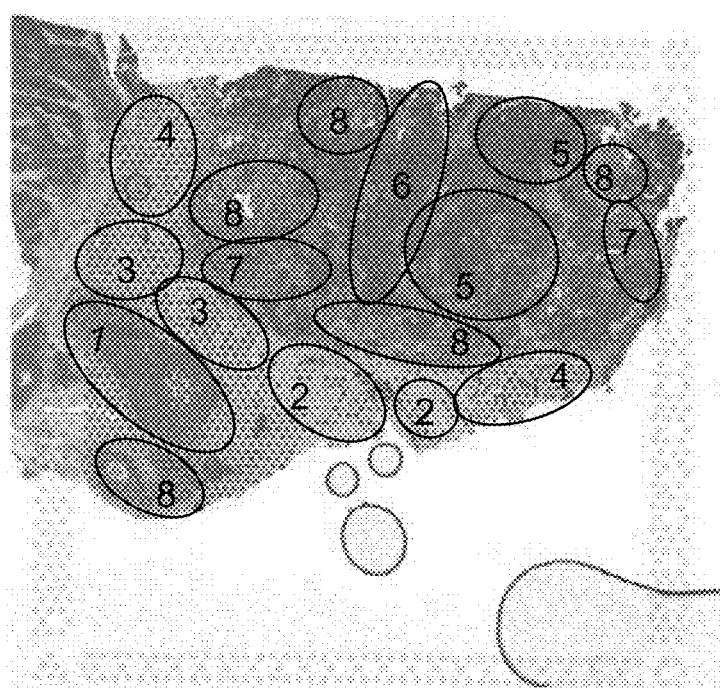
FIG. 22C shows the same tissue from FIG. 25A with various clusters (n=8 clusters) expressed in distinct areas of the tissue.
Figure 22D:
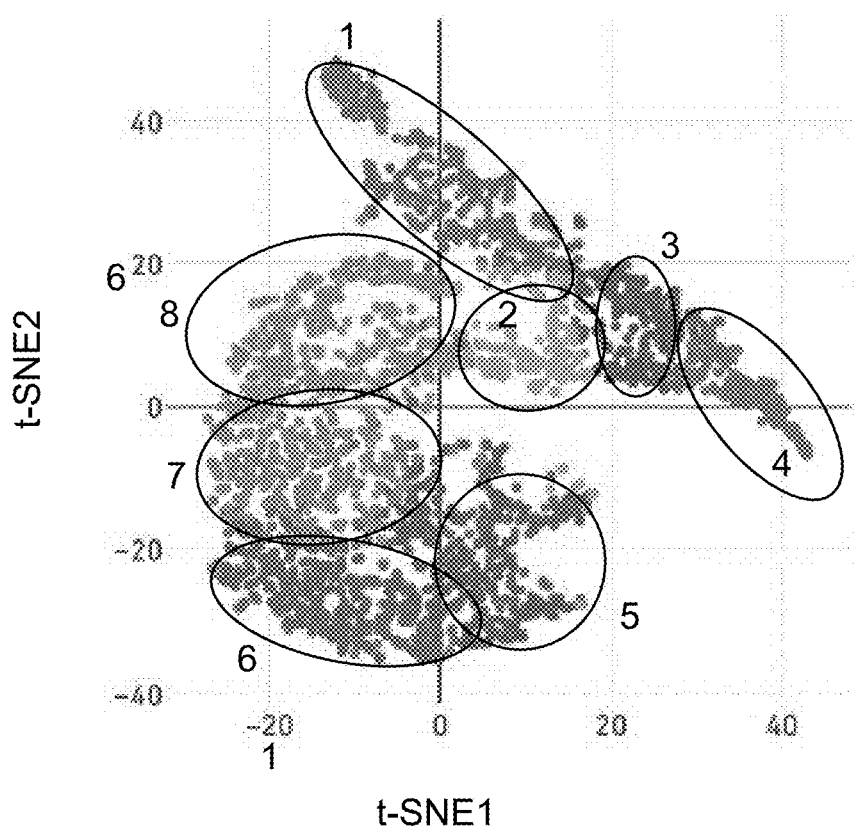
FIG. 22D shows t-SNE projection of spots in eight different clusters.
Figure 23:
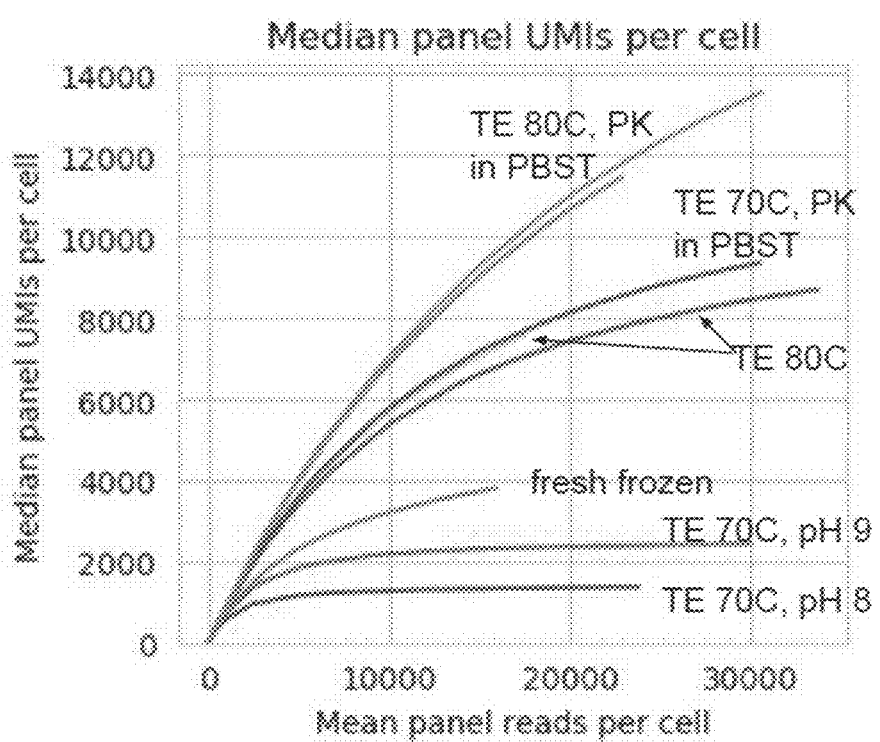
FIG. 23 shows median UMIs per cell versus reads per cell for different decrosslinking conditions.
Figure 24:
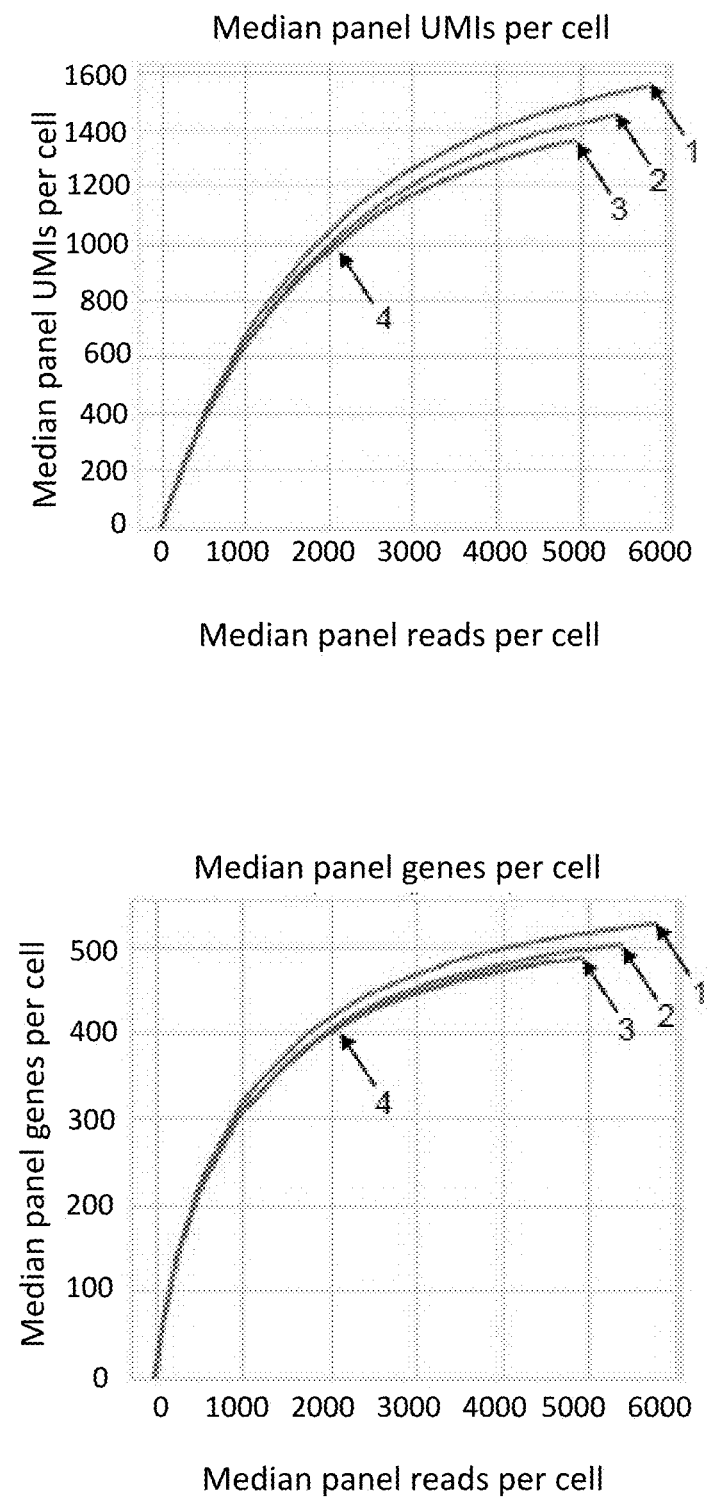
FIG. 24 shows median UMIs per cell versus reads per cell (top panel) and median genes per cell versus reads per cell (bottom panel) for different treatment conditions (RNase).
Figure 25:
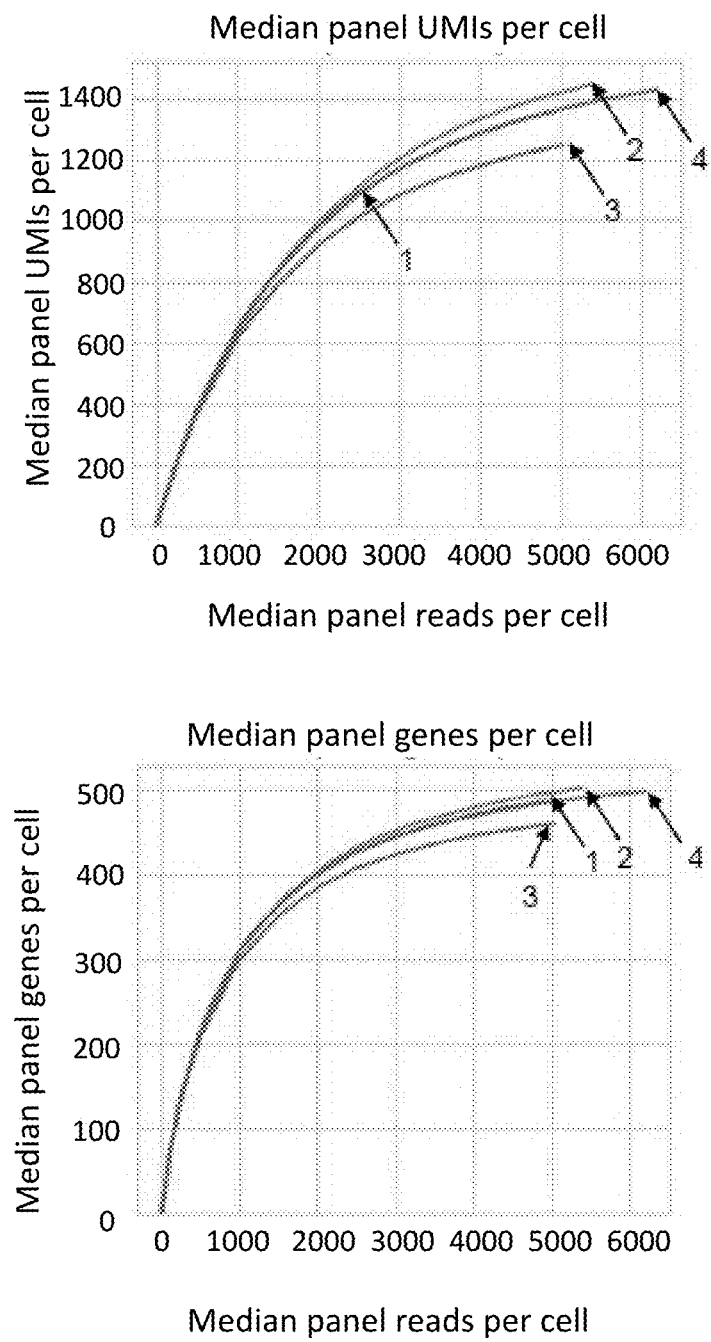
FIG. 25 shows median UMIs per cell versus reads per cell (top panel) and median genes per cell versus reads per cell (bottom panel) for different treatment conditions (time and temperature).

Assessing the whole transcriptome helped to better understand TPBC heterogeneity. For example, it was observed that using 20,056 probe pairs (e.g., RHS and LHS probes) to capture 19,490 different genes revealed comparable results to a positive control in terms of number of UMIs per cell versus number of genes per cell (FIG. 21B). Analysis of spatial location and abundance of each RTL ligated probe that hybridized to the array revealed eight (8) different clusters of expression, demonstrating that differential gene expression and location of the expressed genes can be determined using RTL probes. See FIGS. 21C-21D. Referring to FIG. 21C, each point on the plot is a spot on the array. Each spot is assigned to a cluster, which are indicated by black circles. In some cases, spots assigned to a cluster are outside the indicated circle on the plot. Referring to FIG. 21D, each spot on the array is assigned to a cluster and each cluster is indicated, in part, by circles. In some cases, spots are assigned to a cluster but are not within the indicated circles on the array. Finally, individual analyte expression was determined. A TPBC sample routinely exhibited elevated levels of estrogen receptor, progesterone receptor, and ERRB2 (HER2). As shown in FIGS. 21E-21GA.

Embodiment A1. A method for determining a location of an analyte in a biological sample comprising:

(a) contacting the biological sample with an array comprising a plurality of capture probes, wherein a capture probe of the plurality comprises: (i) a spatial barcode and (ii) a capture domain;

(b) contacting the biological sample with a first probe oligonucleotide and a second probe oligonucleotide, wherein the first probe oligonucleotide and the second probe oligonucleotide each comprise a sequence that is substantially complementary to adjacent sequences of the analyte, and wherein the second probe oligonucleotide comprises a capture probe capture domain;

(c) hybridizing the first probe oligonucleotide and the second probe oligonucleotide to the analyte in a formamide-free hybridization buffer;

(d) ligating the first probe oligonucleotide and the second probe oligonucleotide, thereby generating a ligation product;

(e) releasing the ligated product from the analyte and hybridizing the ligation product to the capture domain; and (f) determining (i) all or a part of the sequence of the ligation product specifically bound to the capture domain, or a complement thereof, and (ii) all or a part of the sequence of the spatial barcode, or a complement thereof, and using the determined sequence of (i) and (ii) to identify the location of the analyte in the biological sample.

Embodiment A2. The method of Embodiment A1, wherein the capture probe further comprises one or more functional domains, a unique molecular identifier, a cleavage domain, and combinations thereof.

Embodiment A3. The method of Embodiment A1 or A2, wherein the array comprises one or more features on a substrate.

Embodiment A4. The method of Embodiment A3, wherein the one or more features comprises a bead.

Embodiment A5. The method of Embodiment A3, wherein the substrate comprises a slide.

Embodiment A6. The method of any one of Embodiments A1-A5, wherein the formamide-free hybridization buffer is a saline-sodium citrate (SSC) hybridization buffer.

Embodiment A7. The method of Embodiment A6, wherein SSC is present in the SSC hybridization buffer from about 1×SSC to about 6×SSC.

Embodiment A8. The method of Embodiments A6 or A7, wherein SSC is present in the SSC hybridization buffer from about 2×SSC to about 4×SSC.

Embodiment A9. The method of any one of Embodiments A6-A8, wherein the SSC hybridization buffer comprises a solvent.

Embodiment A10. The method of Embodiment A9, wherein the solvent comprises ethylene carbonate.

Embodiment A11. The method of any one of Embodiments A6-A10, wherein ethylene carbonate is present in the SSC hybridization buffer from about 10% (w/v) to about 25% (w/v).

Embodiment A12. The method of any one of Embodiments A6-A11, wherein ethylene carbonate is present in the SSC hybridization buffer from about 15% (w/v) to about 20% (w/v).

Embodiment A13. The method of any one of Embodiments A6-A12, wherein ethylene carbonate is present in the SSC hybridization buffer at about 13% (w/v).

Embodiment A14. The method of any one of Embodiments A6-A13, wherein the SSC hybridization buffer is at a temperature from about 40° C. to about 60° C.

Embodiment A15. The method of any one of Embodiments A6-A14, wherein the SSC hybridization buffer is at temperature from about 45° C. to about 55° C. Embodiment A16. The method of any one Embodiments A6-A15, where in the SSC hybridization buffer is at a temperature of about 50° C.

Embodiment A17. The method of any one of Embodiments A6-A16, wherein the SSC hybridization buffer further comprises one or more of a yeast tRNA, a crowder, or an additive.

Embodiment A18. The method of any one of Embodiments A1-A17, wherein ligating in step (d) comprises a ligase.

Embodiment A19. The method of Embodiment A18, wherein the ligase is one or more of a T4 RNA ligase (Rnl2), a SplintR ligase, a single stranded DNA ligase, or a T4 DNA ligase.

Embodiment A20. The method of Embodiment A19, wherein the ligase is a T4 DNA ligase.

Embodiment A21. The method of any one of Embodiments A1-A20, further comprising removing one or more unhybridized first probe oligonucleotides, one or more unhybridized second probe oligonucleotides, or both, from the array.

Embodiment A22. The method of Embodiment A21, wherein the removing comprises washing the one or more unhybridized first probe oligonucleotides, the one or more unhybridized second probe oligonucleotides, or both, from the array in a formamide-free wash buffer.

Embodiment A23. The method of Embodiment A21 or A22, wherein the formamide-free wash buffer is an SSC wash buffer.

Embodiment A24. The method of any one of Embodiments A21-A23, wherein SSC is present in the SSC wash buffer from about 0.01×SSC to about 1×SSC.

Embodiment A25. The method of any one of Embodiments A21-A24, wherein SSC is present in the SSC wash buffer at about 0.1×SSC.

Embodiment A26. The method of any one of Embodiments A21-A25, wherein the SSC wash buffer comprises a detergent.

Embodiment A27. The method of Embodiment A26, wherein the detergent comprises sodium dodecyl sulfate (SDS).

Embodiment A28. The method of any one of Embodiments A21-A26, wherein SDS is present in the SSC wash buffer from about 0.01% (v/v) to about 0.5% (v/v).

Embodiment A29. The method of any one of Embodiments A21-A28, wherein the SDS is present in the SSC wash buffer at about 0.1% (v/v).

Embodiment A30. The method of any one of Embodiments A21-A29, wherein the SSC wash buffer comprises a solvent.

Embodiment A31. The method of any one of Embodiments A21-A30, wherein the solvent comprises ethylene carbonate.

Embodiment A32. The method of any one of Embodiments A21-A31, wherein ethylene carbonate is present in the SSC wash buffer from about 10% (w/v) to about 25% (w/v).

Embodiment A33. The method of any one of Embodiments A21-A32, wherein ethylene carbonate is present in the SSC wash buffer from about 15% (w/v) to about 20% (w/v).

Embodiment A34. The method of any one of Embodiments A21-A33, wherein ethylene carbonate is present in the SSC wash buffer at about 16% (w/v).

Embodiment A35. The method of any one of Embodiments A21-A34, wherein the SSC wash buffer is at a temperature from about 50° C. to about 70° C.

Embodiment A36. The method of any one of Embodiments A21-A35, wherein the SSC wash buffer is at temperature from about 55° C. to about 65° C.

Embodiment A37. The method of any one Embodiments A21-A36, where in the SSC wash buffer is at a temperature of about 60° C.

Embodiment A38. The method of any one of Embodiments A1-A37, wherein releasing in step (e) comprises contacting the ligation product with an endoribonuclease.

Embodiment A39 The method of Embodiment A38, wherein the endoribonuclease is one or more of RNase H, RNase A, RNase C, or RNase I.

Embodiment A40. The method of Embodiment A38 or A39, wherein the endoribonuclease is RNAse H.

Embodiment A41. The method of Embodiment A40, wherein the RNase H comprises RNase H1, RNase H2, or both.

Embodiment A42. The method of any one Embodiments A1-A41, further comprising extending a 3' end of the capture probe using the ligation product as a template for an extension reaction.

Embodiment A43. The method of Embodiment A42, wherein extending the 3' end of the capture probe comprises reverse transcribing the analyte, thereby generating a sequence complementary to the analyte.

Embodiment A44. The method of Embodiment A43, wherein reverse transcribing the analyte comprises a reverse transcriptase.

Embodiment A45. The method of any of one of Embodiments A1-A44, wherein the analyte is RNA.

Embodiment A46. The method of any one of Embodiments A1-A45, wherein the RNA is an mRNA.

Embodiment A47. The method of any one of Embodiments A1-A46, wherein the biological sample is a tissue sample.

Embodiment A48. The method of Embodiment A47, wherein the tissue sample is a tissue section.

Embodiment A49. The method of any one of Embodiments A1-A46, wherein the biological sample a fresh frozen biological sample.

Embodiment A50. The method of any one of Embodiments A1-A46, wherein the biological sample is a fixed biological sample.

Embodiment A51. The method of Embodiment A41, wherein the fixed biological sample is a formalin-fixed paraffin-embedded sample.

Embodiment A52. The method of any one of Embodiments A1-A51, wherein the method further comprises permeabilizing the biological sample.

Embodiment A53. The method of Embodiment A52, wherein permeabilizing the biological sample occurs before releasing the ligation product from the analyte.

Embodiment A54. The method of Embodiment A52 or A53, wherein permeabilizing the biological sample comprises an endopeptidase.

Embodiment A55. The method of any one of Embodiments A1-A54, wherein the method further comprises amplifying the ligation product prior to contacting the biological sample with the array.

Embodiment A56. The method of any one of Embodiments A1-A55, wherein determining in step (f) comprises sequencing.

Embodiment A57. The method of any one of Embodiments A1-A56, wherein the method further comprises a capture probe capture domain blocking moiety that specifically binds the capture probe capture domain.

Embodiment A58. The method of any one of Embodiments A1-A57, further comprising releasing the capture probe capture domain blocking moiety from the capture probe capture domain prior to contacting the biological sample with the array.

Embodiment A59. The method of any one of Embodiments A1-A58, wherein the capture probe capture domain comprises a homopolymeric sequence.

Embodiment A60. The method of Embodiment A59, wherein the capture probe capture domain comprises a poly(A) sequence.

Embodiment B

Embodiment B1. A method for identifying a location of an analyte in a biological sample, the method comprising:

(a) contacting the biological sample with a substrate comprising a plurality of capture probes, wherein a capture probe of the plurality of capture probes comprises a capture domain and a spatial barcode;

(b) contacting the biological sample with a first probe and a second probe, wherein a portion of the first probe and a portion of the second probe are substantially complementary to adjacent sequences of the analyte, wherein the first probe comprises a sequence that is substantially complementary to a first target sequence of the analyte, wherein the second probe comprises:
(i) a first sequence that is substantially complementary to a second target sequence of the analyte;
(ii) a linker sequence;
(iii) a second sequence that is substantially complementary to a third target sequence of the analyte; and
(iv) a capture probe capture domain that is capable of binding to a capture domain of a capture probe;

(c) hybridizing the first probe and the second probe to the analyte;

(d) ligating the first probe and the second probe, thereby creating a ligation product;

(e) releasing the ligation product from the analyte;

(f) hybridizing the capture probe capture domain to a capture domain; and (g) determining (i) all or a part of the sequence of the ligation product specifically bound to the capture domain, or a complement thereof, and (ii) all or a part of the sequence of the spatial barcode, or a complement thereof, and using the determined sequence of (i) and (ii) to identify the location of the analyte in the biological sample.

Embodiment B2. The method of Embodiment B1, wherein the second probe comprises from 5' to 3': a first sequence, a linker sequence, a second sequence, and a capture probe capture domain.

Embodiment B3. The method of any one of Embodiments B 1-B2, wherein the first target sequence of the analyte is directly adjacent to the second target sequence of the analyte.

Embodiment B4. The method of any one of Embodiments B 1-B3, wherein the second target sequence is not directly adjacent to the third target sequence on the analyte.

Embodiment B5. The method of any one of Embodiments B 1-B4, wherein the second target sequence and the third target sequence are on different exons of the analyte.

Embodiment B6. The method of any one of Embodiments B 1-B4, wherein the second target sequence and the third target sequence are within the same exon of the analyte but are not directly adjacent.

Embodiment B7. The method of any one of Embodiments B 1-B6, wherein the linker sequence comprises a total of about 1 nucleotide to about 100 nucleotides.

Embodiment B8. The method of Embodiment B7, wherein the linker further comprises a barcode sequence that serves as a proxy for identifying the analyte.

Embodiment B9. A method for identifying a location of an analyte in a biological sample, the method comprising:

(a) contacting the biological sample with a substrate comprising a plurality of capture probes, wherein a capture probe of the plurality of capture probes comprises a capture domain and a spatial barcode;

(b) contacting the biological sample with a first probe and a second probe, wherein a portion of the first probe and a portion of the second probe are substantially complementary to adjacent sequences of the analyte, wherein the first probe comprises:
(i) a first sequence that is substantially complementary to a first target sequence of the analyte;
(ii) a linker sequence;
(iii) a second sequence that is substantially complementary to a second target sequence of the analyte; and wherein the second probe comprises a sequence that is substantially complementary to a third target sequence of the analyte and a capture probe capture domain that is capable of binding to a capture domain of a capture probe;

(c) hybridizing the first probe and the second probe to the analyte;

(d) ligating the first probe and the second probe, thereby creating a ligation product;

(e) releasing the ligation product from the analyte;

(f) hybridizing the capture probe capture domain to a capture domain; and (g) determining (i) all or a part of the sequence of the ligation product specifically bound to the capture domain, or a complement thereof, and (ii) all or a part of the sequence of the spatial barcode, or a complement thereof, and using the determined sequence of (i) and (ii) to identify the location of the analyte in the biological sample.

Embodiment B10. The method of Embodiment F9, wherein the second target sequence is directly adjacent to the third target sequence.

Embodiment B11. The method of any one of Embodiments B9-B10, wherein the first probe comprises from 5' to 3': a first sequence, a linker sequence, and a second sequence.

Embodiment B12. The method of any one of Embodiments B9-B11, wherein the first probe further comprises a functional sequence.

Embodiment B13. The method of Embodiment B13, wherein the functional sequence is a primer sequence.

Embodiment B14. The method of Embodiment B12 or B13, wherein the first probe comprises from 5' to 3': a functional sequence, a first sequence, a linker sequence, and a second sequence.

Embodiment B15. The method of any one of Embodiments B9-B14, wherein the first target sequence is not directly adjacent to the second target sequence on the analyte.

Embodiment B16. The method of Embodiment B15, wherein the first target sequence and second target sequence of are on different exons.

Embodiment B17. The method of Embodiment B15, wherein the first target sequence and the second target sequence are within the same exon but are not directly adjacent.

Embodiment B18. The method of any one of Embodiments B9-B17, wherein the linker sequence comprises a total of about 1 nucleotide to about 100 nucleotides.

Embodiment B19. The method of Embodiment B18, wherein the linker further comprises a barcode sequence that serves as a proxy for identifying the analyte.

Embodiment B20. A method for identifying a location of an analyte in a biological sample, the method comprising:

(a) contacting the biological sample with a substrate comprising a plurality of capture probes, wherein a capture probe of the plurality of capture probes comprises a capture domain and a spatial barcode;

(b) contacting the biological sample with a first probe, a second probe, and one or more spanning probes, wherein the first probe is substantially complementary to a first portion of the analyte, wherein the second probe is substantially complementary to a second portion of the analyte and further comprises a capture probe capture domain, and wherein the spanning probe comprises:

(i) a first sequence that is substantially complementary to a first target sequence of the analyte, and (ii) a second sequence that is substantially complementary to a second target sequence of the analyte;

(c) hybridizing the first probe, the second probe, and the spanning probe to the analyte;

(d) ligating the first probe, the one or more spanning probes, and the second probe, thereby creating a ligation product that is substantially complementary to the analyte;

(e) releasing the ligation product from the analyte;

(f) hybridizing the capture probe capture domain to a capture domain; and (g) determining (i) all or a part of the sequence of the ligation product specifically bound to the capture domain, or a complement thereof, and (ii) all or a part of the sequence of the spatial barcode, or a complement thereof, and using the determined sequence of (i) and (ii) to identify the location of the analyte in the biological sample.

Embodiment B21. The method of Embodiment B20, wherein the spanning oligonucleotide further comprises a functional sequence.

Embodiment B22. The method of Embodiment B20 or B, wherein the spanning oligonucleotides comprises from 5' to 3': a first sequence, a functional sequence, and a second sequence.

Embodiment B23. The method of any one of Embodiments B20-B22, wherein the functional sequences comprises a linker sequence.

Embodiment B24. The method of Embodiment B23, wherein the linker sequence comprises a total of about 1 nucleotides to about 100 nucleotides.

Embodiment B25. The method of any one of Embodiments B20-B24, wherein the functional sequences comprises a barcode sequence.

Embodiment B26. The method of Embodiment B25, wherein the barcode sequence comprises a sequence that serves as a proxy for identifying the analyte.

Embodiment B27. The method of any one of Embodiments B20-B26, wherein the functional sequence comprises one or more linker sequences and a barcode sequence.

Embodiment B28. The method of Embodiment B27, wherein the functional sequence comprises a barcode sequence flanked by linker sequences.

Embodiment B29. The method of any one of Embodiments B20-B28, wherein the linker sequence comprises a total of about 1 nucleotides to about 100 nucleotides.

Embodiment B30. The method of any one of Embodiments B20-B29, wherein the first sequence of the spanning probe and the second sequence of the spanning probe are substantially complementary to sequences within the same exon.

Embodiment B31. The method of Embodiment B30, wherein the first target sequence of the analyte and the second target of the analyte are located within the same exon.

Embodiment B32. The method of any one of Embodiments B20-B29, wherein the first sequence of the spanning probe and the second sequence of the spanning probe are substantially complementary to sequences within the different exons of the same gene.

Embodiment B33. The method of Embodiment B32, wherein the first target sequence of the analyte and the second target sequence of the analyte are located on different exons of the same gene.

Embodiment B34. The method of any one of Embodiments B20-33, wherein the first portion of the analyte is directly adjacent to the first target sequence, and/or wherein the second portion of the analyte is directly adjacent to the second target sequence.

Embodiment B35. The method of any one of Embodiments B20-B34, wherein the spanning probe comprises at least two ribonucleic acid based at the 3' end.

Embodiment B36. The method of any one of Embodiments B20-B35, wherein the spanning probe comprises a phosphorylated nucleotide at the 5' end.

Embodiment B37. The method of any one of Embodiments B20-B36, wherein the one or more spanning probes comprises one spanning probe.

Embodiment B38. The method of any one of Embodiments B20-B36, wherein the one or more spanning probes comprises at least two, at least three, at least four, at least five, or more spanning probes.

Embodiment B39. The method of Embodiment B38, wherein the one or more spanning probes comprise:

(i) a third sequence that is substantially complementary to a third target sequence of the analyte, and (ii) a fourth sequence that is substantially complementary to a fourth target sequence of the analyte.

Embodiment B40. The method of Embodiment B39, wherein the first target sequence is located in a first exon, the second target sequence is located in a second exon, and the third target sequence and the fourth target sequence are located in a third exon.

Embodiment B41. The method of Embodiments B39, wherein the first target sequence is located in a first exon, the second target sequence is located in a second exon, and the third target sequence is located in a third exon, and the fourth target sequence is located in a fourth exon.

Embodiment B42. The method of any one of Embodiments B38-B41, wherein the method comprises ligating:

the first probe to the spanning probe, the spanning probe to one or more additional spanning probes, and the one or more additional spanning probes spanning oligonucleotide to the second probe, thereby creating a ligation product that is substantially complementary to the analyte.

Embodiment B43. The method of any one of Embodiments B38-B42, wherein the one or more additional spanning probes oligonucleotide further comprises a functional sequence.

Embodiment B44. The method of Embodiment B43, wherein the functional sequences comprises (i) a linker sequence, (ii) a barcode sequence, or (ii) one or more linkers and a barcode sequence.

Embodiment B45. The method of any one of Embodiments B38-B44, wherein the one or more additional spanning probes comprises at least two ribonucleic acid based at the 3' end.

Embodiment B46. The method of any one of Embodiments B38-B45, wherein the one or more additional spanning probes comprises a phosphorylated nucleotide at the 5' end.

Embodiment B47. The method of any one of Embodiments B20-B46, wherein the first probe further comprises a functional sequence.

Embodiment B48. The method of Embodiment B47, wherein the functional sequence is a primer sequence.

Embodiment B49. The method of any one of the preceding Embodiments, wherein the first probe comprises at least two ribonucleic acid bases at the 3' end.

Embodiment B50. The method of any one of the preceding Embodiments, wherein the second probe comprises a phosphorylated nucleotide at the 5' end.

Embodiment B51. The method of any one of the preceding Embodiments, wherein the method further comprises providing a capture probe capture domain blocking moiety that interacts with the capture probe capture domain.

Embodiment B52. The method of Embodiment B51, wherein the method further comprises releasing the capture probe capture domain blocking moiety from the capture probe capture domain prior to step (f).

Embodiment B53. The method of any one of the preceding Embodiments, wherein the capture probe capture domain comprises a poly-adenylated (poly(A)) sequence or a complement thereof.

Embodiment B54. The method of Embodiment B53, wherein the capture probe capture domain blocking moiety comprises a poly-uridine sequence, a poly-thymidine sequence, or both.

Embodiment B55. The method of Embodiment B52, wherein releasing the poly-uridine sequence from the poly (A) sequence comprises denaturing the ligation product or contacting the ligation product with an endonuclease or exonuclease.

Embodiment B56. The method of any one of the preceding Embodiments, wherein the capture probe capture domain comprises a sequence that is complementary to all or a portion of the capture domain of the capture probe.

Embodiment B57. The method of any one of the preceding Embodiments, wherein the capture probe capture domain comprises a degenerate sequence.

Embodiment B58. The method of any one of the preceding Embodiments, wherein the ligation step comprises using enzymatic ligation or chemical ligation.

Embodiment B59. The method of Embodiment B58, wherein the enzymatic ligation utilizes a ligase.

Embodiment B60. The method of Embodiment B59, wherein the ligase is one or more of a T4 RNA ligase (Rnl2), a splintR ligase, a single stranded DNA ligase, or a T4 DNA ligase.

Embodiment B61. The method of Embodiment B60, wherein the ligase is a T4 RNA ligase 2 (Rnl2) ligase.

Embodiment B62. The method of any one of the preceding Embodiments, wherein the first probe, the second probe, and the one or more spanning probes are DNA probes.

Embodiment B63. The method of Embodiment B62, wherein the steps (b) and (c) each creates a RNA: DNA hybrid.

Embodiment B64. The method of any one of the preceding Embodiments, wherein steps (b) and (c) are performed at substantially the same time.

Embodiment B65. The method of any one of the preceding Embodiments, wherein the biological sample comprises a FFPE sample.

Embodiment B66. The method of Embodiment B65, wherein the tissue sample is the FFPE tissue sample, and the tissue sample is decrosslinked.

Embodiment B67. The method of any one of the preceding Embodiments, wherein the biological sample comprises a tissue section.

Embodiment B68. The method of any one of the preceding Embodiments, wherein the biological sample comprises a fresh frozen sample.

Embodiment B69. The method of any one of the preceding Embodiments, wherein the biological sample comprises live cells.

Embodiment B70. The method of any one of the preceding Embodiments, wherein the analyte comprises RNA and/or DNA.

Embodiment B71. The method of any one of the preceding Embodiments, wherein the analyte is RNA.

Embodiment B72. The method of Embodiment B71, wherein the RNA is an mRNA.

Embodiment B73. The method of any one of the preceding Embodiments, wherein the biological sample was previously stained.

Embodiment B74. The method of Embodiment B73, wherein the biological sample was previously stained using hematoxylin and eosin (H&E).

Embodiment B75. The method of Embodiment B73 or B74, wherein the biological sample was previously stained using immunofluorescence or immunohistochemistry.

Embodiment B76. The method of any one of the preceding Embodiments, wherein the method further comprises contacting the biological sample with a permeabilization agent.

Embodiment B77. The method of any one of the preceding Embodiments, wherein the releasing step comprises removing the ligated probe from the analyte.

Embodiment B78. The method of Embodiment B77, wherein the releasing step comprises contacting the ligated probe with an endoribonuclease.

Embodiment B79. The method of Embodiment B78, wherein the endoribonuclease is one or more of RNase H, RNase A, RNase C, or RNase I.

Embodiment B80. The method of Embodiment B79, wherein the RNase H comprises RNase H1, RNase H2, or RNase H1 and RNase H2.

Embodiment B81. The method of any one of the preceding Embodiments, wherein the determining step comprises amplifying all or part of the ligation product specifically bound to the capture domain.

Embodiment B82. The method of Embodiment B81, wherein the amplifying is isothermal.

Embodiment B83. The method of Embodiment B81, wherein the amplifying is not isothermal.

Embodiment B84. The method of any one of Embodiments B81-B83, wherein an amplifying product comprises (i) all or part of sequence of the ligation product specifically bound to the capture domain, or a complement thereof, and (ii) all or a part of the sequence of the spatial barcode, or a complement thereof.

Embodiment B85. The method of any one of the preceding Embodiments, wherein the determining step comprises sequencing.

Embodiment B86. The method of Embodiment B85, wherein the sequencing step comprises in situ sequencing.

Embodiment B87. A kit comprising
(a) an array comprising a plurality of capture probes;
(b) a plurality of probes comprising a first probe and a second oligonucleotide, wherein the first probe and the second probe are substantially complementary to adjacent sequences of an analyte, wherein the second probe comprises (i) a capture probe capture domain that is capable of binding to a capture domain of the capture probe and (ii) a linker sequence;
(c) a plurality of enzymes comprising a ribonuclease and a ligase; and
(d) an instruction for using the kit.

Embodiment B88. A kit comprising
(a) an array comprising a plurality of capture probes;
(b) a plurality of probes comprising a first probe and a second oligonucleotide, wherein the first probe and the second probe are substantially complementary to adjacent sequences of an analyte, wherein the first probe includes a linker sequence, wherein the second probe comprises a capture probe capture domain that is capable of binding to a capture domain of the capture probe;
(c) a plurality of enzymes comprising a ribonuclease and a ligase; and
(d) an instruction for using the kit.

Embodiment B89. A kit comprising:
(a) an array comprising a plurality of capture probes;
(b) a plurality of probes comprising a first probe and a second oligonucleotide, wherein the second probe comprises a capture probe capture domain that is capable of binding to a capture domain of the capture probe;
(c) a plurality of spanning probes, wherein a spanning probe of the plurality of spanning probes comprises a first sequence, a linker sequence, and a second sequence, wherein the first sequence of the spanning probe and the first probe are substantially complementary to adjacent sequences of an analyte, wherein the second sequence of the spanning probe and the second probe are substantially complementary to adjacent sequences of the analyte;
(d) a plurality of enzymes comprising a ribonuclease and a ligase; and
(e) an instruction for using the kit.

Embodiment B90. The kit of any one of Embodiments B87-B89, wherein the ribonuclease is RNase H.

Embodiment B91. The kit of any one of Embodiments B87-B90, wherein the ligase is one or more of a T4 RNA ligase (Rnl2), a splintR ligase, a single stranded DNA ligase, or a T4 DNA ligase.

Embodiment B92. The kit of Embodiment B91, wherein the ligase is a T4 RNA ligase 2 (Rnl2) ligase.

What is claimed is:

1. A composition comprising:
(a) a spatial array comprising a plurality of capture probes affixed to a substrate, wherein a capture probe of the plurality of capture probes comprises (i) a spatial barcode and (ii) a capture domain, wherein the spatial barcode comprises a sequence that provides a location of an analyte in a biological sample;
(b) the biological sample placed on the spatial array, wherein the biological sample comprises the analyte; and
(c) a first probe and a second probe that are ligated together, thereby generating a ligation product, wherein the first probe and the second probe each comprise a sequence that is substantially complementary to a sequence of the analyte, and wherein one of the first probe or the second probe comprises a capture probe capture domain that is hybridized to the capture domain of the capture probe on the spatial array.

2. The composition of claim 1, wherein the first probe or the second probe that does not comprise the capture probe capture domain comprises a primer sequence.

3. The composition of claim 1, wherein the second probe comprises the capture probe capture domain.

4. The composition of claim 1, wherein the first probe further comprises a primer sequence.

5. The composition of claim 1, wherein the first probe and the second probe are substantially complementary to adjacent sequences of the analyte.

6. The composition of claim 1, wherein the first probe and the second probe are substantially complementary to sequences that are not adjacent to each other on the analyte, wherein one of the first probe or the second probe is extended with a DNA polymerase.

7. The composition of claim 1, wherein the first probe comprises at least two ribonucleic acid bases at the 3' end, and wherein the second probe comprises a phosphorylated nucleotide at the 5' end.

8. The composition of claim 1, wherein the first probe and/or the second probe is a DNA probe.

9. The composition of claim 1, further comprising 5000 or more ligated probe pairs, wherein a ligated probe pair of the 5000 or more ligated probe pairs comprises the first probe and the second probe that are ligated together, and wherein at least one of the ligated probe pairs is hybridized to the capture domain of the capture probe on the spatial array.

10. The composition of claim 1, wherein prior to ligation to the second probe the first probe comprised a pre-adenylated phosphate group at its 5' end.

11. The composition of claim 1, wherein the capture probe capture domain comprises a poly-adenylated sequence or a complement thereof.

12. The composition of claim 1, wherein the capture probe capture domain comprises a degenerate sequence.

13. The composition of claim 1, wherein the capture domain comprises a poly-uridine sequence or a poly-thymidine sequence.

14. The composition of claim 1, wherein the analyte comprises mRNA.

15. The composition of claim 1, further comprising a DNA polymerase.

16. The composition of claim 1, further comprising a RNase H enzyme, wherein the RNase H enzyme comprises RNase H1, RNase H2, or both.

17. The composition of claim 1, further comprising a permeabilization agent.

18. The composition of claim 17, wherein the permeabilization agent is proteinase K or pepsin.

19. The composition of claim 1, further comprising a ligase and wherein the ligase is one or more of a T4 RNA ligase (Rnl2), a PBCV-1 ligase, a single stranded DNA ligase, or a T4 DNA ligase.

20. The composition of claim 1, wherein the biological sample is a tissue sample comprising cells.

21. The composition of claim 20, wherein the tissue sample is a formalin-fixed, paraffin-embedded tissue sample, a fresh tissue sample, or a frozen tissue sample.

22. The composition of claim 21, wherein the tissue sample is a formalin-fixed, paraffin-embedded tissue sample.

23. The composition of claim 1, wherein the biological sample was previously stained.

24. The composition of claim 23, wherein the biological sample was previously stained using immunofluorescence or immunohistochemistry.

25. The composition of claim 23, wherein the biological sample was previously stained using hematoxylin and eosin.

26. The composition of claim 1, wherein the biological sample was previously fixed with one or both of methanol and acetone.

27. The composition of claim 1, wherein the spatial array comprises a plurality of features, and wherein the plurality of features corresponds to the plurality of capture probes.

28. The composition of claim 27, wherein the plurality of features comprises beads.

29. A method for determining the spatial location of an analyte in a biological sample comprising the composition of claim 1.

30. The method of claim 29, wherein the method further comprises determining (i) all or part of the sequence of the ligation product, or a complement thereof, and (ii) the sequence of the spatial barcode, or a complement thereof, and using the determining sequences of (i) and (ii) to determining the spatial location of the analyte in the biological sample.

* * * * *